United States Patent

Masui et al.

(12) 
(10) Patent No.: US 6,251,949 B1
(45) Date of Patent: Jun. 26, 2001

(54) OXIME DERIVATIVES, HYDRAZONE DERIVATIVES AND USE THEREOF

(75) Inventors: Moriyasu Masui, Yokkaichi; Norihiko Tanimoto, Nabari; Kuniyoshi Nishida, Shiga, all of (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 09/457,672

(22) Filed: Dec. 9, 1999

Related U.S. Application Data

(62) Division of application No. 09/284,239, filed on Apr. 14, 1999, now Pat. No. 6,096,741.

(30) Foreign Application Priority Data

Oct. 15, 1996 (JP) .......................................... 272154

(51) Int. Cl.[7] .......................... A61K 31/15; A61K 31/42; A61K 31/54; C07C 249/00; C07D 223/04
(52) U.S. Cl. .......................... 514/640; 514/378; 514/351; 514/227.5; 514/212; 564/256; 548/248; 544/59; 540/607
(58) Field of Search ............................ 564/256; 548/248; 546/300; 544/59; 540/607; 514/640, 378, 351, 227.5, 212

(56) References Cited

U.S. PATENT DOCUMENTS

| | | |
|---|---|---|
| 4,568,671 | 2/1986 | D'Silva . |
| 4,576,965 | 3/1986 | D'Silva . |
| 4,612,326 | 9/1986 | D'Silva . |
| 5,935,999 | * 8/1999 | Worthington et al. ............... 514/640 |
| 5,977,182 | * 11/1999 | Zurfluh et al. ....................... 514/640 |
| 6,028,093 | * 2/2000 | Muller et al. ......................... 514/384 |

FOREIGN PATENT DOCUMENTS

| | | |
|---|---|---|
| 387499 | 9/1990 | (EP) . |
| 50-35336 | 4/1975 | (JP) . |
| 55-127363 | 10/1980 | (JP) . |
| 56-167664 | 12/1981 | (JP) . |
| WO 96/11183 | 4/1996 | (WO) . |
| WO 97/37968 | 10/1997 | (WO) . |

OTHER PUBLICATIONS

M. Roman Sawicki et al., "Response of Susceptible and Resistant Peach–Potato Aphids Myzus Persicae (Sulz.) to Insecticides in Leaf–Dip Bioassays", Pesticide Science, vol. 9, pp. 513–516, 1978.

* cited by examiner

*Primary Examiner*—Deborah C. Lambkin
(74) *Attorney, Agent, or Firm*—Oblon, Spivak, McClelland, Maier & Neustradt, P.C.

(57) ABSTRACT

Compounds having fungicidal activities and represented by general formula (I) and salts and hydrates thereof

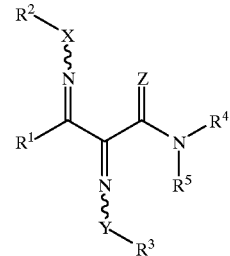

wherein $R^1$ represents an optionally substituted aryl, an optionally substituted alkyl or the like; $R^2$ represents an optionally substituted alkyl, an optionally substituted alkenyl, an optionally substituted alkynyl, an optionally substituted aryl, an optionally substituted heterocyclic group or the like; $R^3$ represents an optionally substituted alkyl, an optionally substituted alkenyl, an optionally substituted alkynyl, an optionally substituted arylsulfonyl, an optionally substituted heterocyclic group or the like; $R^4$ and $R^5$, which may be the same or different, represent each a hydrogen atom, an optionally substituted alkyl, or an optionally substituted alkoxy, or $R^4$ and $R^5$ may form together with the adjacent nitrogen atom an optionally substituted monocycle or polycycle; X and Y, which may be the same or different, represents each an oxygen atom or $NR^6$ wherein $R^6$ represents a hydrogen atom, an optionally substituted alkyl, an optionally substituted aryl, an optionally substituted alkanoyl, or an optionally substituted aroyl; Z represents an oxygen atom or a sulfur atom; and a wavy line (~) represents the configuration of an E isomer, a Z isomer, or a mixture thereof.

14 Claims, No Drawings

OXIME DERIVATIVES, HYDRAZONE DERIVATIVES AND USE THEREOF

This application is a divisional of U.S. application Ser. No. 09/284,239 filed Apr. 14, 1999, U.S. Pat. No. 6,096,741, which was filed as International Application No. PCT/JP97/03585 filed Oct. 7, 1997.

TECHNICAL FIELD

The present invention relates to a novel oxime derivative and a novel hydrazone derivative as well as the use of the same.

BACKGROUND ART

While as oxime derivatives and hydrazone derivatives analogous to the present invention Japanese Patent Application Laid-Open Nos. 3-215464 and 7-309825, and WO 95/21153, WO 95/21154, WO 95/18789 and WO 96/11183 disclose compounds having fungicidal activities, a compound disclosed in the present invention is not included in these publications. In addition, none of these publications mentioned the tachykinin receptor antagonism of the compounds disclosed therein.

Tachykinin is a name which is used commonly in a group of the neuropeptides having 10 to 11 amino acids, and includes substance P, neurokinin A and neurokinin B which are known. Each of these substances binds to three receptors, namely NK1, NK2 and NK3, and is known to be involved in pain transmission, vasodilation, saliva secretion, increase in capillary vessel permeability, immunoregulation, nerve cell regulation and the like. Accordingly, a compound having a tachykinin receptor antagonistic effect is considered to have various biological activities, and each of EP 394989, EP 428434, EP 429366, EP 436334, EP 443132, EP 474561, EP 482 539, EP 499313, EP 512901, EP 512902, EP 514273, EP 514275, EP 515240, EP 517589, EP 520555, EP 522808, EP 528495, EP 532456, EP 533280, EP 536817, EP 545478, EP 559538, EP 585913, WO 90/05525, WO 90/05729, WO 91/09844, WO 91/18899, WO 92/01688, WO 92/06079, WO 92/12151, WO 95/15585, WO 92/19254, WO 92/20661, WO 92/20667, WO 93/00330, WO 93/00331, WO 93/01159, WO 93/01165, WO 93/01169, WO 93/01170, WO 93/06099, WO 93/09116, WO 93/10073, WO 93/14084, WO 93/18023, WO 93/19064, WO 93/21155, WO 93/21181, WO 93/23380, WO 94/16697, WO 94/17045, WO 94/19323, WO 94/20500, WO 94/26740, WO 94/29309, WO 95/02595, WO 95/04040, WO 95/04042, WO 95/18124, WO 95/18129, WO 95/28389, WO 96/29326, WO 96/30367, Japanese Patent Application Laid-Open Nos. 8-239323, 8-295667, 8-2301849 and 8-301871 discloses a compound having a tachykinin receptor antagonistic effect.

However, none of these publications describes an oxime derivative or a hydrazone derivative disclosed in the present invention.

DISCLOSURE OF INVENTION

An objective of the present invention is to provide a compound having a higher fungicidal effect and a higher tachykinin receptor antagonistic effect.

The present inventors made an effort to achieve the objective described above and finally found that a novel oxime derivative and a novel hydrazone derivative described below have a higher fungicidal effect and a higher tachykinin receptor antagonistic effect, whereby accomplishing the present invention.

Thus, the present invention is a compound represented by Formula (I):

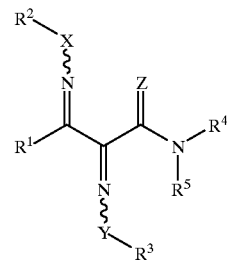

wherein $R^1$ is an optionally substituted aryl, an optionally substituted alkyl or an optionally substituted cycloalkyl; $R^2$ is an optionally substituted alkyl, an optionally substituted cycloalkyl, an optionally substituted alkenyl, an optionally substituted alkynyl, an optionally substituted alkylsulfonyl, an optionally substituted aryl, an optionally substituted arylsulfonyl or an optionally substituted heterocyclic group; $R^3$ is an optionally substituted alkyl, an optionally substituted cycloalkyl, an optionally substituted alkenyl, an optionally substituted alkynyl, an optionally substituted alkylsulfonyl, an optionally substituted aryl, an optionally substituted arylsulfonyl or an optionally substituted heterocyclic group; $R^4$ and $R^5$ are the same or different from each other and each is a hydrogen atom, an optionally substituted alkyl, an optionally substituted cycloalkyl or an optionally substituted alkoxy, or $R^4$ and $R^5$ may be taken together with their adjacent nitrogen atom to form an optionally substituted monocyclic ring or polycyclic ring; X and Y are the same or different from each other and each is an oxygen atom or an $NR^6$ wherein $R^6$ is a hydrogen atom, an optionally substituted alkyl, an optionally substituted aryl, an optionally substituted alkanoyl or an optionally substituted aroyl; Z is an oxygen atom or a sulfur atom; a wave-shaped line (~) represents the configuration of a E form or a Z form or a mixture thereof;

provided that when $R^2$ is an optionally substituted benzyl, then the substituent is not a group represented by formula:

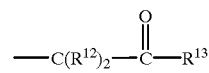

wherein $(R^{12})_2$ is $H_2$, =O, =CH—OH, =CHOCH$_3$, =N—OH or =N—OCH$_3$; and $R^{13}$ represents an alkoxy or a monoalkylamino;

and a salt or a hydrate thereof preferably a compound or a salt or a hydrate thereof described above wherein $R^1$ is an aryl or an alkyl; $R^2$ is an optionally substituted alkyl, alkenyl, alkynyl, aryl or heterocyclic group; $R^3$ is an optionally substituted alkyl, alkenyl, alkynyl, an optionally substituted aryl, an optionally substituted arylsulfonyl or heterocyclic group; $R^4$ and $R^5$ are the same or different from each other and each is a hydrogen atom, an alkyl or an alkoxy, or $R^4$ and $R^5$ may be taken together with their adjacent nitrogen atom to form an optionally substituted monocyclic ring; X and Y are the same or different from each other and each is an oxygen atom or a $NR^6$ wherein $R^6$ is a hydrogen atom, alkyl, aryl, alkanoyl or aroyl.

BEST MODE FOR CARRYING OUT THE INVENTION

In this specification, the term "lower" means a straight or branched chain group having 1 to 8 carbon atoms, preferably 1 to 6 carbon atoms, more preferably 1 to 4 carbon atoms, unless otherwise specified.

The aryl in an optionally substituted aryl represented by $R^1$ may be an aryl having 6 to 14 carbon atoms, such as phenyl, naphthyl (e.g., 1-naphthyl, 2-naphthyl) and the like.

The substituent on an optionally substituted aryl represented by $R^1$ may for example be a lower alkyl (e.g., methyl, ethyl, propyl, butyl and the like), a lower alkenyl (e.g., vinyl, allyl, 2-butenyl and the like), a lower alkynyl (e.g., ethynyl, 2-propynyl, 3-butynyl and the like), a cycloalkyl (e.g., cyclopropyl, cyclopentyl, cyclohexyl and the like), a cycloalkenyl (e.g., cyclopentenyl, cyclohexenyl and the like), a halogenated lower alkyl (e.g., trifluoromethyl, trichloromethyl, difluoromethyl, chloromethyl, 2-bromoethyl, 1,2-dichloropropyl and the like), a halogen atom (e.g., fluorine atom, chlorine atom, bromine atom, iodine atom), nitro, cyano, a lower alkylthio (e.g., methylthio, ethylthio, propylthio and the like), —$NR^8R^9$ wherein $R^8$ and $R^9$ are the same or different from each other and each is a hydrogen atom, an optionally substituted lower alkyl (e.g., methyl, ethyl, propyl, 2-chloroethyl, methoxymethyl, 2-ethoxyethyl, benzyl, 4-chlorobenzyl, 2-oxopropyl, methoxycarbonylmethyl, ethoxycarbonylmethyl, carbamoylmethyl and the like), formyl, a lower alkanoyl (e.g., acetyl, propionyl and the like), a lower alkoxycarbonyl (e.g., methoxycarbonyl, ethoxycarbonyl and the like), an optionally substituted aryl (e.g., phenyl, 2-chlorophenyl, 3-chlorophenyl, 4-chlorophenyl, 2-methylphenyl, 3-methylphenyl, 4-methylphenyl, 2-methoxyphenyl, 3-methoxyphenyl, 4-methoxyphenyl, 1-naphthyl, 2-naphthyl and the like), an optionally substituted aroyl (e.g., benzoyl, 2-chlorobenzoyl, 3-chlorobenzoyl, 4-chlorobenzoyl, 2-methylbenzoyl, 3-methylbenzoyl, 4-methylbenzoyl, 2-methoxybenzoyl, 3-methoxybenzoyl, 4-methoxybenzoyl and the like), an optionally substituted lower alkylsulfonyl (e.g., methanesulfonyl, ethanesulfonyl, trifluoromethanesulfonyl and the like), an optionally substituted arylsulfonyl (e.g., benzenesulfonyl, 4-chlorobenzenesulfonyl, 4-methylbenzenesulfonyl and the like); or alternatively $R^8$ and $R^9$ may be taken together to form a cyclic system such as pyrrolidine, piperidine, morpholine, thiomorpholine, piperazine and the like, —$OR^{10}$ wherein $R^{10}$ is a hydrogen atom, a lower alkyl (e.g., methyl, ethyl, propyl and the like), a lower alkenyl (e.g., vinyl, allyl, 2-butenyl and the like), a lower alkynyl (e.g., ethynyl, 2-propynyl, 3-butynyl and the like), an optionally substituted aryl (e.g., phenyl, 2-chlorophenyl, 3-chlorophenyl, 4-chlorophenyl, 2-methylphenyl, 3-methylphenyl, 4-methylphenyl, 2-methoxyphenyl, 3-methoxyphenyl, 4-methoxyphenyl, 1-naphthyl, 2-naphthyl and the like), an alkoxyalkyl (e.g., methoxymethyl, ethoxymethyl, 2-methoxyethyl and the like), or a lower alkanoyl (e.g., acetyl, propionyl and the like), a lower alkanoyl (e.g., acetyl, propionyl and the like), a lower alkoxycarbonyl (e.g., methoxycarbonyl, ethoxycarbonyl and the like), an optionally substituted aroyl (e.g., benzoyl, 2-chlorobenzoyl, 3-chlorobenzoyl, 4-chlorobenzoyl, 2-methylbenzoyl, 3-methylbenzoyl, 4-methylbenzoyl, 2-methoxybenzoyl, 3-methoxybenzoyl, 4-methoxybenzoyl and the like), a lower alkylsulfonyl (e.g., mesyl and the like), phenyl, a phenyl(lower)alkyl (e.g., benzyl, phenethyl and the like), a phenyl(lower)alkenyl (e.g., styryl, cinnamyl and the like) and the like. Each of these substituents may be in any possible position on the respective aryl group, and may occur one to four times.

The alkyl in an optionally substituted alkyl represented by $R^1$ may be a straight or branched chain alkyl having 1 to 6 carbon atoms, preferably 1 to 4 carbon atoms, and is typically methyl, ethyl, propyl, isopropyl, butyl, isobutyl, sec-butyl, tert-butyl and the like.

The substituent on an optionally substituted alkyl may for example be nitro, cyano, a halogen atom (e.g., fluorine atom, chlorine atom. bromine atom, iodine atom), a cycloalkyl (e.g., cyclopropyl, cyclobutyl, cyclopentyl, cyclohexyl and the like), hydroxy, a lower alkoxy (e.g., methoxy, ethoxy, propoxy, isopropoxy, butoxy and the like), —$NR^8R^9$ wherein $R^8$ and $R^9$ are defined as described above, a lower alkylthio (e.g., methylthio, ethylthio, propylthio and the like), a lower alkylsulfonyl (e.g., methanesulfonyl, ethanesulfonyl and the like), an optionally substituted aryl (similar to those exemplified as an optionally substituted aryl represented by $R^1$ described above), an optionally substituted heterocyclic group (e.g., pyridin-2-yl, pyridin-3-yl, pyridin-4-yl, pyrimidin-2-yl, pyrimidin-4-yl, pyrimidin-5-yl, isoxazol-3-yl, isoxazol-5-yl, pyrrol-2-yl, pyrazol-3-yl, furan-2-yl, furan-3-yl, thiophen-2-yl, thiophen-3-yl, imidazol-2-yl, oxazol-2-yl, thiazol-2-yl and the like), =O, =$NOR^{11}$ wherein $R^{11}$ is the same or different from each other and a hydrogen atom, a lower alkyl (e.g., methyl, ethyl, propyl and the like), a lower alkenyl (e.g., allyl, 2-butenyl and the like), a lower alkynyl (e.g., 2-propynyl, 3-butynyl and the like), or a lower alkanoyl (e.g., acetyl, propionyl and the like), an optionally substituted aroyl (e.g., benzoyl, 2-chlorobenzoyl, 3-chlorobenzoyl, 4-chlorobenzoyl, 2-methylbenzoyl, 3-methylbenzoyl, 4-methylbenzoyl, 2-methoxybenzoyl, 3-methoxybenzoyl, 4-methoxybenzoyl and the like), a lower alkoxycarbonyl (e.g., methoxycarbonyl, ethoxycarbonyl and the like), an optionally substituted arylsulfonyl (e.g., benzenesulfonyl, 4-chlorobenzenesulfonyl, 4-methylbenzenesulfonyl and the like) and the like.

The cycloalkyl in an optionally substituted cycloalkyl represented by $R^1$ may be a cycloalkyl having 3 to 8 carbon atoms, preferably 3 to 6 carbon atoms. Typically, cyclopropyl, cyclopentyl and cyclohexyl may be mentioned.

The substituent on an optionally substituted cycloalkyl represented by $R^1$ may be similar to those exemplified as the substituent on an optionally substituted alkyl represented by $R^1$ described above.

$R^1$ is preferably methyl, ethyl, propyl, isopropyl, optionally substituted phenyl and the like.

Examples of an optionally substituted alkyl represented by $R^2$ may be those exemplified as an optionally substituted alkyl represented by $R^1$ described above.

Examples of an optionally substituted cycloalkyl represented by $R^2$ may be those exemplified as an optionally substituted cycloalkyl represented by $R^1$ described above.

The alkenyl in an optionally substituted alkenyl represented by $R^2$ may be an alkenyl having 2 to 6 carbon atoms, preferably 2 to 4 carbon atoms, and is typically 1-propenyl, isopropenyl, allyl, 2-butenyl and the like.

The alkynyl in an optionally substituted alkynyl represented by $R^2$ may be an alkynyl having 3 to 6 carbon atoms, preferably 3 to 4 carbon atoms, and is typically 2-propynyl, 3-butynyl and the like.

The alkyl in an optionally substituted alkylsulfonyl represented by $R^2$ may be those exemplified as an alkyl represented by $R^1$ described above.

The substituent on a substituted alkenyl, a substituted alkynyl and a substituted alkylsulfonyl represented by $R^2$ may be similar to those exemplified as the substituent on a substituted alkyl represented by $R^1$ described above.

Examples of an optionally substituted aryl represented by $R^2$ may be those exemplified as an optionally substituted aryl represented by $R^1$ described above.

Examples of an optionally substituted aryl on an optionally substituted arylsulfonyl represented by $R^2$ may be those exemplified as an optionally substituted aryl represented by $R^1$ described above.

An optionally substituted heterocyclic group represented by $R^2$ includes a non-substituted heterocyclic group as well as a substituted heterocyclic group. Examples of these heterocyclic groups are a 5- to 7-membered heterocyclic group containing 1 to 4 hetero atoms selected from the group consisting of nitrogen, sulfur and oxygen atoms, and typically, pyridyl (e.g., pyridin-2-yl, pyridin-3-yl, pyridin-4-yl), pyrimidinyl (e.g., pyrimidin-2-yl, pyrimidin-4-yl, pyrimidin-5-yl), isoxazolyl (e.g., isoxazol-3-yl, isoxazol-5-yl and the like), thiadiazolyl (e.g., 1,3,4-thiadiazol-2-yl, 1,2,3-thiadiazol-4-yl and the like), pyridazinyl (e.g., pyridazin-3-yl, pyridazin-4-yl and the like), pyrrolyl (e.g., pyrrol-1-yl, pyrrol-2-yl and the like), pyrazolyl (e.g., pyrazol-1-yl, pyrazol-3-yl and the like), furyl (e.g., furan-2-yl, furan-3-yl), thienyl (e.g., thiophen-2-yl, thiophen-3-yl), imidazolyl (e.g., imidazol-1-yl, imidazol-2-yl and the like), oxazolyl (e.g., oxazol-2-yl, oxazol-4-yl and the like), thiazolyl (e.g., thiazol-2-yl and the like), oxadiazolyl (e.g., 1,3,4-oxadiazol-2-yl, 1,2,4-oxadiazol-5-yl and the like), pyrazinyl (e.g., pyrazin-2-yl and the like), quinolyl (e.g., quinolin-2-yl and the like) and indolyl (e.g., indolin-1-yl, indolin-2-yl and the like) and the like.

Each of these heterocyclic groups may have a bond in any possible position.

The substituent on a substituted heterocyclic group represented by $R^2$ may be similar to those exemplified as the substituent on a substituted allyl represented by $R^1$ described above. Each of these substituents may be in any possible position on the respective heterocyclic group, and may occur one to three times.

$R^2$ is preferably methyl, methoxymethyl, ethyl, allyl, cinnamyl, 2-propynyl, 2-butynyl, 2-pyridyl, optionally substituted phenyl, optionally substituted benzyl, optionally substituted 2-pyridylmethyl, optionally substituted 3-pyridylmethyl, optionally substituted 4-pyridylmethyl, optionally substituted 1-naphthyl, optionally substituted 2-naphthyl, optionally substituted 2-thenyl, optionally substituted 3-thenyl and the like. In the case $R^2$ is an optionally substituted benzyl, the substituent is not a group represented by formula:

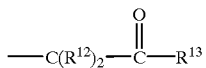

wherein $(R^{12})_2$ is $H_2$, =O, =CH—OH, =CHOCH$_3$, =N—OH or =N—OCH$_3$; and $R^{13}$ represents an alkoxy or a monoalkylamino.

The alkoxy represented by $R^{13}$ may be an alkoxy having 1 to 4 carbon atoms, and is typically methoxy, ethoxy, propoxy, butoxy and the like.

The monoalkylamino represented by $R^{13}$ may be a monoalkylamino containing an alkyl having 1 to 4 carbon atoms, and is typically monomethylamino, monoethylamino and the like.

Examples of an optionally substituted alkyl represented by $R^3$ may be those exemplified as an optionally substituted alkyl represented by $R^1$ described above.

Examples of an optionally substituted cycloalkyl represented by $R^3$ may be those exemplified as an optionally substituted cycloalkyl represented by $R^1$ described above.

Examples of an optionally substituted alkenyl represented by $R^3$ may be those exemplified as an optionally substituted alkenyl represented by $R^2$ described above.

Examples of an optionally substituted alkynyl represented by $R^3$ may be those exemplified as an optionally substituted alkynyl represented by $R^2$ described above.

Examples of an optionally substituted alkylsulfonyl represented by $R^3$ may be those exemplified as an optionally substituted alkylsulfonyl represented by $R^2$ described above.

Examples of an optionally substituted aryl represented by $R^3$ may be those exemplified as an optionally substituted aryl represented by $R^1$ described above.

Examples of an optionally substituted arylsulfonyl represented by $R^3$ may be those exemplified as an optionally substituted arylsulfonyl represented by $R^2$ described above.

Examples of an optionally substituted heterocyclic group represented by $R^3$ may be those exemplified as an optionally substituted heterocyclic group represented by $R^2$ described above.

$R^3$ is preferably methyl, ethyl, propyl, isopropyl, allyl, cinnamyl, 2-propynyl, 2-butynyl, 2-pyridyl, optionally substituted benzyl, optionally substituted 2-phenylethyl, optionally substituted 2-pyridylmethyl, optionally substituted 3-pyridylmethyl, optionally substituted 4-pyridylmethyl, optionally substituted benzenesulfonyl and the like.

Examples of an optionally substituted alkyl represented by each of $R^4$ and $R^5$ may be those exemplified as an optionally substituted alkyl represented by $R^1$ described above.

Examples of an optionally substituted cycloalkyl represented by each of $R^4$ and $R^5$ may be those exemplified as an optionally substituted cycloalkyl represented by $R^1$ described above.

Examples of the alkoxy in an optionally substituted alkoxy represented by each of $R^4$ and $R^5$ may for example be an alkoxy having 1 to 6 carbon atoms, preferably 1 to 4 carbon atoms, and is typically, methoxy, ethoxy, propoxy, isopropoxy, butoxy and the like.

Examples of the substituent on an optionally substituted alkoxy represented by each of $R^4$ and $R^5$ may be similar to those exemplified as the substituent on a substituted alkyl represented by $R^1$ described above.

$R^4$ and $R^5$ may be the same or different from each other. Alternatively, $R^4$ and $R^5$ may be taken together to form an optionally substituted monocyclic ring or polycyclic ring. Such monocyclic ring or polycyclic ring means a 4- to 8-membered cyclic system formed together with the nitrogen atom to which the two substituents are bound and optionally containing a hetero atom (e.g., oxygen, nitrogen, sulfur and the like), as well as the polycyclic ring formed as a result of condensation of these rings with other rings. Examples of such monocyclic ring and polycyclic ring are pyrrolidine, piperidine, morpholine, thiomorpholine, piperazine, hexamethyleneimine, oxazolane, diazepane, tetrahydroquinoline, tetrahydroisoquinoline and the like. The substituent on each of these cyclic systems may be those exemplified as the substituent on an optionally substituted alkyl represented by $R^1$ described above, as well as an optionally substituted lower alkyl (e.g., methyl, ethyl, propyl, 2-chloroethyl, methoxymethyl, 2-ethoxyethyl, benzyl, 4-chlorobenzyl, 2-oxopropyl, methoxycarbonylmethyl, ethoxycarbonylmethyl, carbamoylmethyl and the like), formyl, a lower alkanoyl (e.g., acetyl, propionyl and the like) and the like. Each of these substituents may be in any possible position on the respective cyclic system, and may occur one to four times.

The group —NR$^4$R$^5$ is preferably —NH$_2$, —NHMe, —NMe$_2$, —NEt$_2$, —N(Me)Et, —N(OMe)Me, optionally substituted 1-pyrrolidinyl, optionally substituted piperidino, optionally substituted morpholino, optionally substituted 4-thiomorpholinyl, optionally substituted 1-piperazinyl, optionally substituted 2-oxazolanyl, optionally substituted diazepan-1-yl.

Examples of an optionally substituted alkyl represented by $R^6$ may be those exemplified as an optionally substituted alkyl represented by $R^1$ described above.

Examples of an optionally substituted aryl represented by $R^6$ may be those exemplified as an optionally substituted aryl represented by $R^1$ described above.

The optionally substituted alkanoyl represented by $R^6$ may be an optionally substituted alkanoyl having 2 to 6 carbon atoms, preferably 2 to 4 carbon atoms, and is typically acetyl, propionyl, trifluoroacetyl and the like.

The optionally substituted aroyl represented by $R^6$ may be an optionally substituted aroyl having 7 to 16 carbon atoms, preferably 7 to 12 carbon atoms, and is typically benzoyl, 2-methylbenzoyl, 3-methylbenzoyl, 4-methylbenzoyl, 2-chlorobenzoyl, 3-chlorobenzoyl, 4-chlorobenzoyl, 4-methoxybenzoyl and the like.

Preferred examples of X are an oxygen atom, —NH—, —N(Me)—, —N(Ph)— and the like.

Preferred examples of Y are an oxygen atom, —NH—, —N(Me)—, —N(Et)—, —N(Ph)—, —N(Ac)—, —N(Bz)— and the like.

Examples of an alkyl represented by $R^7$ may be those exemplified as an alkyl represented by $R^1$ described above.

$R^7$ is preferably a hydrogen atom, methyl and ethyl.

While a compound according to the present invention occurs as any of the two isomers, i.e., an E form and a Z form, with respect to its imino moiety, the present invention encompasses these isomers as well as a mixture of these isomers in any ratio. Such isomerism is designated in the present invention using a wave-shaped line (~) in a formula.

A compound according to the present invention may also form a salt in its amino group when its hydrazone moiety or its primary to tertiary amino group is substituted, and such salt may be a mineral acid salt (e.g., hydrochlorides, sulfates, nitrates and the like) as well as an organic acid salt (e.g., acetates, maleates and the like).

A compound according to the present invention may be in a form of a hydrate.

Compound (I) according to the present invention (i.e., a compound represented by Formula (I); Hereinafter the same abbreviation may apply analogously to a compound represented by another formula) and Compound (II) may for example be produced via a synthetic route shown below.

[Route 1]

(Scheme 1)

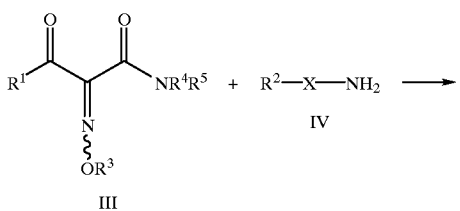

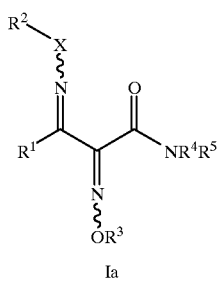

Ia wherein each radical is defined as described above.

Thus, a compound according to the present invention represented by Formula (Ia) can be prepared by reacting a hydroxylamine derivative or a hydrazine derivative represented by Formula (IV) or its salt (e.g., hydrochloride, sulfate) with Compound (III) in a suitable solvent (a single solvent or a solvent mixture).

When a salt is employed, the reaction may be performed after neutralization with a base. Examples of a base which may be employed are metal hydroxides (e.g., sodium hydroxide, potassium hydroxide and the like), metal carbonates (e.g., sodium carbonate, potassium carbonate and the like), metal acetates (sodium acetate, potassium acetate and the like), metal alkoxides (e.g., sodium methoxide, sodium ethoxide and the like), pyridine and the like, and the amount to be used is 1 to 3 equivalents, relative to a salt of Compound (IV), preferably 1 to 2 equivalents.

In this reaction, Compound (IV) can be used in an amount of 1 equivalent or more, relative to Compound (III), preferably 1 to 3 equivalents.

Examples of a solvent which can be employed are aromatic hydrocarbons (toluene, benzene, xylene and the like), saturated hydrocarbons (e.g., cyclohexane, hexane and the like), alcohols (e.g., methanol, ethanol, propanol and the like), ethers (e.g., tetrahydrofuran, dioxane and the like), acetic acid, water as well as a mixture thereof.

The reaction temperature may be 0 to 160° C., preferably 20 to 130° C. While the reaction time varies depending on reactants, a time of 0.5 to 90 hours may be sufficient.

A desired Compound (Ia) thus obtained may be purified by a standard method (e.g., column chromatography, recrystallization and the like).

Compound (III) employed as a starting material in this reaction may be prepared by a method described in Reference Example 1 discussed later in this specification or an analogous method.

A hydroxylamine derivative or a hydrazine derivative represented by Formula (IV) is known per se, or, may be prepared by a known method similar to that described in Methoden der Organischen Chemie, Vol.X/1 and X/2 by Houben-Weyl.

[Route 2]

(Scheme 2)

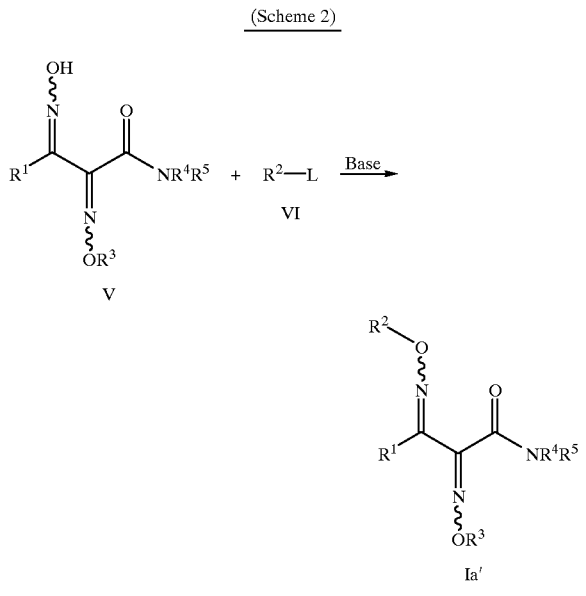

[Route 3]

(Scheme 3)

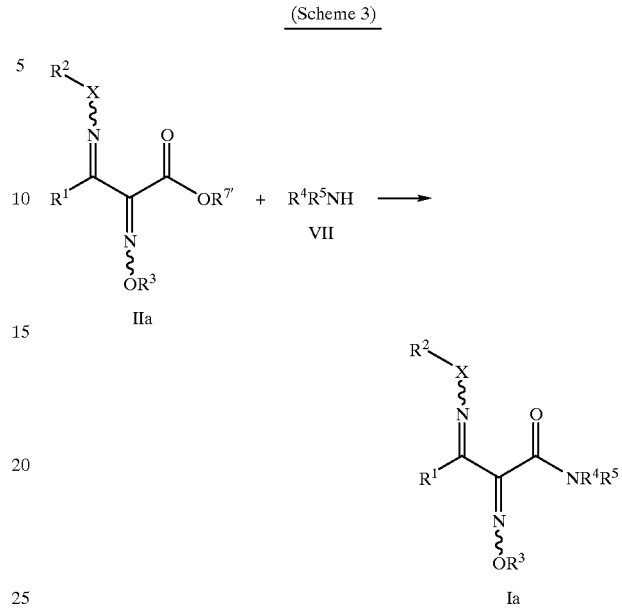

wherein L represents a halogen atom (e.g., chlorine atom, bromine atom and the like), an alkylsulfonyloxy (e.g., methylsulfonyloxy, ethylsulfonyloxy and the like) or an arylsulfonyloxy which may be substituted by a halogen atom or a lower alkyl (e.g., benzenesulfonyloxy, p-toluenesulfonyloxy, m-toluenesulfonyloxy, o-toluenesulfonyloxy and the like), and other radicals are defined as described above.

Thus, a compound according to the present invention represented by Formula (Ia') can be prepared by reacting Compound (V) and Compound (VI) in the presence of a base in a suitable solvent (a single solvent or a solvent mixture).

In this reaction, Compound (VI) can be used in an amount of 1 equivalent or more, relative to Compound (V), preferably 1 to 2 equivalents.

Examples of a base which may be employed are metal hydroxides (e.g., sodium hydroxide, potassium hydroxide and the like), metal hydrides (e.g., sodium hydride, potassium hydride and the like), metal alkoxides (e.g.,سodium methoxide, sodium ethoxide, potassium t-butoxide and the like), metal carbonates (e.g., sodium carbonate, potassium carbonate and the like) and the like, and the amount to be used is 1 equivalent or more, relative to Compound (V), preferably 1 to 2 equivalents.

Examples of a solvent which can be employed are N,N-dimethylformamide (DMF), dimethylsulfoxide (DMSO), aromatic hydrocarbons (toluene, benzene, xylene and the like), saturated hydrocarbons (e.g., cyclohexane, hexane and the like), ethers (e.g., tetrahydrofuran, dioxane and the like), ketones (e.g., acetone, methylethylketone and the like), water as well as a mixture thereof.

The reaction temperature may be −30 to 150° C., preferably −10 to 100° C. While the reaction time varies depending on reactants, a time of 0.5 to 90 hours may be sufficient.

A desired Compound (Ia') thus obtained may be purified by a standard method (e.g., column chromatography, recrystallization and the like).

Compound (V) employed as a starting material in this reaction may be prepared by a method described in WO 96/11183 or an analogous method.

wherein $R^{7\prime}$ represents an alkyl and other radicals are defined as described above.

Thus, a compound according to the present invention represented by Formula (Ia) can be prepared by reacting Compound (IIa) and Compound (VII) in the presence or absence of a suitable solvent (a single solvent or a solvent mixture).

In this reaction, Compound (VII) can be used in an amount of 1 equivalent or more, relative to Compound (IIa), preferably 1 to 30 equivalents.

Examples of a solvent which can be employed are hydrocarbons (e.g., benzene, toluene, xylene and the like), halogenated hydrocarbons (e.g., chloroform, 1,2-dichloroethane and the like), ethers (e.g., tetrahydrofuran, dioxane and the like), alcohols (e.g., methanol, ethanol, n-propanol, isopropanol and the like), N,N-dimethylformamide (DMF), dimethylsulfoxide (DMSO), saturated hydrocarbons (e.g., cyclohexane, hexane and the like), nitriles (e.g., acetonitrile and the like), water as well as a mixture thereof.

The reaction temperature may be −30 to 160° C., preferably −10 to 120° C. While the reaction time varies depending on reactants, a time of 0.5 to 120 hours may be sufficient.

A desired Compound (Ia) thus obtained may be purified by a standard method (e.g., column chromatography, recrystallization and the like).

Compound (IIa) employed as a starting material in this reaction may be prepared via Route 4 and Route 5 shown below.

[Route 4]

(Scheme 4)

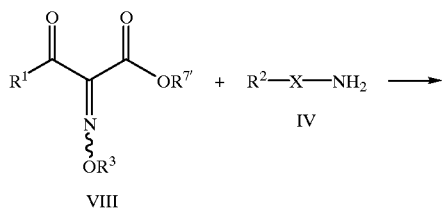

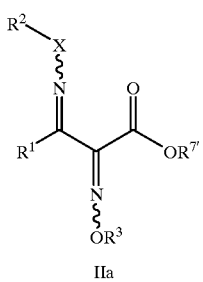

IIa wherein the radicals are defined as described above.

Thus, a compound represented by Formula (IIa) can be prepared by reacting Compound (VII) and Compound (IV) in a suitable solvent (a single solvent or a solvent mixture) similarly as in Scheme 1 described above.

A desired Compound (IIa) thus obtained may be purified by a standard method (e.g., column chromatography, recrystallization and the like).

Compound (VIII) employed as a starting material in this reaction may be prepared by a method described in Reference Example 2 discussed later in this specification or an analogous method.

[Route 5]

(Scheme 5)

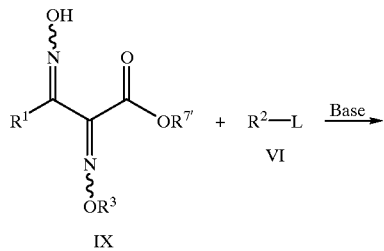

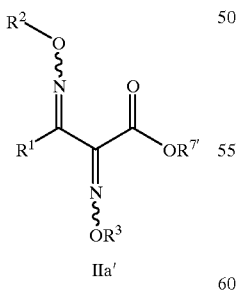

IIa' wherein the radicals are defined as described above.

Thus, a compound represented by Formula ((IIa') can be prepared by reacting Compound (IX) and Compound (VI) in the presence of a base in a suitable solvent (a single solvent or a solvent mixture) similarly as in Scheme 2 described above.

A desired Compound (IIa') thus obtained may be purified by a standard method (e.g., column chromatography, recrystallization and the like).

Compound (IX) employed as a starting material in this reaction may be prepared by a method described in WO96/11183 or an analogous method.

[Route 6]

(Scheme 6)

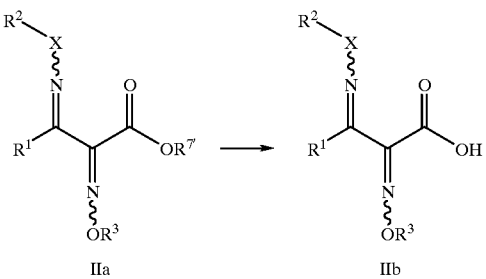

IIa    IIb wherein the radicals are defined as described above.

Thus, a compound represented by Formula (IIb) can be prepared by reacting an acid or a base with Compound (IIa) in a suitable solvent.

Example of an acid which may be employed are hydrochloric acid, hydrobromic acid, trifluoroacetic acid, p-toluenesulfonic acid and the like, and each may be used in an amount of 0.1 equivalent or more, relative to Compound (IIa), preferably 0.1 to 3 equivalents.

Examples of a base which may be employed are sodium hydroxide, potassium hydroxide, and the like, and each may be used in an amount of 1 equivalent or more, preferably 1 to 3 equivalents.

Examples of a solvent which can be employed are hydrocarbons (e.g., benzene, toluene, xylene and the like), halogenated hydrocarbons (e.g., chloroform, 1,2-dichloroethane and the like), ethers (e.g., tetrahydrofuran, dioxane and the like), alcohols (e.g., methanol, ethanol, n-propanol, isopropanol and the like), water as well as a mixture thereof.

The reaction temperature may be 0 to 150° C., preferably 20 to 100° C. The reaction time is generally 15 minutes to 100 hours.

A desired Compound (IIb) thus obtained may be purified by a standard method (e.g., column chromatography, recrystallization and the like).

A compound represented by Formula (II):

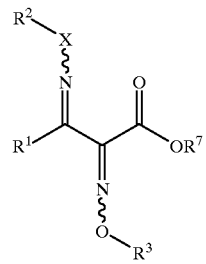

wherein the radicals are defined as described above, consisting of Compound (IIa) and Compound (IIb) obtained in Scheme 4, Scheme 5 and Scheme 6 described above, is a novel compound, and encompassed in the present invention.

(Scheme 7)

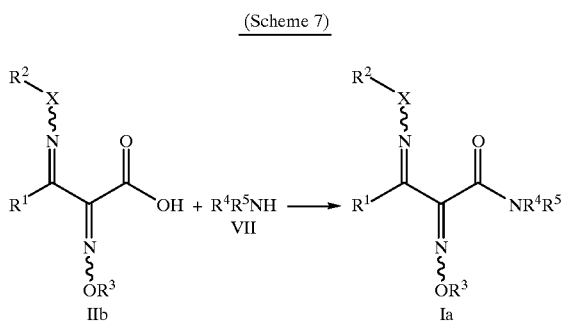

wherein the radicals are defined as described above.

Thus, a compound represented by Formula (Ia) can be prepared by reacting Compound (IIb) and Compound (VII) in the presence of a suitable condensing agent in a suitable solvent (a single solvent or a solvent mixture).

In this reaction, Compound (VII) may be used in an amount of 1 equivalent or more, relative to Compound (IIb), preferably 1 to 5 equivalents.

Examples of a condensing agent are N,N'-dicyclohexylcarbodiimide, 1,1'-carbonyldiimidazole, diphenylphosphoric acid azide, diethylphosphoric acid cyanide, ethyl chlorocarbonate, isopropyl chlorocarbonate and the like, and each may be used in an amount of 1 equivalent or more, relative to Compound (IIb) preferably 1 to 3 equivalents.

An organic base such as triethylamine, diisopropylethylamine, pyridine and the like, or an inorganic base such as sodium hydroxide, potassium hydroxide may be used in an amount of 1 to 5 equivalents or more, relative to Compound (IIb), preferably 1 to 2 equivalents.

Examples of a solvent which can be employed are hydrocarbons (e.g., benzene, toluene, xylene and the like), halogenated hydrocarbons (e.g., chloroform, 1,2-dichloroethane and the like), ethers (e.g., tetrahydrofuran, dioxane and the like), alcohols (e.g., methanol, ethanol, n-propanol, isopropanol and the like), N,N-dimethylformamide (DMF), dimethylsulfoxide (DMSO), saturated hydrocarbons (e.g., cyclohexane, hexane and the like), nitrites (e.g., acetonitrile and the like) as well as a mixture thereof.

The reaction temperature may be −30 to 100° C., preferably −20 to 80° C. While the reaction time varies depending on reactants, a time of 0.5 to 120 hours may be sufficient.

A desired Compound (Ia) thus obtained may be purified by a standard method (e.g., column chromatography, recrystallization and the like).

[Route 7]

(Scheme 8)

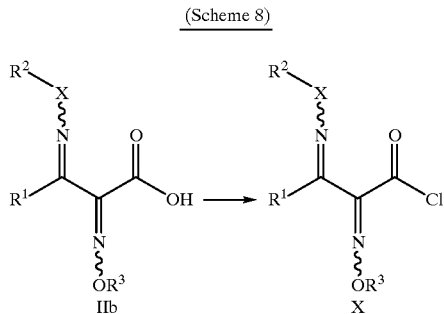

wherein the radicals are defined as described above.

Thus, a compound represented by Formula (X) can be prepared by chlorinating Compound (IIb) in a suitable solvent (a single solvent or a solvent mixture).

Examples of a chlorinating agent are thionyl chloride, oxalyl chloride, phosphorus oxychloride, phosphorus pentachloride, carbon tetrachloride-triphenylphosphine and the like, and each may be used in an amount of 1 to 5 equivalents, relative to Compound (IIb), preferably 1 to 2 equivalents.

A small amount of N,N-dimethylformamide (DMF) may be used as a reaction catalyst.

Examples of a solvent which can be employed are hydrocarbons (e.g., benzene, toluene, xylene and the like), halogenated hydrocarbons (e.g., chloroform, 1,2-dichloroethane and the like), ethers (e.g., tetrahydrofuran, dioxane and the like), nitrites (e.g., acetonitrile and the like) as well as a mixture thereof.

The reaction temperature may be −20 to 120° C., preferably 0 to 100° C. While the reaction time varies depending on reactants, a time of 0.5 to 60 hours may be sufficient.

A desired Compound (X) thus obtained may be used in the subsequent step as a reaction solution or a crude product, or after being purified by a standard method (e.g., distillation, crystallization and the like).

(Scheme 9)

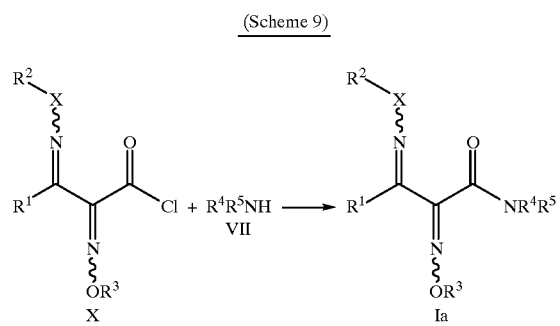

wherein the radicals are defined as described above.

Thus, a compound represented by Formula (Ia) can be prepared by reacting Compound (X) and Compound (VII) in a suitable solvent (a single solvent or a solvent mixture).

In this reaction, Compound (VII) may be used in an amount of 1 equivalent or more, relative to Compound (X), preferably 1 to 5 equivalents.

An organic base such as triethylamine, diisopropylethylamine, pyridine and the like, or an inorganic base such as sodium hydroxide, potassium hydroxide may be used in an amount of 1 to 5 equivalents or more, relative to Compound (X), preferably 1 to 2 equivalents.

Examples of a solvent which can be employed are hydrocarbons (e.g., benzene, toluene, xylene and the like), halogenated hydrocarbons (e.g., chloroform, 1,2-dichloroethane and the like), ethers (e.g., tetrahydrofuran, dioxane and the like), nitrites (e.g., acetonitrile and the like), water as well as a mixture thereof.

The reaction temperature may be −30 to 100° C., preferably −10 to 80° C. While the reaction time varies depending on reactants, a time of 0.5 to 24 hours may be sufficient.

A desired Compound (Ia) thus obtained may be purified by a standard method (e.g., column chromatography, recrystallization and the like).

[Route 8]

(Scheme 10)

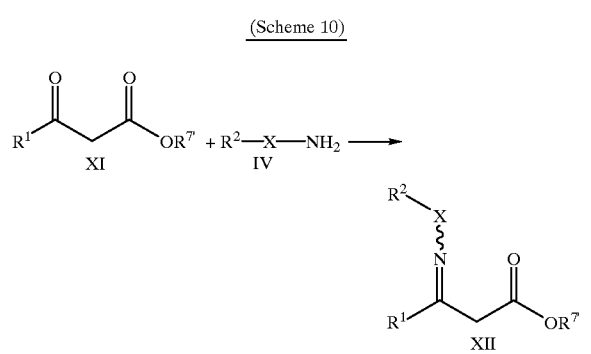

wherein the radicals are defined as described above.

Thus, a compound represented by Formula (XII) can be prepared by reacting Compound (IV) with Compound (XI) in a suitable solvent (a single solvent or a solvent mixture) similarly as in Scheme 1 described above.

A desired Compound (XII) thus obtained may be used in the subsequent step, as a reaction solution or a crude product, or after being purified by a standard method (e.g., distillation, crystallization and the like).

Compound (XI) employed as a starting material in this reaction is known per se, or may be prepared by a known method similar to that described in Synthesis, page 290 (1993).

(Scheme 11)

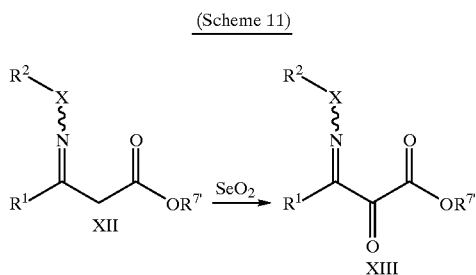

wherein the radicals are defined as described above.

Thus, a compound represented by Formula (XIII) can be prepared by reacting Compound (XII) with selenium dioxide in a suitable solvent (a single solvent or a solvent mixture).

In this reaction, selenium dioxide may be used in an amount of 1 equivalent or more, relative to Compound (XII), preferably 1 to 3 equivalents.

Examples of a solvent which can be employed are aromatic hydrocarbons (toluene, benzene, xylene and the like), halogenated aromatic hydrocarbons (e.g., chlorobenzene, dichlorobenzene and the like), saturated hydrocarbons (e.g., cyclohexane, hexane and the like), alcohols (e.g., methanol, ethanol, propanol and the like), ethers (e.g., tetrahydrofuran, dioxane and the like), acetic acid, water as well as a mixture thereof.

The reaction temperature may be 30 to 180° C., preferably 50 to 160° C. While the reaction time varies depending on reactants, a time of 0.5 to 50 hours may be sufficient.

A desired Compound (XIII) thus obtained may be used in the subsequent step, as a reaction solution or a crude product, or after being purified by a standard method (e.g., distillation, crystallization and the like).

(Scheme 12)

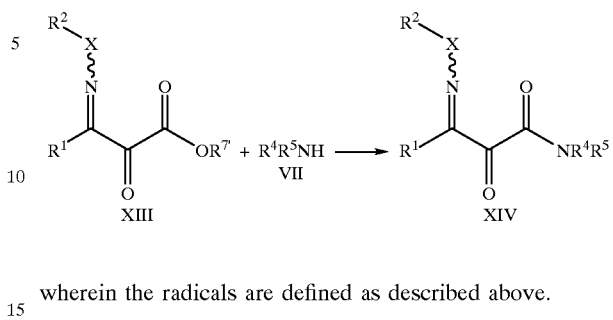

wherein the radicals are defined as described above.

Thus, a compound represented by Formula (XIV) can be prepared by reacting Compound (XIII) and Compound (VII) in the presence or absence of a suitable solvent (a single solvent or a solvent mixture) similarly as in Scheme 3 described above.

A desired Compound (XIV) thus obtained may be used in the subsequent step, as a reaction solution or a crude product, or after being purified by a standard method (e.g., distillation, crystallization and the like).

(Scheme 13)

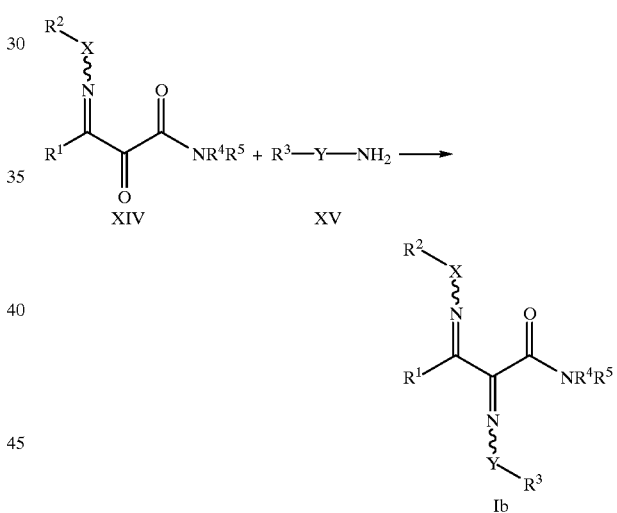

wherein the radicals are defined as described above.

Thus, a compound represented by Formula (Ib) can be prepared by reacting a hydroxylamine derivative or a hydrazine derivative represented by Formula (XV) or its salt (e.g., hydrochloride, sulfate) and Compound (XIV) in a suitable solvent (a single solvent or a solvent mixture) similarly as in Scheme 1 described above.

A desired Compound (Ib) thus obtained may be purified by a standard method (e.g., column chromatography, recrystallization and the like).

A hydroxylamine derivative or a hydrazine derivative represented by Formula (XV) is known per se, or, may be prepared by a known method similar to that described in Methoden der Organischen Chemie, Vol.X/1 and X/2 by Houben-Weyl.

[Route 9]

(Scheme 14)

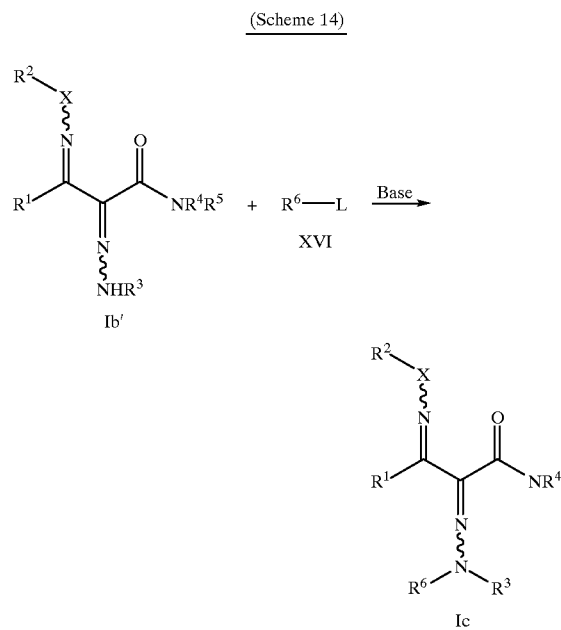

wherein the radicals are defined as described above.

Thus, a compound represented by Formula (Ic) can be prepared by reacting Compound (Ib') and Compound (XVI) in the presence of a base in a suitable solvent (a single solvent or a solvent mixture).

In this reaction, Compound (XVI) may be used in an amount of 1 equivalent or more, relative to Compound (Ib'), preferably 1 to 10 equivalents.

Examples of a base which may be employed are metal hydroxides (e.g., sodium hydroxide, potassium hydroxide and the like), metal hydrides (e.g., sodium hydride, potassium hydride and the like), metal alkoxides (e.g., sodium methoxide, sodium ethoxide, potassium t-butoxide and the like), metal carbonates (e.g., sodium carbonate, potassium carbonate and the like), pyridine, triethylamine and the like, and the amount to be used is 1 equivalent or more, relative to Compound (Ib'), preferably 1 to 20 equivalents.

Examples of a solvent which can be employed are N,N-dimethylformamide (DMF), dimethylsulfoxide (DMSO), aromatic hydrocarbons (toluene, benzene, xylene and the like), saturated hydrocarbons (e.g., cyclohexane, hexane and the like), ethers (e.g., tetrahydrofuran, dioxane and the like), ketones (e.g., acetone, methylethylketone and the like), water as well as a mixture thereof.

The reaction temperature may be −30 to 150° C., preferably −10 to 100° C. While the reaction time varies depending on reactants, a time of 0.1 to 90 hours may be sufficient.

A desired Compound (Ic) thus obtained may be purified by a standard method (e.g., column chromatography, recrystallization and the like).

[Route 10]

(Scheme 15)

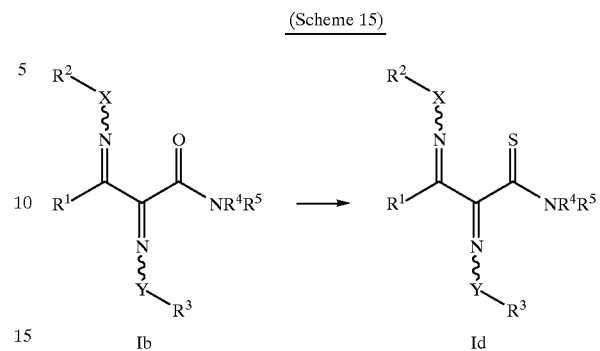

wherein the radicals are defined as described above.

Thus, a compound represented by Formula (Id) can be prepared by reacting Compound (Ib) with a sulfurizing agent in a suitable solvent (a single solvent or a solvent mixture).

As a sulfurizing agent, phosphorus pentasulfide or Lawson's reagent may be mentioned, and each is used in an amount of 1 to 5 equivalents, relative to Compound (Ib), preferably 1 to 2 equivalents.

Examples of a solvent which can be employed are hydrocarbons (benzene toluene, xylene and the like), pyridine as well as a mixture thereof.

The reaction temperature may be 10 to 200° C., preferably 60 to 150° C. While the reaction time varies depending on reactants, a time of 0.5 to 48 hours may be sufficient.

A desired Compound (Id) thus obtained may be purified by a standard method (e.g., column chromatography, recrystallization and the like).

Compound (I) according to the present invention or its salt or hydrate is effective against pathogenic microbes (fungi) and soil fungi on crop plants or their seeds such as rice, wheat, barley, rye, corn, millet, foxtail millet, buckwheat, soybean, redbean, peanut, and the like, fruit trees such as citrus fruits, grape, apple, pear, peach and the like, or vegetables such as cucumber, eggplant, tomato, pumpkin, kidney bean and the like. The compound of this invention shows a potent fungicidal activity particularly against a rice blight microorganism (*Pyricularia oryzae*), a sheath blight microorganism (*Rhizoctonia solani*), a wheat powdery mildew microorganism (*Erysiphe graminis*), a cucumber mildew microorganism (*Sphaerotheca fuliginea*), a tobacco mildew microorganism (*Erysiphe cichoracearum*), a potato late blight microorganism (*Phylophthora infestans*), a cucumber downy mildew microorganism (*Pseudoperonospora cubensis*), a soybean downey mildew microorganism (*Peronospora manshurica*), a grape downy mildew microorganism (*Plasaopara viticola*), a grey mold microorganism (*Botrytis cinerea*) of vegetables, grape and the like, a cucumber seedle damping off microorganism (*Pythium aphanidermatum*), a sclerotium disease microorganism (*Sclerotinia sclerotiorum*) of buckwheat, soybean, rape and the like, a stem rot microrganism (*Corticium rolfsii*) of soybean, red bean, potato, peanut and the like, a wheat eyespot disease microorganism (*Pseudocercosporella herpotrichoides*) and the like. Therefore, Compound (I) according to the present invention or its salt or hydrate is useful as a fungicide, particularly as an agricultural fungicide.

Application of Compound (I) according to the present invention or a salt or a hydrate thereof as agrochemicals may be to a plant may be performed by any conventional procedure such as atomizing, scattering or spreading of an active compound, or, alternatively, the application may be performed by mans of a treatment of a seed of a plant, a soil where a plant grows, a soil for seeding, a paddy field or a water for perfusion with an active compound. Application may be performed before or after an infection with a phytopathogenic microorganism.

A compound according to the present invention can be used as an agrochemical formulation suitable for an agricultural fungicide, such as a solution, a wettable powder, an emulsion, a suspension, a concentrated liquid preparation, a tablet, a granule, an aerosol, a powder, a paste, a fumigant and the like.

Such formulation can be prepared in a conventional manner by mixing at least one compound according to the present invention with an appropriate solid or liquid carrier and, if necessary, an appropriate adjuvant (e.g., surfactant, spreader, dispersant, stabilizer and the like) for improving the dispersibility and other properties of an active ingredient.

Examples of a solid carrier or a diluent are a botanical material (e.g., flour, tobacco stalk powder, soybean powder, walnut-shell powder, vegetable powder, saw dust, bran, bark powder, cellulose powder, vegetable extract residue and the like), a fibrous material (e.g., paper, corrugated cardboard, old rag and the like), an artificial plastic powder, a clay (e.g., kaolin, bentonite, fuller's earth and the like), talc, other inorganic materials (e.g., pyrophyllite, sericite, pumice, sulfur powder, activated carbon and the like), a chemical fertilizer (e.g., ammonium sulfate, ammonium phosphate, ammonium nitrate, urea, ammonium chloride and the like) and the like.

Examples of a liquid carrier or a diluent are water, alcohols (e.g., methanol, ethanol and the like), ketones (e.g., acetone, methyl ethyl ketone and the like), ethers (e.g., diethylether, dioxane, cellosolve, tetrahydrofuran), aromatic hydrocarbons (e.g., benzene, toluene, xylene, methylnahthalene and the like), aliphatic hydrocarbons (e.g., gasoline, kerosene, lamp oil and the like), esters, nitriles, acid amides (e.g. dimethylformamide, dimethylacetamide and the like), halogenated hydrocarbons (e.g., dichloroethane, carbon tetrachloride and the like) and the like.

Examples of a surfactant are an alkyl sulfuric, an alkyl ester, an alkylaryl sulfuric ester, a polyethylene glycol ether, a polyhydric alcohol ester and the like. Examples of a spreader or a dispersant are casein, gelatin, starch powder, carboxymethylcellulose, gum arabic, alginic acid, lignin, bentonite, molasses, polyvinyl alcohol, pine oil, agar and the like. Examples of a stabilizer are PAP (a mixture of isopropylphosphate), tricresyl phosphate (TCP), tall oil, an epoxidized oil, a surfactant, a fatty acid and its ester and the like.

A composition according to the present invention may contain other fungicides, insecticides, herbicides or fertilizers in addition to the ingredients listed above.

In general, a composition described above contains at least one compound of Formula (I) of the present invention or its salt or hydrate in a concentration of 0.1 to 95% by weight, preferably 1.0 to 80% by weight. The composition can be used as it is or in a diluted form, and about 1.0 g to 5 kg/ha, preferably about 10 g to 1.0 kg/ha, of a compound according to the present invention is used in a concentration of normally about 1 to 5,000 ppm, preferably about 10 to 1,000 ppm.

A compound of Formula (I) according to the present invention or its salt or hydrate is useful as a prophylactic or therapeutic agent in mammals including human against tachykinin receptor antagonism-related inflammatory diseases, gastrointestinal diseases, vomiting, dysuria, pain, migraine, neuralgia, Alzheimer's disease, immunopotentiation or immunosuppression-related diseases, rheumatoid diseases, allergic diseases and the like.

A compound of Formula (I) according to the present invention or its salt or hydrate may be administered as a pharmaceutical via any route such as oral, topical and parenteral routes.

A compound according to the present invention may be used as a pharmaceutical formulation for a medical use such as a powder, a fine granule, a granule, a tablet, a capsule, a solution for injection and the like.

Such formulation may be obtained by an ordinary process in which at least one of the compounds according to the present invention is mixed with a suitable solid or liquid carrier, and, if desired, an excipient (e.g., starch, lactose, sugar, potassium carbonate, calcium phosphate and the like), a binder (e.g., starch, gum arabic, carboxymethylcellulose, hydroxypropylcellulose, crystalline cellulose, alginic acid, gelatin, polyvinylpyrrolidone and the like), a glidant (e.g., stearic acid, magnesium stearate, calcium stearate, talc and the like), a disintegrant (e.g., potassium carboxymethylcellulose, talc and the like), a diluent (e.g., physiological saline and the like).

In general, a pharmaceutical described above may be given in a dose which may vary depending on the administration route as well as the symptoms and the ages of the subjects, and the daily dose, as at least one Compound (I) according to the present invention or its salt or hydrate, may be about 0.001 mg to 50 mg, preferably about 0.01 mg to 10 mg, per kg body weight, which may be given as being divided to 3 dosages or less a day.

EXAMPLES

The following Examples and Test Examples further illustrate the present invention in detail, but are not to be construed to limit the scope thereof The $^1$H-NMR (CDCl$_3$) data in Examples and Tables shown later were determined at 270 MHz in CDCl$_3$ using tetramethylsilane as an internal standard and indicated in δ values (ppm). The coupling constants (J) are indicated in Hz. In the data, s is a singlet, d is a doublet, t is a triplet, q is a quartet, AB is a ABq type quartet, sept is a septet and m is a multiplet.

Reference Example 1

Synthesis of 2-methoxyimino-N,N-dimethylacetoacetamide 18.04 g (0.2 mol) of a 50% aqueous solution of dimethylamine in 10 ml toluene was cooled in an ice bath and combined with 8.41 g (0.1 mol) of a diketene in 20 ml of toluene and stirred for 1 hour at room temperature. After distilling water off azeotropically, 200 ml of ethyl acetate was added and the mixture was dried over with anhydrous sodium sulfate to distill the solvent off. To the residue thus obtained, 7.63 g (0.105 mol) of sodium nitrite was added and the mixture was cooled in an ice bath and then 10 ml (0.12 mol) of a concentrated hydrochloric acid was added dropwise. After stirring for 0.5 hour at room temperature, the reaction mixture was cooled again in an ice bath, and 5.42 g (0.13 mol) of sodium hydroxide was added. The solution thus obtained was added to a solution of 18.92 g (0.15 mol) of dimethyl sulfate and 1.61 g (0.05 mol) of tetrabutylammonium bromide in 50 ml of toluene dropwise while cooling with an ice, and the mixture was stirred for 4 hours at room temperature. The reaction mixture was extracted four times with 150 ml of ethyl acetate and dried over with anhydrous magnesium sulfate, and then the solvent was distilled off, and finally the residue thus obtained was purified by a column chromatography on a silica gel (n-hexane/ethyl acetate) to obtain 13.46 g (yield: 78%) of 2-methoxyimino-N,N-dimethylacetoacetamide as a colorless crystal.

(Melting point: 73.5 to 75° C.)

Example 1

Synthesis of 2-methoxyimino-N,N-dimethyl-3-(N-methyl-N-phenylhydrazono)butyramide (Compound No.1-1)

1.0 g (5.8 mmol) of 2-methoxyimino-N,N-dimethylacetoacetamide was dissolved in 15 ml of ethanol and 0.5 ml of acetic acid, and 0.78 g (6.4 mmol) of N-methyl-N-phenylhydrazine was added and the mixture was stirred for 24 hours at room temperature. After distilling the solvent off, water was added and the mixture was extracted three times with 20 ml of diethylether. After washing with a dilute hydrochloric acid, water and a saturated aqueous sodium chloride, the mixture was dried over with anhydrous magnesium sulfate, and the solvent was distilled off, and finally the residue thus obtained was purified by a column chromatography on a silica gel (n-hexane/ethyl acetate) to obtain 1.38 g (yield: 86%) of 2-methoxyimino-N,N-dimethy-3-(N-methyl-N-phenylhydrazono)butyramide as a yellow oil. $^1$H-NMR (CDCl$_3$) δ ppm:2.13(3H, s), 2.90(3H,s), 3.07(3H, s), 3.29 (3H, s), 3.99(3H,s), 6.90–7.02(3H, m), 7.33–7.29(2H, m).

Example 2

Synthesis of 3-(4-methylbenzyloxyimino)-2-methoxyimino-N,N-dimethylbutyramide (Compound No.C-376)

To a solution of 600 mg (3.2 mmol) of 3-hydroxyimino-2-methoxyimino-N,N-dimethylbutyramide in 20 ml of acetone, 500 mg (3.5 mmol) of 4-methylbenzylchloride and 660 mg (4.8 mmol) of potassium carbonate were added and the mixture was heated under reflux for 16 hours. The reaction mixture was combined with 30 ml of water and extracted three times with 30 ml of diethylether. After washing with water and a saturated aqueous sodium chloride, the mixture was dried over with anhydrous magnesium sulfate and then the solvent was distilled off. The residue thus obtained was purified by a column chromatography on a silica gel (n-hexane/ethyl acetate) to obtain 900 mg (yield: 96%) of 3-(4-methylbenzyloxyimino)-2-methoxyimino-N,N-dimethylbutyramide as a colorless crystal.

(Melting point: 68 to 69° C.)

Reference Example 2

Synthesis of methyl 2-benzyloxyiminoacetoacetate (1) Synthesis of methyl 2-hydroxyiminoacetoacetate To a solution of 46.45 g (0.4 mol) of methyl acetoacetate in 200 ml of diethylether, 30.4 g (0.44 mol) of sodium nitrite was added and the mixture was cooled in an ice bath and treated dropwise with 40 ml (0.48 mol) of a concentrated hydrochloric acid. After stirring for 1 hour at room temperature, 200 ml of water was added and the mixture was extracted three times with 200 ml of diethylether. After washing with water and a saturated aqueous sodium chloride followed by drying over with anhydrous magnesium sulfate, the solvent was distilled off to obtain 50.09 g (yield: 86%) of a crude methyl 2-hydroxyiminoacetoacetate as a pale yellow oil. (2) Synthesis of methyl 2-benzyloxyiminoacetoacetate To a solution of 15.0 g (103 mmol) of methyl 2-hydroxyiminoacetoacetate in 200 ml of acetone, 14.4 g (113 mmol) of benzyl chloride and 21.4 g (155 mmol) of potassium carbonate were added and the mixture was heated under reflux for 15 hours. The reaction mixture was combined with 200 ml of water and extracted three times with 200 ml of diethylether. After washing with water and a saturated aqueous sodium chloride followed by drying over with anhydrous magnesium sulfate, the solvent was distilled off. The residue thus obtained was purified by a column chromatography on a silica gel (n-hexane/ethyl acetate) to obtain 18.7 g (yield: 77%) of methyl 2-benzyloxyiminoacetoacetate as a colorless crystal.

(Melting point: 35 to 36° C.)

Example 3

Synthesis of methyl 2-benzyloxyimino-3-methoxyiminobutyrate (Compound No.x-10)

To a solution of 4.0 g (17 mol) of methyl 2-benzyloxyiminoacetoacetate in 50 ml of methanol, 1.56 g (18.7 mmol) of methoxyamine hydrochloride was added and the mixture was heated under reflux for 3 hours. After distilling the solvent off under reduced pressure, 50 ml of water was added and the mixture was extracted twice with 50 ml of diethylether and then washed with water and a saturated aqueous sodium chloride. The organic layer was dried over with anhydrous magnesium sulfate and the solvent was distilled off to obtain a residue, which was then purified by a column chromatography on a silica gel (n-hexane/ethyl acetate) to obtain 4.11 g (yield:91%) of methyl 2-benzyloxyimino-3-methoxyiminobutyrate as a colorless oil. $^1$H-NMR(CDCl$_3$) δ ppm:1.99(3H, s), 3.86(3H, s), 3.94(3H, s), 5.21(2H, s), 7.33(5H, m).

Example 4

Synthesis of 2-benzyloxyimino-3-methoxyiminobutyric acid (Compound No. z-10)

To a solution of 3.2 g (12.1 mmol) of methyl 2-benzyloxyimino-3-methoxyiminobutyrate in 50 ml of methanol, 1.01 g (24.2 mmol) of sodium hydroxide and 10 ml of water were added and the mixture was heated under reflux for 24 hours. After distilling the solvent off under reduced pressure and adding 50 ml of water, the mixture was washed with 50 ml of diethylether. The aqueous layer was made acidic by adding a concentrated hydrochloric acid, and then the mixture was extracted three times with 50 ml of diethylether. After washing with water and with a saturated aqueous sodium chloride, the organic layer was dried over with anhydrous magnesium sulfate and the solvent was distilled off to obtain 3.02 g (yield: 100% ) of 2-benzyloxyimino-3-methoxyiminobutyric acid as a white solid.

(Melting point: 88 to 89° C.)

Example 5

Synthesis of 2-benzyoxyimino-3-methoxyimino-N,N-dimethylbutyramide (Compound No.C-10)

To a solution of 0.9 g (3.6 mmol) of 2-benzyloxyimino-3-methoxyiminobutyric acid in 15 ml of toluene, 0.5 g (4.0 mmol) of thionyl chloride and one drop of N,N-dimethylformamide were added and the mixture was stirred for 1 hour at 60° C. After cooling with an ice, 5 ml of 50% dimethylamine solution was added and the mixture was stirred for 0.5 hour at room temperature. 30 ml of water was added and the mixture was extracted three times with 50 ml of diethylether. After washing with water and a saturated aqueous sodium chloride, the organic layer was dried over with anhydrous magnesium sulfate and the solvent was distilled off to obtain a residue, which was then purified by a column chromatography on a silica gel (n-hexane/ethyl acetate) to obtain 0.53 g (yield: 53%) of 2-benzyloxyimino-3-methoxyimino-N,N-dimethylbutyramide as a colorless oil.

¹H-NMR(CDCl₃) δ ppm:2.02(3H, s), 2.74(3H, s), 3.00 (3H, s), 3.92(3H, s), 5.19(2H, s), 7.33(5H,m).

Example 6

Synthesis of 4-(3-benzyloxyimino-2-(4-methoxybenzylhydrazono)valeryl)morpholine (Compound No. n-794)

(1) Synthesis of methyl 3-benzyloxyiminovalerate

To a solution of 26.03 g (0.2 mol) of methyl propionylacetate in 300 ml of methanol, 100 ml of water and 35.12 g (0.22 mol) of benzyloxyamine hydrochloride, 19.69 g (0.24 mol) of potassium acetate were added and the mixture was stirred for 15 hours at room temperature. After distilling methanol off under reduced pressure, followed by adding 200 ml of water and extracting three times with 200 ml of ethyl acetate, the mixture was washed with water and a saturated aqueous sodium chloride and then dried over with anhydrous magnesium sulfate. The solvent was distilled off under reduced pressure to obtain 47.06 g (yield: 100%) of a crude methyl 3-benzyloxyiminovalerate as a colorless oil.

(2) Synthesis of methyl 3-benzyloxyimino-2-oxovalerate.

To a solution of 47.06 g (0.2 mol) of methyl 3-benzyloxyiminovalerate in 150 ml of chlorbenzene, 24.41 g (0.22 mol) of selenium dioxide was added and the mixture was stirred for 8 hours at 120° C. After adding 200 ml of water and filtering through Celite, the filtrate was extracted three times with 200 ml of diethylether. After washing with water and a saturated aqueous sodium chloride followed by drying over with anhydrous magnesium sulfate, the solvent was distilled off under reduced pressure to obtain a residue, which was purified by a column chromatography on a silica gel (n-hexane/ethyl acetate) to obtain 31.15 g (yield 62%) of methyl 3-benzyloxyimino-2-oxovalerate as a colorless oil.

¹H-NMR(CDCl₃) δ ppm:1.04(3H, t, J=7.6), 2.52(2H, d, J=7.6), 3.86(3H, s), 5.29(2H, s), 7.36(5H, m).

(3) Synthesis of 4-(3-benzyloxyimino-2-oxyvaleryl) morpholine 10.0 g (0.04 mol) of methyl 3-benzyloxyimino-2-oxovalerate and 20 ml of morpholine were combined and the mixture was stirred for 3 hours at 100° C. After distilling the morpholine off under reduced pressure, 100 ml of water was added and the mixture was extracted three times with 100 ml of diethylether. After washing with water and a saturated aqueous sodium chloride followed by anhydrous magnesium sulfate, the solvent was distilled off under reduced pressure to obtain a residue, which was purified by a column chromatography on a silica gel (n-hexane/ethyl acetate) to obtain 6.78 g (yield: 56%) of 4-(3-benzyloxyimino-2-oxovaleryl)morpholine as a white solid.

¹H-NMR(CDCl₃) δ ppm:1.07(3H, t, J=7.6), 2.56(2H, q, J=7.6), 3.01(2H, t, J=4.9), 3.39(2H,t, J=4.9), 3.60–3.70(4H, m), 5.29(2H, s), 7.36(5H, m).

(4) Synthesis of 4-(3-benzyloxyimino-2-(4-methoxybenzylhydrazono)valeryl)morpholine 1.0 g (3.3 mmol) of 4-(3-benzyloxyimino-2-oxovaleryl) morpholine was dissolved in 20 ml of 2-propanol and 1.24 g (6.6 mmol) of 4-methoxybenzylhydrazine hydrochloride, 1.08 g (13.2 mmol) of sodium acetate and 1 ml of acetic acid were added and the mixture was refluxed for 15 hours. After distilling the solvent off under reduced pressure, 20 ml of water was added and the mixture was extracted three times with 30 ml of diethylether. After washing with 1N aqueous hydrochloric acid, water, a saturated aqueous sodium bicarbonate, water and then a saturated aqueous sodium chloride followed by drying over with anhydrous magnesium sulfate, the solvent was distilled off under reduced pressure to obtain a residue, which was purified by a column chromatography on a silica gel (n-hexane/ethyl acetate) to obtain 1.19 g (yield: 83%) of 4-(3-benzyloxyimino-2-(4-methoxybenzylhydrazono)valeryl)morpholine as a yellow oil.

¹H-NMR(CDCl₃) δ ppm: 1.08(3H, t, J=7.6), 2.63(2H, q, J=7.6), 2.94(2H, t, J=4.9), 3.29(2H,t, J=4.9), 3.59(4H, brs), 3.79(3H, s), 4.38(2H, d, J=4.9), 5.10(2H, s), 6.15(1H, t, J=4.9), 6.84(2H, d, J=8.5), 7.19(2H, d, J=8.5), 7.32(5H, m).

Example 7

Synthesis of 4-(3-benzyloxyimino-2-((4-methoxybenzyl) methylhydrazono)valeryl)morpholine (Compound No. o-794)

0.04 g (1.0 mmol) of 60% sodium hydride was suspended in 10 ml of N,N-dimethylformamide, and to this a solution of 0.40 g (0.91 mmol) of 4-(3-benzyloxyimino-2-(4-methoxybenzylhydrazono)valeryl)morpholine in 5 ml of N,N-dimethylformamide and 0.19 g (0.13 mmol) of methyl iodide were added and the mixture was stirred for 1 hour at room temperature. 20 ml of water was added and the mixture was extracted three times with 20 ml of diethylether. After washing with water and a saturated aqueous sodium chloride followed by drying over with anhydrous magnesium sulfate, the solvent was distilled off to obtain a residue, which was purified by a column chromatography on a silica gel (n-hexane/ethyl acetate) to obtain 0.35 g (yield: 85%) of 4-(3-benzyloxyimino-2-((4-methoxybenzyl) methylhydrazono)valeryl) as a yellow oil.

¹H-NMR(CDCl₃) δ ppm:1.07(3H, t, J=7.6), 2.65(2H, q, J=7.6), 2.84(3H, s), 2.92–2.98(2H, m), 3.23–3.69(6H, m), 3.79(3H, s), 4.32(1H, d, J=14.3), 4.36(1H, d, J=14.3), 5.05 (1H, d, J=12.5), 5.15(1H, d, J=12.5), 6.84(2H, d, J=8.5), 7.18(2H, d, J=8.5), 7.33(5H, m).

Examples of the compounds represented by Formula (I) and (II) obtainable by the same manner as that in Examples described above are the following compound group A to Z, and a to w and x to z, and examples of combination of the substituents R¹, R² and R³ of the compound groups A to Z and a to z are shown in Tables 1 to 70. The physical data of the compounds are shown in Tables 71 to 83. The physical data of the compound obtained in the above Examples are also listed in the Tables. "No." in each Table represents a compound number, and, for example, "A-176" means a compound which is included in compound group A and which has the combination of the substituent designated by No. 176.

A

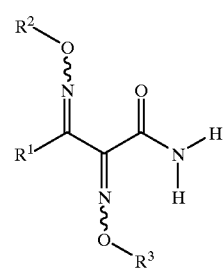

-continued
B
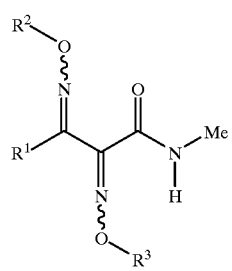
C
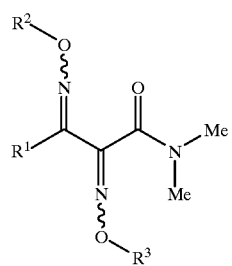
D
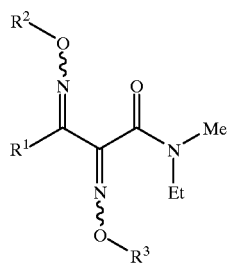
E
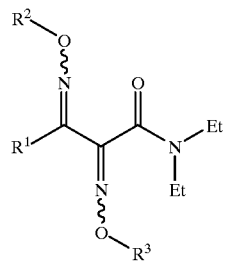
F
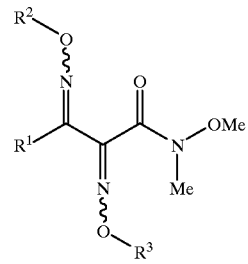
G
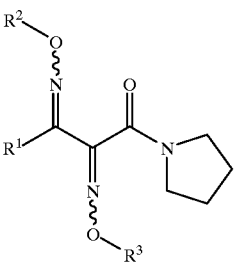
-continued
H
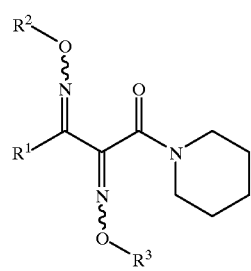
I
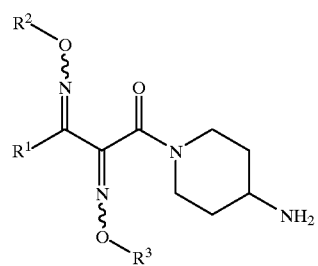
J
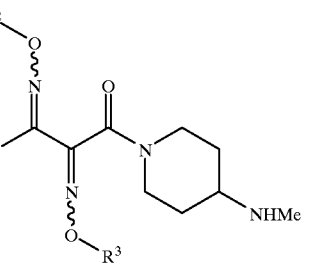
K
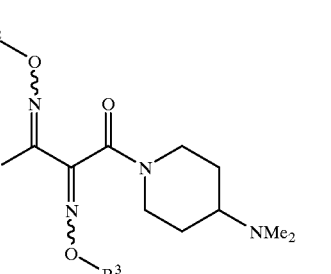
L
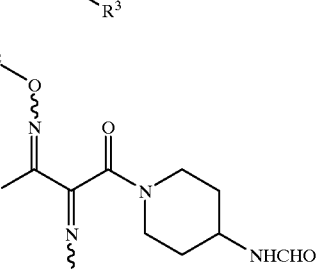
M
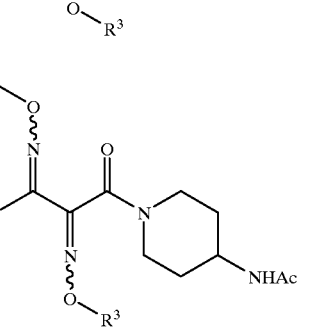

N
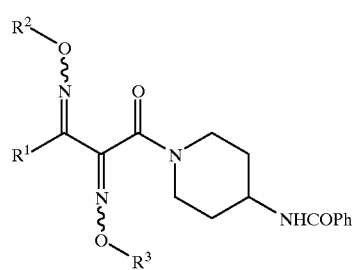
O
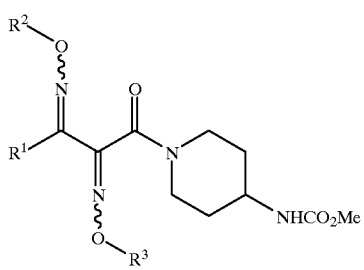
P
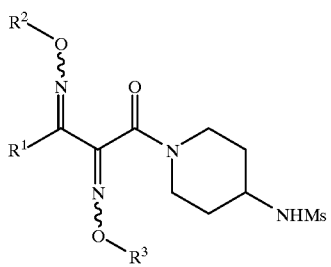
Q
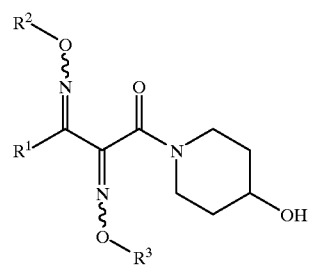
R
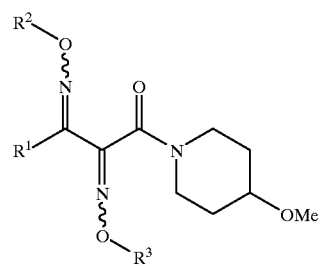
S
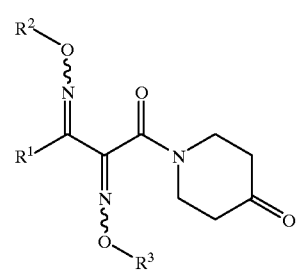
T
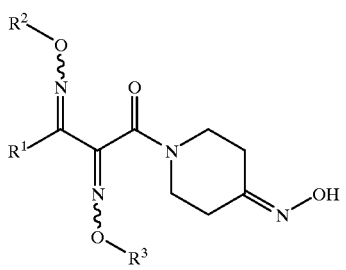
U
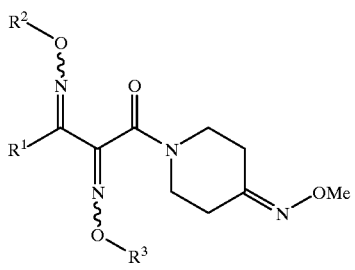
V
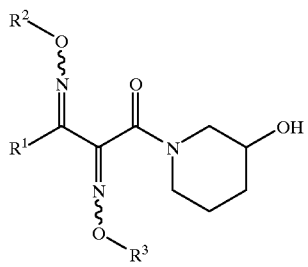
W
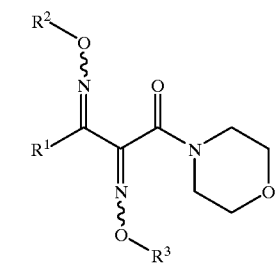
X
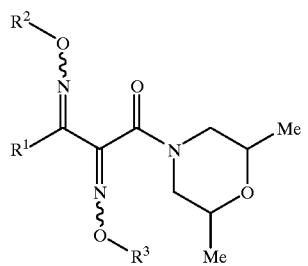
Y
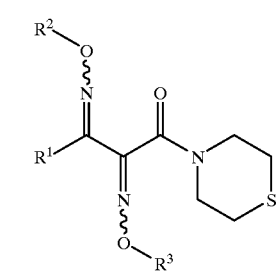

-continued
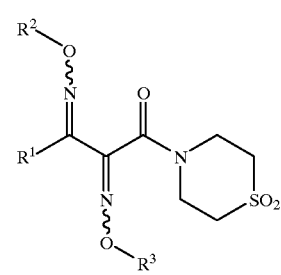
z
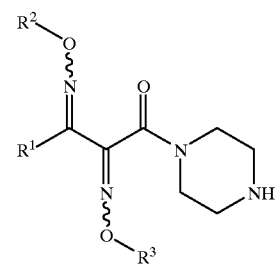
a
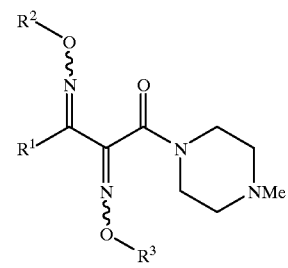
b
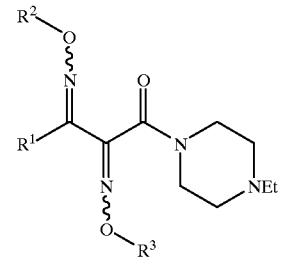
c
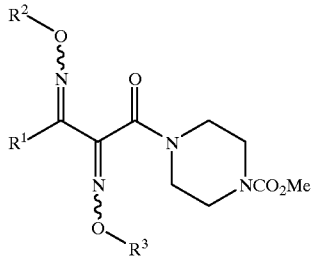
d
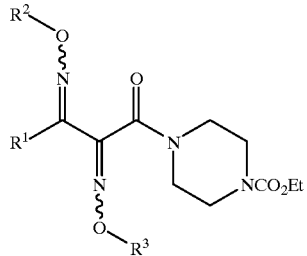
e
-continued
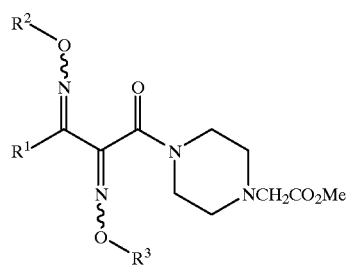
f
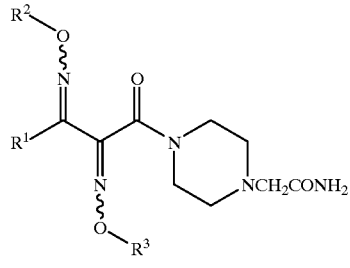
g
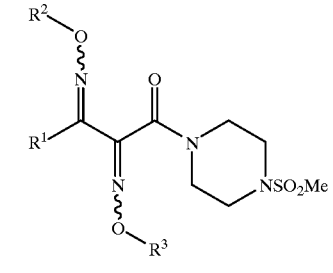
h
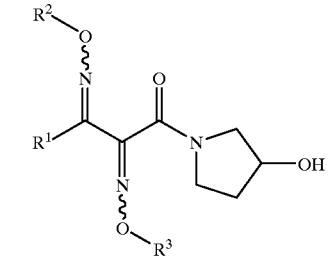
i
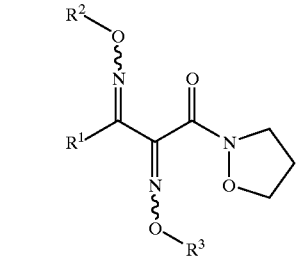
j
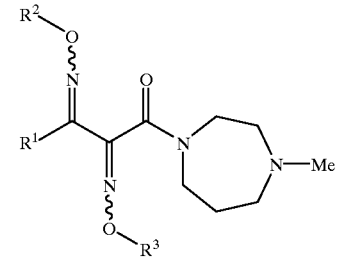
k -continued
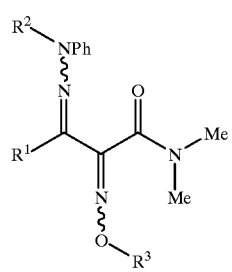
l
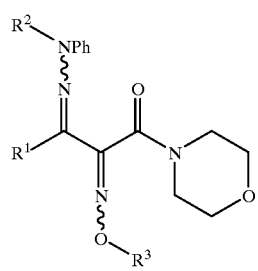
m
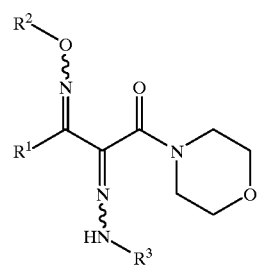
n
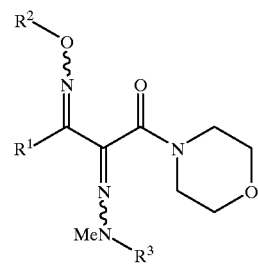
o
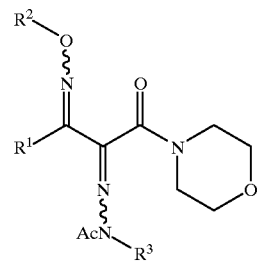
p
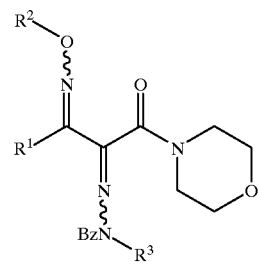
q
-continued
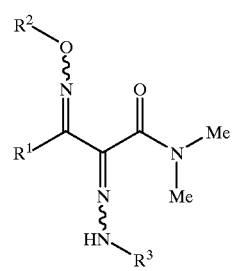
r
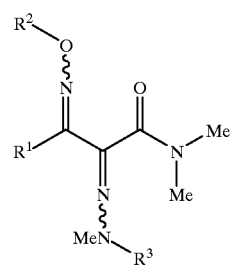
s
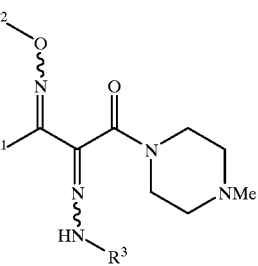
t
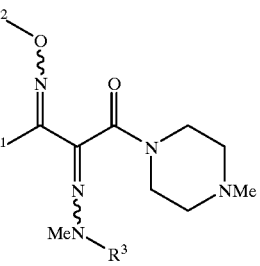
u
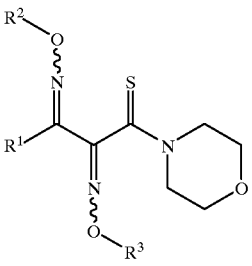
v
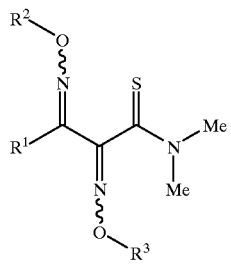
w -continued

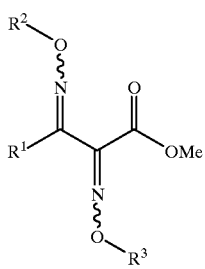

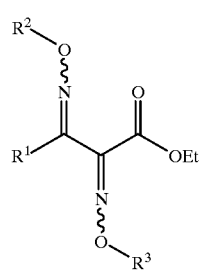

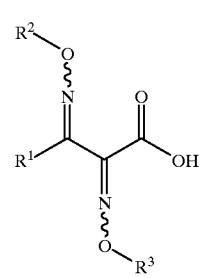

TABLE 1

| No | R$^1$ | R$^2$ | R$^3$ |
|---|---|---|---|
| 1 | Me | Me | Me |
| 2 | Me | Me | Et |
| 3 | Me | Me | n-Pr |
| 4 | Me | Me | i-Pr |
| 5 | Me | Me | allyl |
| 6 | Me | Me | cinnamyl |
| 7 | Me | Me | 2-propynyl |
| 8 | Me | Me | 2-butynyl |
| 9 | Me | Me | 2-pyridyl |
| 10 | Me | Me | benzyl |
| 11 | Me | Me | 2-Cl-benzyl |
| 12 | Me | Me | 3-Cl-benzyl |
| 13 | Me | Me | 4-Cl-benzyl |
| 14 | Me | Me | 2-Me-benzyl |
| 15 | Me | Me | 3-Me-benzyl |
| 16 | Me | Me | 4-Me-benzyl |
| 17 | Me | Me | 2-MeO-benzyl |
| 18 | Me | Me | 3-MeO-benzyl |
| 19 | Me | Me | 4-MeO-benzyl |
| 20 | Me | Me | 2-Cl-4-MeO-benzyl |
| 21 | Me | Me | 3,4-(Cl)$_2$-benzyl |
| 22 | Me | Me | 2-Me-4-MeO-benzyl |
| 23 | Me | Me | α-Me-4-MeO-benzyl |
| 24 | Me | Me | 4-MeO-PhSO$_2$ |
| 25 | Me | Me | 4-pyridylCH$_2$ |

TABLE 2

| No | R$^1$ | R$^2$ | R$^3$ |
|---|---|---|---|
| 26 | Me | MeOCH$_2$ | Me |
| 27 | Me | MeOCH$_2$ | Et |
| 28 | Me | MeOCH$_2$ | n-Pr |
| 29 | Me | MeOCH$_2$ | i-Pr |
| 30 | Me | MeOCH$_2$ | allyl |
| 31 | Me | MeOCH$_2$ | cinnamyl |
| 32 | Me | MeOCH$_2$ | 2-propynyl |
| 33 | Me | MeOCH$_2$ | 2-butynyl |
| 34 | Me | MeOCH$_2$ | 2-pyridyl |
| 35 | Me | MeOCH$_2$ | benzyl |
| 36 | Me | MeOCH$_2$ | 2-Cl-benzyl |
| 37 | Me | MeOCH$_2$ | 3-Cl-benzyl |
| 38 | Me | MeOCH$_2$ | 4-Cl-benzyl |
| 39 | Me | MeOCH$_2$ | 2-Me-benzyl |
| 40 | Me | MeOCH$_2$ | 3-Me-benzyl |
| 41 | Me | MeOCH$_2$ | 4-Me-benzyl |
| 42 | Me | MeOCH$_2$ | 2-MeO-benzyl |
| 43 | Me | MeOCH$_2$ | 3-MeO-benzyl |
| 44 | Me | MeOCH$_2$ | 4-MeO-benzyl |
| 45 | Me | MeOCH$_2$ | 2-Cl-4-MeO-benzyl |
| 46 | Me | MeOCH$_2$ | 3,4-(Cl)$_2$-benzyl |
| 47 | Me | MeOCH$_2$ | 2-Me-4-MeO-benzyl |
| 48 | Me | MeOCH$_2$ | α-Me-4-MeO-benzyl |
| 49 | Me | MeOCH$_2$ | 4-MeO-PhSO$_2$ |
| 50 | Me | MeOCH$_2$ | 4-pyridylCH$_2$ |

TABLE 3

| No | R$^1$ | R$^2$ | R$^3$ |
|---|---|---|---|
| 51 | Me | Et | Me |
| 52 | Me | Et | Et |
| 53 | Me | Et | n-Pr |
| 54 | Me | Et | i-Pr |
| 55 | Me | Et | allyl |
| 56 | Me | Et | cinnamyl |
| 57 | Me | Et | 2-propynyl |
| 58 | Me | Et | 2-butynyl |
| 59 | Me | Et | 2-pyridyl |
| 60 | Me | Et | benzyl |
| 61 | Me | Et | 2-Cl-benzyl |
| 62 | Me | Et | 3-Cl-benzyl |
| 63 | Me | Et | 4-Cl-benzyl |
| 64 | Me | Et | 2-Me-benzyl |
| 65 | Me | Et | 3-Me-benzyl |
| 66 | Me | Et | 4-Me-benzyl |
| 67 | Me | Et | 2-MeO-benzyl |
| 68 | Me | Et | 3-MeO-benzyl |
| 69 | Me | Et | 4-MeO-benzyl |
| 70 | Me | Et | 2-Cl-4-MeO-benzyl |
| 71 | Me | Et | 3,4-(Cl)$_2$-benzyl |
| 72 | Me | Et | 2-Me-4-MeO-benzyl |
| 73 | Me | Et | α-Me-4-MeO-benzyl |
| 74 | Me | Et | 4-MeO-PhSO$_2$ |
| 75 | Me | Et | 4-pyridylCH$_2$ |

TABLE 4

| No | R$^1$ | R$^2$ | R$^3$ |
|---|---|---|---|
| 76 | Me | allyl | Me |
| 77 | Me | allyl | Et |
| 78 | Me | allyl | n-Pr |
| 79 | Me | allyl | i-Pr |
| 80 | Me | allyl | allyl |
| 81 | Me | allyl | cinnamyl |
| 82 | Me | allyl | 2-propynyl |
| 83 | Me | allyl | 2-butynyl |
| 84 | Me | allyl | 2-pyridyl |
| 85 | Me | allyl | benzyl |
| 86 | Me | allyl | 2-Cl-benzyl |
| 87 | Me | allyl | 3-Cl-benzyl |

TABLE 4-continued

| No | R¹ | R² | R³ |
|---|---|---|---|
| 88 | Me | allyl | 4-Cl-benzyl |
| 89 | Me | allyl | 2-Me-benzyl |
| 90 | Me | allyl | 3-Me-benzyl |
| 91 | Me | allyl | 4-Me-benzyl |
| 92 | Me | allyl | 2-MeO-benzyl |
| 93 | Me | allyl | 3-MeO-benzyl |
| 94 | Me | allyl | 4-MeO-benzyl |
| 95 | Me | allyl | 2-Cl-4-MeO-benzyl |
| 96 | Me | allyl | 3,4-(Cl)₂-benzyl |
| 97 | Me | allyl | 2-Me-4-MeO-benzyl |
| 98 | Me | allyl | α-Me-4-MeO-benzyl |
| 99 | Me | allyl | 4-MeO-PhSO₂ |
| 100 | Me | allyl | 4-pyridylCH₂ |

TABLE 5

| No | R¹ | R² | R³ |
|---|---|---|---|
| 101 | Me | cinnamyl | Me |
| 102 | Me | cinnamyl | Et |
| 103 | Me | cinnamyl | n-Pr |
| 104 | Me | cinnamyl | i-Pr |
| 105 | Me | cinnamyl | allyl |
| 106 | Me | cinnamyl | cinnamyl |
| 107 | Me | cinnamyl | 2-propynyl |
| 108 | Me | cinnamyl | 2-butynyl |
| 109 | Me | cinnamyl | 2-pyridyl |
| 110 | Me | cinnamyl | benzyl |
| 111 | Me | cinnamyl | 2-Cl-benzyl |
| 112 | Me | cinnamyl | 3-Cl-benzyl |
| 113 | Me | cinnamyl | 4-Cl-benzyl |
| 114 | Me | cinnamyl | 2-Me-benzyl |
| 115 | Me | cinnamyl | 3-Me-benzyl |
| 116 | Me | cinnamyl | 4-Me-benzyl |
| 117 | Me | cinnamyl | 2-MeO-benzyl |
| 118 | Me | cinnamyl | 3-MeO-benzyl |
| 119 | Me | cinnamyl | 4-MeO-benzyl |
| 120 | Me | cinnamyl | 2-Cl-4-MeO-benzyl |
| 121 | Me | cinnamyl | 3,4-(Cl)₂-benzyl |
| 122 | Me | cinnamyl | 2-Me-4-MeO-benzyl |
| 123 | Me | cinnamyl | α-Me-4-MeO-benzyl |
| 124 | Me | cinnamyl | 4-MeO-PhSO₂ |
| 125 | Me | cinnamyl | 4-pyridylCH₂ |

TABLE 6

| No | R¹ | R² | R³ |
|---|---|---|---|
| 126 | Me | 2-propynyl | Me |
| 127 | Me | 2-propynyl | Et |
| 128 | Me | 2-propynyl | n-Pr |
| 129 | Me | 2-propynyl | i-Pr |
| 130 | Me | 2-propynyl | allyl |
| 131 | Me | 2-propynyl | cinnamyl |
| 132 | Me | 2-propynyl | 2-propynyl |
| 133 | Me | 2-propynyl | 2-butynyl |
| 134 | Me | 2-propynyl | 2-pyridyl |
| 135 | Me | 2-propynyl | benzyl |
| 136 | Me | 2-propynyl | 2-Cl-benzyl |
| 137 | Me | 2-propynyl | 3-Cl-benzyl |
| 138 | Me | 2-propynyl | 4-Cl-benzyl |
| 139 | Me | 2-propynyl | 2-Me-benzyl |
| 140 | Me | 2-propynyl | 3-Me-benzyl |
| 141 | Me | 2-propynyl | 4-Me-benzyl |
| 142 | Me | 2-propynyl | 2-MeO-benzyl |
| 143 | Me | 2-propynyl | 3-MeO-benzyl |
| 144 | Me | 2-propynyl | 4-MeO-benzyl |
| 145 | Me | 2-propynyl | 2-Cl-4-MeO-benzyl |
| 146 | Me | 2-propynyl | 3,4-(Cl)₂-benzyl |
| 147 | Me | 2-propynyl | 2-Me-4-MeO-benzyl |
| 148 | Me | 2-propynyl | α-Me-4-MeO-benzyl |

TABLE 6-continued

| No | R¹ | R² | R³ |
|---|---|---|---|
| 149 | Me | 2-propynyl | 4-MeO-PhSO₂ |
| 150 | Me | 2-propynyl | 4-pyridylCH₂ |

TABLE 7

| No | R¹ | R² | R³ |
|---|---|---|---|
| 151 | Me | 2-pyridyl | Me |
| 152 | Me | 2-pyridyl | Et |
| 153 | Me | 2-pyridyl | n-Pr |
| 154 | Me | 2-pyridyl | i-Pr |
| 155 | Me | 2-pyridyl | allyl |
| 156 | Me | 2-pyridyl | cinnamyl |
| 157 | Me | 2-pyridyl | 2-propynyl |
| 158 | Me | 2-pyridyl | 2-butynyl |
| 159 | Me | 2-pyridyl | 2-pyridyl |
| 160 | Me | 2-pyridyl | benzyl |
| 161 | Me | 2-pyridyl | 2-Cl-benzyl |
| 162 | Me | 2-pyridyl | 3-Cl-benzyl |
| 163 | Me | 2-pyridyl | 4-Cl-benzyl |
| 164 | Me | 2-pyridyl | 2-Me-benzyl |
| 165 | Me | 2-pyridyl | 3-Me-benzyl |
| 166 | Me | 2-pyridyl | 4-Me-benzyl |
| 167 | Me | 2-pyridyl | 2-MeO-benzyl |
| 168 | Me | 2-pyridyl | 3-MeO-benzyl |
| 169 | Me | 2-pyridyl | 4-MeO-benzyl |
| 170 | Me | 2-pyridyl | 2-Cl-4-MeO-benzyl |
| 171 | Me | 2-pyridyl | 3,4-(Cl)₂-benzyl |
| 172 | Me | 2-pyridyl | 2-Me-4-MeO-benzyl |
| 173 | Me | 2-pyridyl | α-Me-4-MeO-benzyl |
| 174 | Me | 2-pyridyl | 4-MeO-PhSO₂ |
| 175 | Me | 2-pyridyl | 4-pyridylCH₂ |

TABLE 8

| No | R¹ | R² | R³ |
|---|---|---|---|
| 176 | Me | benzyl | Me |
| 177 | Me | benzyl | Et |
| 178 | Me | benzyl | n-Pr |
| 179 | Me | benzyl | i-Pr |
| 180 | Me | benzyl | allyl |
| 181 | Me | benzyl | cinnamyl |
| 182 | Me | benzyl | 2-propynyl |
| 183 | Me | benzyl | 2-butynyl |
| 184 | Me | benzyl | 2-pyridyl |
| 185 | Me | benzyl | benzyl |
| 186 | Me | benzyl | 2-Cl-benzyl |
| 187 | Me | benzyl | 3-Cl-benzyl |
| 188 | Me | benzyl | 4-Cl-benzyl |
| 189 | Me | benzyl | 2-Me-benzyl |
| 190 | Me | benzyl | 3-Me-benzyl |
| 191 | Me | benzyl | 4-Me-benzyl |
| 192 | Me | benzyl | 2-MeO-benzyl |
| 193 | Me | benzyl | 3-MeO-benzyl |
| 194 | Me | benzyl | 4-MeO-benzyl |
| 195 | Me | benzyl | 2-Cl-4-MeO-benzyl |
| 196 | Me | benzyl | 3,4-(Cl)₂-benzyl |
| 197 | Me | benzyl | 2-Me-4-MeO-benzyl |
| 198 | Me | benzyl | α-Me-4-MeO-benzyl |
| 199 | Me | benzyl | 4-MeO-PhSO₂ |
| 200 | Me | benzyl | 4-pyridylCH₂ |

TABLE 9

| No | R¹ | R² | R³ |
|---|---|---|---|
| 201 | Me | 2-butynyl | Me |
| 202 | Me | 2-butynyl | Et |
| 203 | Me | 2-butynyl | n-Pr |
| 204 | Me | 2-butynyl | i-Pr |

TABLE 9-continued

| No | R¹ | R² | R³ |
|---|---|---|---|
| 205 | Me | 2-butynyl | allyl |
| 206 | Me | 2-butynyl | cinnamyl |
| 207 | Me | 2-butynyl | 2-propynyl |
| 208 | Me | 2-butynyl | 2-butynyl |
| 209 | Me | 2-butynyl | 2-pyridyl |
| 210 | Me | 2-butynyl | benzyl |
| 211 | Me | 2-butynyl | 2-Cl-benzyl |
| 212 | Me | 2-butynyl | 3-Cl-benzyl |
| 213 | Me | 2-butynyl | 4-Cl-benzyl |
| 214 | Me | 2-butynyl | 2-Me-benzyl |
| 215 | Me | 2-butynyl | 3-Me-benzyl |
| 216 | Me | 2-butynyl | 4-Me-benzyl |
| 217 | Me | 2-butynyl | 2-MeO-benzyl |
| 218 | Me | 2-butynyl | 3-MeO-benzyl |
| 219 | Me | 2-butynyl | 4-MeO-benzyl |
| 220 | Me | 2-butynyl | 2-Cl-4-MeO-benzyl |
| 221 | Me | 2-butynyl | 3,4-(Cl)$_2$-benzyl |
| 222 | Me | 2-butynyl | 2-Me-4-MeO-benzyl |
| 223 | Me | 2-butynyl | α-Me-4-MeO-benzyl |
| 224 | Me | 2-butynyl | 4-MeO-PhSO$_2$ |
| 225 | Me | 2-butynyl | 4-pyridylCH$_2$ |

TABLE 10

| No | R¹ | R² | R³ |
|---|---|---|---|
| 226 | Me | Ph | Me |
| 227 | Me | Ph | Et |
| 228 | Me | Ph | n-Pr |
| 229 | Me | Ph | i-Pr |
| 230 | Me | Ph | allyl |
| 231 | Me | Ph | cinnamyl |
| 232 | Me | Ph | 2-propynyl |
| 233 | Me | Ph | 2-butynyl |
| 234 | Me | Ph | 2-pyridyl |
| 235 | Me | Ph | benzyl |
| 236 | Me | Ph | 2-Cl-benzyl |
| 237 | Me | Ph | 3-Cl-benzyl |
| 238 | Me | Ph | 4-Cl-benzyl |
| 239 | Me | Ph | 2-Me-benzyl |
| 240 | Me | Ph | 3-Me-benzyl |
| 241 | Me | Ph | 4-Me-benzyl |
| 242 | Me | Ph | 2-MeO-benzyl |
| 243 | Me | Ph | 3-MeO-benzyl |
| 244 | Me | Ph | 4-MeO-benzyl |
| 245 | Me | Ph | 2-Cl-4-MeO-benzyl |
| 246 | Me | Ph | 3,4-(Cl)$_2$-benzyl |
| 247 | Me | Ph | 2-Me-4-MeO-benzyl |
| 248 | Me | Ph | α-Me-4-MeO-benzyl |
| 249 | Me | Ph | 4-MeO-PhSO$_2$ |
| 250 | Me | Ph | 4-pyridylCH$_2$ |

TABLE 11

| No | R¹ | R² | R³ |
|---|---|---|---|
| 251 | Me | 2-Cl-benzyl | Me |
| 252 | Me | 2-Cl-benzyl | Et |
| 253 | Me | 2-Cl-benzyl | n-Pr |
| 254 | Me | 2-Cl-benzyl | i-Pr |
| 255 | Me | 2-Cl-benzyl | allyl |
| 256 | Me | 2-Cl-benzyl | cinnamyl |
| 257 | Me | 2-Cl-benzyl | 2-propynyl |
| 258 | Me | 2-Cl-benzyl | 2-butynyl |
| 259 | Me | 2-Cl-benzyl | 2-pyridyl |
| 260 | Me | 2-Cl-benzyl | benzyl |
| 261 | Me | 2-Cl-benzyl | 2-Cl-benzyl |
| 262 | Me | 2-Cl-benzyl | 3-Cl-benzyl |
| 263 | Me | 2-Cl-benzyl | 4-Cl-benzyl |
| 264 | Me | 2-Cl-benzyl | 2-Me-benzyl |
| 265 | Me | 2-Cl-benzyl | 3-Me-benzyl |
| 266 | Me | 2-Cl-benzyl | 4-Me-benzyl |

TABLE 11-continued

| No | R¹ | R² | R³ |
|---|---|---|---|
| 267 | Me | 2-Cl-benzyl | 2-MeO-benzyl |
| 268 | Me | 2-Cl-benzyl | 3-MeO-benzyl |
| 269 | Me | 2-Cl-benzyl | 4-MeO-benzyl |
| 270 | Me | 2-Cl-benzyl | 2-Cl-4-MeO-benzyl |
| 271 | Me | 2-Cl-benzyl | 3,4-(Cl)$_2$-benzyl |
| 272 | Me | 2-Cl-benzyl | 2-Me-4-MeO-benzyl |
| 273 | Me | 2-Cl-benzyl | α-Me-4-MeO-benzyl |
| 274 | Me | 2-Cl-benzyl | 4-MeO-PhSO$_2$ |
| 275 | Me | 2-Cl-benzyl | 4-pyridylCH$_2$ |

TABLE 12

| No | R¹ | R² | R³ |
|---|---|---|---|
| 276 | Me | 3-Cl-benzyl | Me |
| 277 | Me | 3-Cl-benzyl | Et |
| 278 | Me | 3-Cl-benzyl | n-Pr |
| 279 | Me | 3-Cl-benzyl | i-Pr |
| 280 | Me | 3-Cl-benzyl | allyl |
| 281 | Me | 3-Cl-benzyl | cinnamyl |
| 282 | Me | 3-Cl-benzyl | 2-propynyl |
| 283 | Me | 3-Cl-benzyl | 2-butynyl |
| 284 | Me | 3-Cl-benzyl | 2-pyridyl |
| 285 | Me | 3-Cl-benzyl | benzyl |
| 286 | Me | 3-Cl-benzyl | 2-Cl-benzyl |
| 287 | Me | 3-Cl-benzyl | 3-Cl-benzyl |
| 288 | Me | 3-Cl-benzyl | 4-Cl-benzyl |
| 289 | Me | 3-Cl-benzyl | 2-Me-benzyl |
| 290 | Me | 3-Cl-benzyl | 3-Me-benzyl |
| 291 | Me | 3-Cl-benzyl | 4-Me-benzyl |
| 292 | Me | 3-Cl-benzyl | 2-MeO-benzyl |
| 293 | Me | 3-Cl-benzyl | 3-MeO-benzyl |
| 294 | Me | 3-Cl-benzyl | 4-MeO-benzyl |
| 295 | Me | 3-Cl-benzyl | 2-Cl-4-MeO-benzyl |
| 296 | Me | 3-Cl-benzyl | 3,4-(Cl)$_2$-benzyl |
| 297 | Me | 3-Cl-benzyl | 2-Me-4-MeO-benzyl |
| 298 | Me | 3-Cl-benzyl | α-Me-4-MeO-benzyl |
| 299 | Me | 3-Cl-benzyl | 4-MeO-PhSO$_2$ |
| 300 | Me | 3-Cl-benzyl | 4-pyridylCH$_2$ |

TABLE 13

| No | R¹ | R² | R³ |
|---|---|---|---|
| 301 | Me | 4-Cl-benzyl | Me |
| 302 | Me | 4-Cl-benzyl | Et |
| 303 | Me | 4-Cl-benzyl | n-Pr |
| 304 | Me | 4-Cl-benzyl | i-Pr |
| 305 | Me | 4-Cl-benzyl | allyl |
| 306 | Me | 4-Cl-benzyl | cinnamyl |
| 307 | Me | 4-Cl-benzyl | 2-propynyl |
| 308 | Me | 4-Cl-benzyl | 2-butynyl |
| 309 | Me | 4-Cl-benzyl | 2-pyridyl |
| 310 | Me | 4-Cl-benzyl | benzyl |
| 311 | Me | 4-Cl-benzyl | 2-Cl-benzyl |
| 312 | Me | 4-Cl-benzyl | 3-Cl-benzyl |
| 313 | Me | 4-Cl-benzyl | 4-Cl-benzyl |
| 314 | Me | 4-Cl-benzyl | 2-Me-benzyl |
| 315 | Me | 4-Cl-benzyl | 3-Me-benzyl |
| 316 | Me | 4-Cl-benzyl | 4-Me-benzyl |
| 317 | Me | 4-Cl-benzyl | 2-MeO-benzyl |
| 318 | Me | 4-Cl-benzyl | 3-MeO-benzyl |
| 319 | Me | 4-Cl-benzyl | 4-MeO-benzyl |
| 320 | Me | 4-Cl-benzyl | 2-Cl-4-MeO-benzyl |
| 321 | Me | 4-Cl-benzyl | 3,4-(Cl)$_2$-benzyl |
| 322 | Me | 4-Cl-benzyl | 2-Me-4-MeO-benzyl |
| 323 | Me | 4-Cl-benzyl | α-Me-4-MeO-benzyl |
| 324 | Me | 4-Cl-benzyl | 4-MeO-PhSO$_2$ |
| 325 | Me | 4-Cl-benzyl | 4-pyridylCH$_2$ |

TABLE 14

| No | R¹ | R² | R³ |
|---|---|---|---|
| 326 | Me | 2-Me-benzyl | Me |
| 327 | Me | 2-Me-benzyl | Et |
| 328 | Me | 2-Me-benzyl | n-Pr |
| 329 | Me | 2-Me-benzyl | i-Pr |
| 330 | Me | 2-Me-benzyl | allyl |
| 331 | Me | 2-Me-benzyl | cinnamyl |
| 332 | Me | 2-Me-benzyl | 2-propynyl |
| 333 | Me | 2-Me-benzyl | 2-butynyl |
| 334 | Me | 2-Me-benzyl | 2-pyridyl |
| 335 | Me | 2-Me-benzyl | benzyl |
| 336 | Me | 2-Me-benzyl | 2-Cl-benzyl |
| 337 | Me | 2-Me-benzyl | 3-Cl-benzyl |
| 338 | Me | 2-Me-benzyl | 4-Cl-benzyl |
| 339 | Me | 2-Me-benzyl | 2-Me-benzyl |
| 340 | Me | 2-Me-benzyl | 3-Me-benzyl |
| 341 | Me | 2-Me-benzyl | 4-Me-benzyl |
| 342 | Me | 2-Me-benzyl | 2-MeO-benzyl |
| 343 | Me | 2-Me-benzyl | 3-MeO-benzyl |
| 344 | Me | 2-Me-benzyl | 4-MeO-benzyl |
| 345 | Me | 2-Me-benzyl | 2-Cl-4-MeO-benzyl |
| 346 | Me | 2-Me-benzyl | 3,4-(Cl)$_2$-benzyl |
| 347 | Me | 2-Me-benzyl | 2-Me-4-MeO-benzyl |
| 348 | Me | 2-Me-benzyl | α-Me-4-MeO-benzyl |
| 349 | Me | 2-Me-benzyl | 4-MeO-PhSO$_2$ |
| 350 | Me | 2-Me-benzyl | 4-pyridylCH$_2$ |

TABLE 15

| No | R¹ | R² | R³ |
|---|---|---|---|
| 351 | Me | 3-Me-benzyl | Me |
| 352 | Me | 3-Me-benzyl | Et |
| 353 | Me | 3-Me-benzyl | n-Pr |
| 354 | Me | 3-Me-benzyl | i-Pr |
| 355 | Me | 3-Me-benzyl | allyl |
| 356 | Me | 3-Me-benzyl | cinnamyl |
| 357 | Me | 3-Me-benzyl | 2-propynyl |
| 358 | Me | 3-Me-benzyl | 2-butynyl |
| 359 | Me | 3-Me-benzyl | 2-pyridyl |
| 360 | Me | 3-Me-benzyl | benzyl |
| 361 | Me | 3-Me-benzyl | 2-Cl-benzyl |
| 362 | Me | 3-Me-benzyl | 3-Cl-benzyl |
| 363 | Me | 3-Me-benzyl | 4-Cl-benzyl |
| 364 | Me | 3-Me-benzyl | 2-Me-benzyl |
| 365 | Me | 3-Me-benzyl | 3-Me-benzyl |
| 366 | Me | 3-Me-benzyl | 4-Me-benzyl |
| 367 | Me | 3-Me-benzyl | 2-MeO-benzyl |
| 368 | Me | 3-Me-benzyl | 3-MeO-benzyl |
| 369 | Me | 3-Me-benzyl | 4-MeO-benzyl |
| 370 | Me | 3-Me-benzyl | 2-Cl-4-MeO-benzyl |
| 371 | Me | 3-Me-benzyl | 3,4-(Cl)$_2$-benzyl |
| 372 | Me | 3-Me-benzyl | 2-Me-4-MeO-benzyl |
| 373 | Me | 3-Me-benzyl | α-Me-4-MeO-benzyl |
| 374 | Me | 3-Me-benzyl | 4-MeO-PhSO$_2$ |
| 375 | Me | 3-Me-benzyl | 4-pyridylCH$_2$ |

TABLE 16

| No | R¹ | R² | R³ |
|---|---|---|---|
| 376 | Me | 4-Me-benzyl | Me |
| 377 | Me | 4-Me-benzyl | Et |
| 378 | Me | 4-Me-benzyl | n-Pr |
| 379 | Me | 4-Me-benzyl | i-Pr |
| 380 | Me | 4-Me-benzyl | allyl |
| 381 | Me | 4-Me-benzyl | cinnamyl |
| 382 | Me | 4-Me-benzyl | 2-propynyl |
| 383 | Me | 4-Me-benzyl | 2-butynyl |
| 384 | Me | 4-Me-benzyl | 2-pyridyl |
| 385 | Me | 4-Me-benzyl | benzyl |
| 386 | Me | 4-Me-benzyl | 2-Cl-benzyl |
| 387 | Me | 4-Me-benzyl | 3-Cl-benzyl |
| 388 | Me | 4-Me-benzyl | 4-Cl-benzyl |
| 389 | Me | 4-Me-benzyl | 2-Me-benzyl |
| 390 | Me | 4-Me-benzyl | 3-Me-benzyl |
| 391 | Me | 4-Me-benzyl | 4-Me-benzyl |
| 392 | Me | 4-Me-benzyl | 2-MeO-benzyl |
| 393 | Me | 4-Me-benzyl | 3-MeO-benzyl |
| 394 | Me | 4-Me-benzyl | 4-MeO-benzyl |
| 395 | Me | 4-Me-benzyl | 2-Cl-4-MeO-benzyl |
| 396 | Me | 4-Me-benzyl | 3,4-(Cl)$_2$-benzyl |
| 397 | Me | 4-Me-benzyl | 2-Me-4-MeO-benzyl |
| 398 | Me | 4-Me-benzyl | α-Me-4-MeO-benzyl |
| 399 | Me | 4-Me-benzyl | 4-MeO-PhSO$_2$ |
| 400 | Me | 4-Me-benzyl | 4-pyridylCH$_2$ |

TABLE 17

| No | R¹ | R² | R³ |
|---|---|---|---|
| 401 | Me | 2-MeO-benzyl | Me |
| 402 | Me | 2-MeO-benzyl | Et |
| 403 | Me | 2-MeO-benzyl | n-Pr |
| 404 | Me | 2-MeO-benzyl | i-Pr |
| 405 | Me | 2-MeO-benzyl | allyl |
| 406 | Me | 2-MeO-benzyl | cinnamyl |
| 407 | Me | 2-MeO-benzyl | 2-propynyl |
| 408 | Me | 2-MeO-benzyl | 2-butynyl |
| 409 | Me | 2-MeO-benzyl | 2-pyridyl |
| 410 | Me | 2-MeO-benzyl | benzyl |
| 411 | Me | 2-MeO-benzyl | 2-Cl-benzyl |
| 412 | Me | 2-MeO-benzyl | 3-Cl-benzyl |
| 413 | Me | 2-MeO-benzyl | 4-Cl-benzyl |
| 414 | Me | 2-MeO-benzyl | 2-Me-benzyl |
| 415 | Me | 2-MeO-benzyl | 3-Me-benzyl |
| 416 | Me | 2-MeO-benzyl | 4-Me-benzyl |
| 417 | Me | 2-MeO-benzyl | 2-MeO-benzyl |
| 418 | Me | 2-MeO-benzyl | 3-MeO-benzyl |
| 419 | Me | 2-MeO-benzyl | 4-MeO-benzyl |
| 420 | Me | 2-MeO-benzyl | 2-Cl-4-MeO-benzyl |
| 421 | Me | 2-MeO-benzyl | 3,4-(Cl)$_2$-benzyl |
| 422 | Me | 2-MeO-benzyl | 2-Me-4-MeO-benzyl |
| 423 | Me | 2-MeO-benzyl | α-Me-4-MeO-benzyl |
| 424 | Me | 2-MeO-benzyl | 4-MeO-PhSO$_2$ |
| 425 | Me | 2-MeO-benzyl | 4-pyridylCH$_2$ |

TABLE 18

| No | R¹ | R² | R³ |
|---|---|---|---|
| 426 | Me | 3-MeO-benzyl | Me |
| 427 | Me | 3-MeO-benzyl | Et |
| 428 | Me | 3-MeO-benzyl | n-Pr |
| 429 | Me | 3-MeO-benzyl | i-Pr |
| 430 | Me | 3-MeO-benzyl | allyl |
| 431 | Me | 3-MeO-benzyl | cinnamyl |
| 432 | Me | 3-MeO-benzyl | 2-propynyl |
| 433 | Me | 3-MeO-benzyl | 2-butynyl |
| 434 | Me | 3-MeO-benzyl | 2-pyridyl |
| 435 | Me | 3-MeO-benzyl | benzyl |
| 436 | Me | 3-MeO-benzyl | 2-Cl-benzyl |
| 437 | Me | 3-MeO-benzyl | 3-Cl-benzyl |
| 438 | Me | 3-MeO-benzyl | 4-Cl-benzyl |
| 439 | Me | 3-MeO-benzyl | 2-Me-benzyl |
| 440 | Me | 3-MeO-benzyl | 3-Me-benzyl |
| 441 | Me | 3-MeO-benzyl | 4-Me-benzyl |
| 442 | Me | 3-MeO-benzyl | 2-MeO-benzyl |
| 443 | Me | 3-MeO-benzyl | 3-MeO-benzyl |
| 444 | Me | 3-MeO-benzyl | 4-MeO-benzyl |
| 445 | Me | 3-MeO-benzyl | 2-Cl-4-MeO-benzyl |
| 446 | Me | 3-MeO-benzyl | 3,4-(Cl)$_2$-benzyl |
| 447 | Me | 3-MeO-benzyl | 2-Me-4-MeO-benzyl |
| 448 | Me | 3-MeO-benzyl | α-Me-4-MeO-benzyl |

TABLE 18-continued

| No | R¹ | R² | R³ |
|---|---|---|---|
| 449 | Me | 3-MeO-benzyl | 4-MeO-PhSO₂ |
| 450 | Me | 3-MeO-benzyl | 4-pyridylCH₂ |

TABLE 19

| No | R¹ | R² | R³ |
|---|---|---|---|
| 451 | Me | 4-MeO-benzyl | Me |
| 452 | Me | 4-MeO-benzyl | Et |
| 453 | Me | 4-MeO-benzyl | n-Pr |
| 454 | Me | 4-MeO-benzyl | i-Pr |
| 455 | Me | 4-MeO-benzyl | allyl |
| 456 | Me | 4-MeO-benzyl | cinnamyl |
| 457 | Me | 4-MeO-benzyl | 2-propynyl |
| 458 | Me | 4-MeO-benzyl | 2-butynyl |
| 459 | Me | 4-MeO-benzyl | 2-pyridyl |
| 460 | Me | 4-MeO-benzyl | benzyl |
| 461 | Me | 4-MeO-benzyl | 2-Cl-benzyl |
| 462 | Me | 4-MeO-benzyl | 3-Cl-benzyl |
| 463 | Me | 4-MeO-benzyl | 4-Cl-benzyl |
| 464 | Me | 4-MeO-benzyl | 2-Me-benzyl |
| 465 | Me | 4-MeO-benzyl | 3-Me-benzyl |
| 466 | Me | 4-MeO-benzyl | 4-Me-benzyl |
| 467 | Me | 4-MeO-benzyl | 2-MeO-benzyl |
| 468 | Me | 4-MeO-benzyl | 3-MeO-benzyl |
| 469 | Me | 4-MeO-benzyl | 4-MeO-benzyl |
| 470 | Me | 4-MeO-benzyl | 2-Cl-4-MeO-benzyl |
| 471 | Me | 4-MeO-benzyl | 3,4-(Cl)₂-benzyl |
| 472 | Me | 4-MeO-benzyl | 2-Me-4-MeO-benzyl |
| 473 | Me | 4-MeO-benzyl | α-Me-4-MeO-benzyl |
| 474 | Me | 4-MeO-benzyl | 4-MeO-PhSO₂ |
| 475 | Me | 4-MeO-benzyl | 4-pyridylCH₂ |

TABLE 20

| No | R¹ | R² | R³ |
|---|---|---|---|
| 476 | Me | 3,4-(Cl)₂-benzyl | Me |
| 477 | Me | 3,4-(Cl)₂-benzyl | Et |
| 478 | Me | 3,4-(Cl)₂-benzyl | n-Pr |
| 479 | Me | 3,4-(Cl)₂-benzyl | i-Pr |
| 480 | Me | 3,4-(Cl)₂-benzyl | allyl |
| 481 | Me | 3,4-(Cl)₂-benzyl | cinnamyl |
| 482 | Me | 3,4-(Cl)₂-benzyl | 2-propynyl |
| 483 | Me | 3,4-(Cl)₂-benzyl | 2-butynyl |
| 484 | Me | 3,4-(Cl)₂-benzyl | 2-pyridyl |
| 485 | Me | 3,4-(Cl)₂-benzyl | benzyl |
| 486 | Me | 3,4-(Cl)₂-benzyl | 2-Cl-benzyl |
| 487 | Me | 3,4-(Cl)₂-benzyl | 3-Cl-benzyl |
| 488 | Me | 3,4-(Cl)₂-benzyl | 4-Cl-benzyl |
| 489 | Me | 3,4-(Cl)₂-benzyl | 2-Me-benzyl |
| 490 | Me | 3,4-(Cl)₂-benzyl | 3-Me-benzyl |
| 491 | Me | 3,4-(Cl)₂-benzyl | 4-Me-benzyl |
| 492 | Me | 3,4-(Cl)₂-benzyl | 2-MeO-benzyl |
| 493 | Me | 3,4-(Cl)₂-benzyl | 3-MeO-benzyl |
| 494 | Me | 3,4-(Cl)₂-benzyl | 4-MeO-benzyl |
| 495 | Me | 3,4-(Cl)₂-benzyl | 2-Cl-4-MeO-benzyl |
| 496 | Me | 3,4-(Cl)₂-benzyl | 3,4-(Cl)₂-benzyl |
| 497 | Me | 3,4-(Cl)₂-benzyl | 2-Me-4-MeO-benzyl |
| 498 | Me | 3,4-(Cl)₂-benzyl | α-Me-4-MeO-benzyl |
| 499 | Me | 3,4-(Cl)₂-benzyl | 4-MeO-PhSO₂ |
| 500 | Me | 3,4-(Cl)₂-benzyl | 4-pyridylCH₂ |

TABLE 21

| No | R¹ | R² | R³ |
|---|---|---|---|
| 501 | Me | 2-Cl-4-MeO-benzyl | Me |
| 502 | Me | 2-Cl-4-MeO-benzyl | Et |
| 503 | Me | 2-Cl-4-MeO-benzyl | n-Pr |

TABLE 21-continued

| No | R¹ | R² | R³ |
|---|---|---|---|
| 504 | Me | 2-Cl-4-MeO-benzyl | i-Pr |
| 505 | Me | 2-Cl-4-MeO-benzyl | allyl |
| 506 | Me | 2-Cl-4-MeO-benzyl | cinnamyl |
| 507 | Me | 2-Cl-4-MeO-benzyl | 2-propynyl |
| 508 | Me | 2-Cl-4-MeO-benzyl | 2-butynyl |
| 509 | Me | 2-Cl-4-MeO-benzyl | 2-pyridyl |
| 510 | Me | 2-Cl-4-MeO-benzyl | benzyl |
| 511 | Me | 2-Cl-4-MeO-benzyl | 2-Cl-benzyl |
| 512 | Me | 2-Cl-4-MeO-benzyl | 3-Cl-benzyl |
| 513 | Me | 2-Cl-4-MeO-benzyl | 4-Cl-benzyl |
| 514 | Me | 2-Cl-4-MeO-benzyl | 2-Me-benzyl |
| 515 | Me | 2-Cl-4-MeO-benzyl | 3-Me-benzyl |
| 516 | Me | 2-Cl-4-MeO-benzyl | 4-Me-benzyl |
| 517 | Me | 2-Cl-4-MeO-benzyl | 2-MeO-benzyl |
| 518 | Me | 2-Cl-4-MeO-benzyl | 3-MeO-benzyl |
| 519 | Me | 2-Cl-4-MeO-benzyl | 4-MeO-benzyl |
| 520 | Me | 2-Cl-4-MeO-benzyl | 2-Cl-4-MeO-benzyl |
| 521 | Me | 2-Cl-4-MeO-benzyl | 3,4-(Cl)₂-benzyl |
| 522 | Me | 2-Cl-4-MeO-benzyl | 2-Me-4-MeO-benzyl |
| 523 | Me | 2-Cl-4-MeO-benzyl | α-Me-4-MeO-benzyl |
| 524 | Me | 2-Cl-4-MeO-benzyl | 4-MeO-PhSO₂ |
| 525 | Me | 2-Cl-4-MeO-benzyl | 4-pyridylCH₂ |

TABLE 22

| No | R¹ | R² | R³ |
|---|---|---|---|
| 526 | Me | 2-pyridylCH₂ | Me |
| 527 | Me | 2-pyridylCH₂ | Et |
| 528 | Me | 2-pyridylCH₂ | n-Pr |
| 529 | Me | 2-pyridylCH₂ | i-Pr |
| 530 | Me | 2-pyridylCH₂ | allyl |
| 531 | Me | 2-pyridylCH₂ | cinnamyl |
| 532 | Me | 2-pyridylCH₂ | 2-propynyl |
| 533 | Me | 2-pyridylCH₂ | 2-butynyl |
| 534 | Me | 2-pyridylCH₂ | 2-pyridyl |
| 535 | Me | 2-pyridylCH₂ | benzyl |
| 536 | Me | 2-pyridylCH₂ | 2-Cl-benzyl |
| 537 | Me | 2-pyridylCH₂ | 3-Cl-benzyl |
| 538 | Me | 2-pyridylCH₂ | 4-Cl-benzyl |
| 539 | Me | 2-pyridylCH₂ | 2-Me-benzyl |
| 540 | Me | 2-pyridylCH₂ | 3-Me-benzyl |
| 541 | Me | 2-pyridylCH₂ | 4-Me-benzyl |
| 542 | Me | 2-pyridylCH₂ | 2-MeO-benzyl |
| 543 | Me | 2-pyridylCH₂ | 3-MeO-benzyl |
| 544 | Me | 2-pyridylCH₂ | 4-MeO-benzyl |
| 545 | Me | 2-pyridylCH₂ | 2-Cl-4-MeO-benzyl |
| 546 | Me | 2-pyridylCH₂ | 3,4-(Cl)₂-benzyl |
| 547 | Me | 2-pyridylCH₂ | 2-Me-4-MeO-benzyl |
| 548 | Me | 2-pyridylCH₂ | α-Me-4-MeO-benzyl |
| 549 | Me | 2-pyridylCH₂ | 4-MeO-PhSO₂ |
| 550 | Me | 2-pyridylCH₂ | 4-pyridylCH₂ |

TABLE 23

| No | R¹ | R² | R³ |
|---|---|---|---|
| 551 | Me | 3-pyridylCH₂ | Me |
| 552 | Me | 3-pyridylCH₂ | Et |
| 553 | Me | 3-pyridylCH₂ | n-Pr |
| 554 | Me | 3-pyridylCH₂ | i-Pr |
| 555 | Me | 3-pyridylCH₂ | allyl |
| 556 | Me | 3-pyridylCH₂ | cinnamyl |
| 557 | Me | 3-pyridylCH₂ | 2-propynyl |
| 558 | Me | 3-pyridylCH₂ | 2-butynyl |
| 559 | Me | 3-pyridylCH₂ | 2-pyridyl |
| 560 | Me | 3-pyridylCH₂ | benzyl |
| 561 | Me | 3-pyridylCH₂ | 2-Cl-benzyl |
| 562 | Me | 3-pyridylCH₂ | 3-Cl-benzyl |
| 563 | Me | 3-pyridylCH₂ | 4-Cl-benzyl |
| 564 | Me | 3-pyridylCH₂ | 2-Me-benzyl |
| 565 | Me | 3-pyridylCH₂ | 3-Me-benzyl |

TABLE 23-continued

| No | R¹ | R² | R³ |
| --- | --- | --- | --- |
| 566 | Me | 3-pyridylCH₂ | 4-Me-benzyl |
| 567 | Me | 3-pyridylCH₂ | 2-MeO-benzyl |
| 568 | Me | 3-pyridylCH₂ | 3-MeO-benzyl |
| 569 | Me | 3-pyridylCH₂ | 4-MeO-benzyl |
| 570 | Me | 3-pyridylCH₂ | 2-Cl-4-MeO-benzyl |
| 571 | Me | 3-pyridylCH₂ | 3,4-(Cl)₂-benzyl |
| 572 | Me | 3-pyridylCH₂ | 2-Me-4-MeO-benzyl |
| 573 | Me | 3-pyridylCH₂ | α-Me-4-MeO-benzyl |
| 574 | Me | 3-pyridylCH₂ | 4-MeO-PhSO₂ |
| 575 | Me | 3-pyridylCH₂ | 4-pyridylCH₂ |

TABLE 24

| No | R¹ | R² | R³ |
| --- | --- | --- | --- |
| 576 | Me | 4-pyridylCH₂ | Me |
| 577 | Me | 4-pyridylCH₂ | Et |
| 578 | Me | 4-pyridylCH₂ | n-Pr |
| 579 | Me | 4-pyridylCH₂ | i-Pr |
| 580 | Me | 4-pyridylCH₂ | allyl |
| 581 | Me | 4-pyridylCH₂ | cinnamyl |
| 582 | Me | 4-pyridylCH₂ | 2-propynyl |
| 583 | Me | 4-pyridylCH₂ | 2-butynyl |
| 584 | Me | 4-pyridylCH₂ | 2-pyridyl |
| 585 | Me | 4-pyridylCH₂ | benzyl |
| 586 | Me | 4-pyridylCH₂ | 2-Cl-benzyl |
| 587 | Me | 4-pyridylCH₂ | 3-Cl-benzyl |
| 588 | Me | 4-pyridylCH₂ | 4-Cl-benzyl |
| 589 | Me | 4-pyridylCH₂ | 2-Me-benzyl |
| 590 | Me | 4-pyridylCH₂ | 3-Me-benzyl |
| 591 | Me | 4-pyridylCH₂ | 4-Me-benzyl |
| 592 | Me | 4-pyridylCH₂ | 2-MeO-benzyl |
| 593 | Me | 4-pyridylCH₂ | 3-MeO-benzyl |
| 594 | Me | 4-pyridylCH₂ | 4-MeO-benzyl |
| 595 | Me | 4-pyridylCH₂ | 2-Cl-4-MeO-benzyl |
| 596 | Me | 4-pyridylCH₂ | 3,4-(Cl)₂-benzyl |
| 597 | Me | 4-pyridylCH₂ | 2-Me-4-MeO-benzyl |
| 598 | Me | 4-pyridylCH₂ | α-Me-4-MeO-benzyl |
| 599 | Me | 4-pyridylCH₂ | 4-MeO-PhSO₂ |
| 600 | Me | 4-pyridylCH₂ | 4-pyridylCH₂ |

TABLE 25

| No | R¹ | R² | R³ |
| --- | --- | --- | --- |
| 601 | Et | Me | Me |
| 602 | Et | Me | Et |
| 603 | Et | Me | n-Pr |
| 604 | Et | Me | i-Pr |
| 605 | Et | Me | allyl |
| 606 | Et | Me | cinnamyl |
| 607 | Et | Me | 2-propynyl |
| 608 | Et | Me | 2-butynyl |
| 609 | Et | Me | 2-pyridyl |
| 610 | Et | Me | benzyl |
| 611 | Et | Me | 2-Cl-benzyl |
| 612 | Et | Me | 3-Cl-benzyl |
| 613 | Et | Me | 4-Cl-benzyl |
| 614 | Et | Me | 2-Me-benzyl |
| 615 | Et | Me | 3-Me-benzyl |
| 616 | Et | Me | 4-Me-benzyl |
| 617 | Et | Me | 2-MeO-benzyl |
| 618 | Et | Me | 3-MeO-benzyl |
| 619 | Et | Me | 4-MeO-benzyl |
| 620 | Et | Me | 2-Cl-4-MeO-benzyl |
| 621 | Et | Me | 3,4-(Cl)₂-benzyl |
| 622 | Et | Me | 2-Me-4-MeO-benzyl |
| 623 | Et | Me | α-Me-4-MeO-benzyl |
| 624 | Et | Me | 4-MeO-PhSO₂ |
| 625 | Et | Me | 4-pyridylCH₂ |

TABLE 26

| No | R¹ | R² | R³ |
| --- | --- | --- | --- |
| 626 | Et | MeOCH₂ | Me |
| 627 | Et | MeOCH₂ | Et |
| 628 | Et | MeOCH₂ | n-Pr |
| 629 | Et | MeOCH₂ | i-Pr |
| 630 | Et | MeOCH₂ | allyl |
| 631 | Et | MeOCH₂ | cinnamyl |
| 632 | Et | MeOCH₂ | 2-propynyl |
| 633 | Et | MeOCH₂ | 2-butynyl |
| 634 | Et | MeOCH₂ | 2-pyridyl |
| 635 | Et | MeOCH₂ | benzyl |
| 636 | Et | MeOCH₂ | 2-Cl-benzyl |
| 637 | Et | MeOCH₂ | 3-Cl-benzyl |
| 638 | Et | MeOCH₂ | 4-Cl-benzyl |
| 639 | Et | MeOCH₂ | 2-Me-benzyl |
| 640 | Et | MeOCH₂ | 3-Me-benzyl |
| 641 | Et | MeOCH₂ | 4-Me-benzyl |
| 642 | Et | MeOCH₂ | 2-MeO-benzyl |
| 643 | Et | MeOCH₂ | 3-MeO-benzyl |
| 644 | Et | MeOCH₂ | 4-MeO-benzyl |
| 645 | Et | MeOCH₂ | 2-Cl-4-MeO-benzyl |
| 646 | Et | MeOCH₂ | 3,4-(Cl)₂-benzyl |
| 647 | Et | MeOCH₂ | 2-Me-4-MeO-benzyl |
| 648 | Et | MeOCH₂ | α-Me-4-MeO-benzyl |
| 649 | Et | MeOCH₂ | 4-MeO-PhSO₂ |
| 650 | Et | MeOCH₂ | 4-pyridylCH₂ |

TABLE 27

| No | R¹ | R² | R³ |
| --- | --- | --- | --- |
| 651 | Et | Et | Me |
| 652 | Et | Et | Et |
| 653 | Et | Et | n-Pr |
| 654 | Et | Et | i-Pr |
| 655 | Et | Et | allyl |
| 656 | Et | Et | cinnamyl |
| 657 | Et | Et | 2-propynyl |
| 658 | Et | Et | 2-butynyl |
| 659 | Et | Et | 2-pyridyl |
| 660 | Et | Et | benzyl |
| 661 | Et | Et | 2-Cl-benzyl |
| 662 | Et | Et | 3-Cl-benzyl |
| 663 | Et | Et | 4-Cl-benzyl |
| 664 | Et | Et | 2-Me-benzyl |
| 665 | Et | Et | 3-Me-benzyl |
| 666 | Et | Et | 4-Me-benzyl |
| 667 | Et | Et | 2-MeO-benzyl |
| 668 | Et | Et | 3-MeO-benzyl |
| 669 | Et | Et | 4-MeO-benzyl |
| 670 | Et | Et | 2-Cl-4-MeO-benzyl |
| 671 | Et | Et | 3,4-(Cl)₂-benzyl |
| 672 | Et | Et | 2-Me-4-MeO-benzyl |
| 673 | Et | Et | α-Me-4-MeO-benzyl |
| 674 | Et | Et | 4-MeO-PhSO₂ |
| 675 | Et | Et | 4-pyridylCH₂ |

TABLE 28

| No | R¹ | R² | R³ |
| --- | --- | --- | --- |
| 676 | Et | allyl | Me |
| 677 | Et | allyl | Et |
| 678 | Et | allyl | n-Pr |
| 679 | Et | allyl | i-Pr |
| 680 | Et | allyl | allyl |
| 681 | Et | allyl | cinnamyl |
| 682 | Et | allyl | 2-propynyl |
| 683 | Et | allyl | 2-butynyl |
| 684 | Et | allyl | 2-pyridyl |
| 685 | Et | allyl | benzyl |
| 686 | Et | allyl | 2-Cl-benzyl |
| 687 | Et | allyl | 3-Cl-benzyl |

TABLE 28-continued

| No | R¹ | R² | R³ |
| --- | --- | --- | --- |
| 688 | Et | allyl | 4-Cl-benzyl |
| 689 | Et | allyl | 2-Me-benzyl |
| 690 | Et | allyl | 3-Me-benzyl |
| 691 | Et | allyl | 4-Me-benzyl |
| 692 | Et | allyl | 2-MeO-benzyl |
| 693 | Et | allyl | 3-MeO-benzyl |
| 694 | Et | allyl | 4-MeO-benzyl |
| 695 | Et | allyl | 2-Cl-4-MeO-benzyl |
| 696 | Et | allyl | 3,4-(Cl)$_2$-benzyl |
| 697 | Et | allyl | 2-Me-4-MeO-benzyl |
| 698 | Et | allyl | α-Me-4-MeO-benzyl |
| 699 | Et | allyl | 4-MeO-PhSO$_2$ |
| 700 | Et | allyl | 4-pyridylCH$_2$ |

TABLE 29

| No | R¹ | R² | R³ |
| --- | --- | --- | --- |
| 701 | Et | cinnamyl | Me |
| 702 | Et | cinnamyl | Et |
| 703 | Et | cinnamyl | n-Pr |
| 704 | Et | cinnamyl | i-Pr |
| 705 | Et | cinnamyl | allyl |
| 706 | Et | cinnamyl | cinnamyl |
| 707 | Et | cinnamyl | 2-propynyl |
| 708 | Et | cinnamyl | 2-butynyl |
| 709 | Et | cinnamyl | 2-pyridyl |
| 710 | Et | cinnamyl | benzyl |
| 711 | Et | cinnamyl | 2-Cl-benzyl |
| 712 | Et | cinnamyl | 3-Cl-benzyl |
| 713 | Et | cinnamyl | 4-Cl-benzyl |
| 714 | Et | cinnamyl | 2-Me-benzyl |
| 715 | Et | cinnamyl | 3-Me-benzyl |
| 716 | Et | cinnamyl | 4-Me-benzyl |
| 717 | Et | cinnamyl | 2-MeO-benzyl |
| 718 | Et | cinnamyl | 3-MeO-benzyl |
| 719 | Et | cinnamyl | 4-MeO-benzyl |
| 720 | Et | cinnamyl | 2-Cl-4-MeO-benzyl |
| 721 | Et | cinnamyl | 3,4-(Cl)$_2$-benzyl |
| 722 | Et | cinnamyl | 2-Me-4-MeO-benzyl |
| 723 | Et | cinnamyl | α-Me-4-MeO-benzyl |
| 724 | Et | cinnamyl | 4-MeO-PhSO$_2$ |
| 725 | Et | cinnamyl | 4-pyridylCH$_2$ |

TABLE 30

| No | R¹ | R² | R³ |
| --- | --- | --- | --- |
| 726 | Et | 2-propynyl | Me |
| 727 | Et | 2-propynyl | Et |
| 728 | Et | 2-propynyl | n-Pr |
| 729 | Et | 2-propynyl | i-Pr |
| 730 | Et | 2-propynyl | allyl |
| 731 | Et | 2-propynyl | cinnamyl |
| 732 | Et | 2-propynyl | 2-propynyl |
| 733 | Et | 2-propynyl | 2-butynyl |
| 734 | Et | 2-propynyl | 2-pyridyl |
| 735 | Et | 2-propynyl | benzyl |
| 736 | Et | 2-propynyl | 2-Cl-benzyl |
| 737 | Et | 2-propynyl | 3-Cl-benzyl |
| 738 | Et | 2-propynyl | 4-Cl-benzyl |
| 739 | Et | 2-propynyl | 2-Me-benzyl |
| 740 | Et | 2-propynyl | 3-Me-benzyl |
| 741 | Et | 2-propynyl | 4-Me-benzyl |
| 742 | Et | 2-propynyl | 2-MeO-benzyl |
| 743 | Et | 2-propynyl | 3-MeO-benzyl |
| 744 | Et | 2-propynyl | 4-MeO-benzyl |
| 745 | Et | 2-propynyl | 2-Cl-4-MeO-benzyl |
| 746 | Et | 2-propynyl | 3,4-(Cl)$_2$-benzyl |
| 747 | Et | 2-propynyl | 2-Me-4-MeO-benzyl |
| 748 | Et | 2-propynyl | α-Me-4-MeO-benzyl |

TABLE 30-continued

| No | R¹ | R² | R³ |
| --- | --- | --- | --- |
| 749 | Et | 2-propynyl | 4-MeO-PhSO$_2$ |
| 750 | Et | 2-propynyl | 4-pyridylCH$_2$ |

TABLE 31

| No | R¹ | R² | R³ |
| --- | --- | --- | --- |
| 751 | Et | 2-pyridyl | Me |
| 752 | Et | 2-pyridyl | Et |
| 753 | Et | 2-pyridyl | n-Pr |
| 754 | Et | 2-pyridyl | i-Pr |
| 755 | Et | 2-pyridyl | allyl |
| 756 | Et | 2-pyridyl | cinnamyl |
| 757 | Et | 2-pyridyl | 2-propynyl |
| 758 | Et | 2-pyridyl | 2-butynyl |
| 759 | Et | 2-pyridyl | 2-pyridyl |
| 760 | Et | 2-pyridyl | benzyl |
| 761 | Et | 2-pyridyl | 2-Cl-benzyl |
| 762 | Et | 2-pyridyl | 3-Cl-benzyl |
| 763 | Et | 2-pyridyl | 4-Cl-benzyl |
| 764 | Et | 2-pyridyl | 2-Me-benzyl |
| 765 | Et | 2-pyridyl | 3-Me-benzyl |
| 766 | Et | 2-pyridyl | 4-Me-benzyl |
| 767 | Et | 2-pyridyl | 2-MeO-benzyl |
| 768 | Et | 2-pyridyl | 3-MeO-benzyl |
| 769 | Et | 2-pyridyl | 4-MeO-benzyl |
| 770 | Et | 2-pyridyl | 2-Cl-4-MeO-benzyl |
| 771 | Et | 2-pyridyl | 3,4-(Cl)$_2$-benzyl |
| 772 | Et | 2-pyridyl | 2-Me-4-MeO-benzyl |
| 773 | Et | 2-pyridyl | α-Me-4-MeO-benzyl |
| 774 | Et | 2-pyridyl | 4-MeO-PhSO$_2$ |
| 775 | Et | 2-pyridyl | 4-pyridylCH$_2$ |

TABLE 32

| No | R¹ | R² | R³ |
| --- | --- | --- | --- |
| 776 | Et | benzyl | Me |
| 777 | Et | benzyl | Et |
| 778 | Et | benzyl | n-Pr |
| 779 | Et | benzyl | i-Pr |
| 780 | Et | benzyl | allyl |
| 781 | Et | benzyl | cinnamyl |
| 782 | Et | benzyl | 2-propynyl |
| 783 | Et | benzyl | 2-butynyl |
| 784 | Et | benzyl | 2-pyridyl |
| 785 | Et | benzyl | benzyl |
| 786 | Et | benzyl | 2-Cl-benzyl |
| 787 | Et | benzyl | 3-Cl-benzyl |
| 788 | Et | benzyl | 4-Cl-benzyl |
| 789 | Et | benzyl | 2-Me-benzyl |
| 790 | Et | benzyl | 3-Me-benzyl |
| 791 | Et | benzyl | 4-Me-benzyl |
| 792 | Et | benzyl | 2-MeO-benzyl |
| 793 | Et | benzyl | 3-MeO-benzyl |
| 794 | Et | benzyl | 4-MeO-benzyl |
| 795 | Et | benzyl | 2-Cl-4-MeO-benzyl |
| 796 | Et | benzyl | 3,4-(Cl)$_2$-benzyl |
| 797 | Et | benzyl | 2-Me-4-MeO-benzyl |
| 798 | Et | benzyl | α-Me-4-MeO-benzyl |
| 799 | Et | benzyl | 4-MeO-PhSO$_2$ |
| 800 | Et | benzyl | 4-pyridylCH$_2$ |

TABLE 33

| No | R¹ | R² | R³ |
| --- | --- | --- | --- |
| 801 | Et | 2-butynyl | Me |
| 802 | Et | 2-butynyl | Et |
| 803 | Et | 2-butynyl | n-Pr |
| 804 | Et | 2-butynyl | i-Pr |

TABLE 33-continued

| No | R¹ | R² | R³ |
|---|---|---|---|
| 805 | Et | 2-butynyl | allyl |
| 806 | Et | 2-butynyl | cinnamyl |
| 807 | Et | 2-butynyl | 2-propynyl |
| 808 | Et | 2-butynyl | 2-butynyl |
| 809 | Et | 2-butynyl | 2-pyridyl |
| 810 | Et | 2-butynyl | benzyl |
| 811 | Et | 2-butynyl | 2-Cl-benzyl |
| 812 | Et | 2-butynyl | 3-Cl-benzyl |
| 813 | Et | 2-butynyl | 4-Cl-benzyl |
| 814 | Et | 2-butynyl | 2-Me-benzyl |
| 815 | Et | 2-butynyl | 3-Me-benzyl |
| 816 | Et | 2-butynyl | 4-Me-benzyl |
| 817 | Et | 2-butynyl | 2-MeO-benzyl |
| 818 | Et | 2-butynyl | 3-MeO-benzyl |
| 819 | Et | 2-butynyl | 4-MeO-benzyl |
| 820 | Et | 2-butynyl | 2-Cl-4-MeO-benzyl |
| 821 | Et | 2-butynyl | 3,4-(Cl)$_2$-benzyl |
| 822 | Et | 2-butynyl | 2-Me-4-MeO-benzyl |
| 823 | Et | 2-butynyl | α-Me-4-MeO-benzyl |
| 824 | Et | 2-butynyl | 4-MeO-PhSO$_2$ |
| 825 | Et | 2-butynyl | 4-pyridylCH$_2$ |

TABLE 34

| No | R¹ | R² | R³ |
|---|---|---|---|
| 826 | Et | Ph | Me |
| 827 | Et | Ph | Et |
| 828 | Et | Ph | n-Pr |
| 829 | Et | Ph | i-Pr |
| 830 | Et | Ph | allyl |
| 831 | Et | Ph | cinnamyl |
| 832 | Et | Ph | 2-propynyl |
| 833 | Et | Ph | 2-butynyl |
| 834 | Et | Ph | 2-pyridyl |
| 835 | Et | Ph | benzyl |
| 836 | Et | Ph | 2-Cl-benzyl |
| 837 | Et | Ph | 3-Cl-benzyl |
| 838 | Et | Ph | 4-Cl-benzyl |
| 839 | Et | Ph | 2-Me-benzyl |
| 840 | Et | Ph | 3-Me-benzyl |
| 841 | Et | Ph | 4-Me-benzyl |
| 842 | Et | Ph | 2-MeO-benzyl |
| 843 | Et | Ph | 3-MeO-benzyl |
| 844 | Et | Ph | 4-MeO-benzyl |
| 845 | Et | Ph | 2-Cl-4-MeO-benzyl |
| 846 | Et | Ph | 3,4-(Cl)$_2$-benzyl |
| 847 | Et | Ph | 2-Me-4-MeO-benzyl |
| 848 | Et | Ph | α-Me-4-MeO-benzyl |
| 849 | Et | Ph | 4-MeO-PhSO$_2$ |
| 850 | Et | Ph | 4-pyridylCH$_2$ |

TABLE 35

| No | R¹ | R² | R³ |
|---|---|---|---|
| 851 | Et | 2-Cl-benzyl | Me |
| 852 | Et | 2-Cl-benzyl | Et |
| 853 | Et | 2-Cl-benzyl | n-Pr |
| 854 | Et | 2-Cl-benzyl | i-Pr |
| 855 | Et | 2-Cl-benzyl | allyl |
| 856 | Et | 2-Cl-benzyl | cinnamyl |
| 857 | Et | 2-Cl-benzyl | 2-propynyl |
| 858 | Et | 2-Cl-benzyl | 2-butynyl |
| 859 | Et | 2-Cl-benzyl | 2-pyridyl |
| 860 | Et | 2-Cl-benzyl | benzyl |
| 861 | Et | 2-Cl-benzyl | 2-Cl-benzyl |
| 862 | Et | 2-Cl-benzyl | 3-Cl-benzyl |
| 863 | Et | 2-Cl-benzyl | 4-Cl-benzyl |
| 864 | Et | 2-Cl-benzyl | 2-Me-benzyl |
| 865 | Et | 2-Cl-benzyl | 3-Me-benzyl |
| 866 | Et | 2-Cl-benzyl | 4-Me-benzyl |

TABLE 35-continued

| No | R¹ | R² | R³ |
|---|---|---|---|
| 867 | Et | 2-Cl-benzyl | 2-MeO-benzyl |
| 868 | Et | 2-Cl-benzyl | 3-MeO-benzyl |
| 869 | Et | 2-Cl-benzyl | 4-MeO-benzyl |
| 870 | Et | 2-Cl-benzyl | 2-Cl-4-MeO-benzyl |
| 871 | Et | 2-Cl-benzyl | 3,4-(Cl)$_2$-benzyl |
| 872 | Et | 2-Cl-benzyl | 2-Me-4-MeO-benzyl |
| 873 | Et | 2-Cl-benzyl | α-Me-4-MeO-benzyl |
| 874 | Et | 2-Cl-benzyl | 4-MeO-PhSO$_2$ |
| 875 | Et | 2-Cl-benzyl | 4-pyridylCH$_2$ |

TABLE 36

| No | R¹ | R² | R³ |
|---|---|---|---|
| 876 | Et | 3-Cl-benzyl | Me |
| 877 | Et | 3-Cl-benzyl | Et |
| 878 | Et | 3-Cl-benzyl | n-Pr |
| 879 | Et | 3-Cl-benzyl | i-Pr |
| 880 | Et | 3-Cl-benzyl | allyl |
| 881 | Et | 3-Cl-benzyl | cinnamyl |
| 882 | Et | 3-Cl-benzyl | 2-propynyl |
| 883 | Et | 3-Cl-benzyl | 2-butynyl |
| 884 | Et | 3-Cl-benzyl | 2-pyridyl |
| 885 | Et | 3-Cl-benzyl | benzyl |
| 886 | Et | 3-Cl-benzyl | 2-Cl-benzyl |
| 887 | Et | 3-Cl-benzyl | 3-Cl-benzyl |
| 888 | Et | 3-Cl-benzyl | 4-Cl-benzyl |
| 889 | Et | 3-Cl-benzyl | 2-Me-benzyl |
| 890 | Et | 3-Cl-benzyl | 3-Me-benzyl |
| 891 | Et | 3-Cl-benzyl | 4-Me-benzyl |
| 892 | Et | 3-Cl-benzyl | 2-MeO-benzyl |
| 893 | Et | 3-Cl-benzyl | 3-MeO-benzyl |
| 894 | Et | 3-Cl-benzyl | 4-MeO-benzyl |
| 895 | Et | 3-Cl-benzyl | 2-Cl-4-MeO-benzyl |
| 896 | Et | 3-Cl-benzyl | 3,4-(Cl)$_2$-benzyl |
| 897 | Et | 3-Cl-benzyl | 2-Me-4-MeO-benzyl |
| 898 | Et | 3-Cl-benzyl | α-Me-4-MeO-benzyl |
| 899 | Et | 3-Cl-benzyl | 4-MeO-PhSO$_2$ |
| 900 | Et | 3-Cl-benzyl | 4-pyridylCH$_2$ |

TABLE 37

| No | R¹ | R² | R³ |
|---|---|---|---|
| 901 | Et | 4-Cl-benzyl | Me |
| 902 | Et | 4-Cl-benzyl | Et |
| 903 | Et | 4-Cl-benzyl | n-Pr |
| 904 | Et | 4-Cl-benzyl | i-Pr |
| 905 | Et | 4-Cl-benzyl | allyl |
| 906 | Et | 4-Cl-benzyl | cinnamyl |
| 907 | Et | 4-Cl-benzyl | 2-propynyl |
| 908 | Et | 4-Cl-benzyl | 2-butynyl |
| 909 | Et | 4-Cl-benzyl | 2-pyridyl |
| 910 | Et | 4-Cl-benzyl | benzyl |
| 911 | Et | 4-Cl-benzyl | 2-Cl-benzyl |
| 912 | Et | 4-Cl-benzyl | 3-Cl-benzyl |
| 913 | Et | 4-Cl-benzyl | 4-Cl-benzyl |
| 914 | Et | 4-Cl-benzyl | 2-Me-benzyl |
| 915 | Et | 4-Cl-benzyl | 3-Me-benzyl |
| 916 | Et | 4-Cl-benzyl | 4-Me-benzyl |
| 917 | Et | 4-Cl-benzyl | 2-MeO-benzyl |
| 918 | Et | 4-Cl-benzyl | 3-MeO-benzyl |
| 919 | Et | 4-Cl-benzyl | 4-MeO-benzyl |
| 920 | Et | 4-Cl-benzyl | 2-Cl-4-MeO-benzyl |
| 921 | Et | 4-Cl-benzyl | 3,4-(Cl)$_2$-benzyl |
| 922 | Et | 4-Cl-benzyl | 2-Me-4-MeO-benzyl |
| 923 | Et | 4-Cl-benzyl | α-Me-4-MeO-benzyl |
| 924 | Et | 4-Cl-benzyl | 4-MeO-PhSO$_2$ |
| 925 | Et | 4-Cl-benzyl | 4-pyridylCH$_2$ |

TABLE 38

| No | R¹ | R² | R³ |
|---|---|---|---|
| 926 | Et | 2-Me-benzyl | Me |
| 927 | Et | 2-Me-benzyl | Et |
| 928 | Et | 2-Me-benzyl | n-Pr |
| 929 | Et | 2-Me-benzyl | i-Pr |
| 930 | Et | 2-Me-benzyl | allyl |
| 931 | Et | 2-Me-benzyl | cinnamyl |
| 932 | Et | 2-Me-benzyl | 2-propynyl |
| 933 | Et | 2-Me-benzyl | 2-butynyl |
| 934 | Et | 2-Me-benzyl | 2-pyridyl |
| 935 | Et | 2-Me-benzyl | benzyl |
| 936 | Et | 2-Me-benzyl | 2-Cl-benzyl |
| 937 | Et | 2-Me-benzyl | 3-Cl-benzyl |
| 938 | Et | 2-Me-benzyl | 4-Cl-benzyl |
| 939 | Et | 2-Me-benzyl | 2-Me-benzyl |
| 940 | Et | 2-Me-benzyl | 3-Me-benzyl |
| 941 | Et | 2-Me-benzyl | 4-Me-benzyl |
| 942 | Et | 2-Me-benzyl | 2-MeO-benzyl |
| 943 | Et | 2-Me-benzyl | 3-MeO-benzyl |
| 944 | Et | 2-Me-benzyl | 4-MeO-benzyl |
| 945 | Et | 2-Me-benzyl | 2-Cl-4-MeO-benzyl |
| 946 | Et | 2-Me-benzyl | 3,4-(Cl)₂-benzyl |
| 947 | Et | 2-Me-benzyl | 2-Me-4-MeO-benzyl |
| 948 | Et | 2-Me-benzyl | α-Me-4-MeO-benzyl |
| 949 | Et | 2-Me-benzyl | 4-MeO-PhSO₂ |
| 950 | Et | 2-Me-benzyl | 4-pyridylCH₂ |

TABLE 39

| No | R¹ | R² | R³ |
|---|---|---|---|
| 951 | Et | 3-Me-benzyl | Me |
| 952 | Et | 3-Me-benzyl | Et |
| 953 | Et | 3-Me-benzyl | n-Pr |
| 954 | Et | 3-Me-benzyl | i-Pr |
| 955 | Et | 3-Me-benzyl | allyl |
| 956 | Et | 3-Me-benzyl | cinnamyl |
| 957 | Et | 3-Me-benzyl | 2-propynyl |
| 958 | Et | 3-Me-benzyl | 2-butynyl |
| 959 | Et | 3-Me-benzyl | 2-pyridyl |
| 960 | Et | 3-Me-benzyl | benzyl |
| 961 | Et | 3-Me-benzyl | 2-Cl-benzyl |
| 962 | Et | 3-Me-benzyl | 3-Cl-benzyl |
| 963 | Et | 3-Me-benzyl | 4-Cl-benzyl |
| 964 | Et | 3-Me-benzyl | 2-Me-benzyl |
| 965 | Et | 3-Me-benzyl | 3-Me-benzyl |
| 966 | Et | 3-Me-benzyl | 4-Me-benzyl |
| 967 | Et | 3-Me-benzyl | 2-MeO-benzyl |
| 968 | Et | 3-Me-benzyl | 3-MeO-benzyl |
| 969 | Et | 3-Me-benzyl | 4-MeO-benzyl |
| 970 | Et | 3-Me-benzyl | 2-Cl-4-MeO-benzyl |
| 971 | Et | 3-Me-benzyl | 3,4-(Cl)₂-benzyl |
| 972 | Et | 3-Me-benzyl | 2-Me-4-MeO-benzyl |
| 973 | Et | 3-Me-benzyl | α-Me-4-MeO-benzyl |
| 974 | Et | 3-Me-benzyl | 4-MeO-PhSO₂ |
| 975 | Et | 3-Me-benzyl | 4-pyridylCH₂ |

TABLE 40

| No | R¹ | R² | R³ |
|---|---|---|---|
| 976 | Et | 4-Me-benzyl | Me |
| 977 | Et | 4-Me-benzyl | Et |
| 978 | Et | 4-Me-benzyl | n-Pr |
| 979 | Et | 4-Me-benzyl | i-Pr |
| 980 | Et | 4-Me-benzyl | allyl |
| 981 | Et | 4-Me-benzyl | cinnamyl |
| 982 | Et | 4-Me-benzyl | 2-propynyl |
| 983 | Et | 4-Me-benzyl | 2-butynyl |
| 984 | Et | 4-Me-benzyl | 2-pyridyl |
| 985 | Et | 4-Me-benzyl | benzyl |
| 986 | Et | 4-Me-benzyl | 2-Cl-benzyl |
| 987 | Et | 4-Me-benzyl | 3-Cl-benzyl |
| 988 | Et | 4-Me-benzyl | 4-Cl-benzyl |
| 989 | Et | 4-Me-benzyl | 2-Me-benzyl |
| 990 | Et | 4-Me-benzyl | 3-Me-benzyl |
| 991 | Et | 4-Me-benzyl | 4-Me-benzyl |
| 992 | Et | 4-Me-benzyl | 2-MeO-benzyl |
| 993 | Et | 4-Me-benzyl | 3-MeO-benzyl |
| 994 | Et | 4-Me-benzyl | 4-MeO-benzyl |
| 995 | Et | 4-Me-benzyl | 2-Cl-4-MeO-benzyl |
| 996 | Et | 4-Me-benzyl | 3,4-(Cl)₂-benzyl |
| 997 | Et | 4-Me-benzyl | 2-Me-4-MeO-benzyl |
| 998 | Et | 4-Me-benzyl | α-Me-4-MeO-benzyl |
| 999 | Et | 4-Me-benzyl | 4-MeO-PhSO₂ |
| 1000 | Et | 4-Me-benzyl | 4-pyridylCH₂ |

TABLE 41

| No | R¹ | R² | R³ |
|---|---|---|---|
| 1001 | Et | 2-MeO-benzyl | Me |
| 1002 | Et | 2-MeO-benzyl | Et |
| 1003 | Et | 2-MeO-benzyl | n-Pr |
| 1004 | Et | 2-MeO-benzyl | i-Pr |
| 1005 | Et | 2-MeO-benzyl | allyl |
| 1006 | Et | 2-MeO-benzyl | cinnamyl |
| 1007 | Et | 2-MeO-benzyl | 2-propynyl |
| 1008 | Et | 2-MeO-benzyl | 2-butynyl |
| 1009 | Et | 2-MeO-benzyl | 2-pyridyl |
| 1010 | Et | 2-MeO-benzyl | benzyl |
| 1011 | Et | 2-MeO-benzyl | 2-Cl-benzyl |
| 1012 | Et | 2-MeO-benzyl | 3-Cl-benzyl |
| 1013 | Et | 2-MeO-benzyl | 4-Cl-benzyl |
| 1014 | Et | 2-MeO-benzyl | 2-Me-benzyl |
| 1015 | Et | 2-MeO-benzyl | 3-Me-benzyl |
| 1016 | Et | 2-MeO-benzyl | 4-Me-benzyl |
| 1017 | Et | 2-MeO-benzyl | 2-MeO-benzyl |
| 1018 | Et | 2-MeO-benzyl | 3-MeO-benzyl |
| 1019 | Et | 2-MeO-benzyl | 4-MeO-benzyl |
| 1020 | Et | 2-MeO-benzyl | 2-Cl-4-MeO-benzyl |
| 1021 | Et | 2-MeO-benzyl | 3,4-(Cl)₂-benzyl |
| 1022 | Et | 2-MeO-benzyl | 2-Me-4-MeO-benzyl |
| 1023 | Et | 2-MeO-benzyl | α-Me-4-MeO-benzyl |
| 1024 | Et | 2-MeO-benzyl | 4-MeO-PhSO₂ |
| 1025 | Et | 2-MeO-benzyl | 4-pyridylCH₂ |

TABLE 42

| No | R¹ | R² | R³ |
|---|---|---|---|
| 1026 | Et | 3-MeO-benzyl | Me |
| 1027 | Et | 3-MeO-benzyl | Et |
| 1028 | Et | 3-MeO-benzyl | n-Pr |
| 1029 | Et | 3-MeO-benzyl | i-Pr |
| 1030 | Et | 3-MeO-benzyl | aiiyi |
| 1031 | Et | 3-MeO-benzyl | cinnamyl |
| 1032 | Et | 3-MeO-benzyl | 2-propynyl |
| 1033 | Et | 3-MeO-benzyl | 2-butynyl |
| 1034 | Et | 3-MeO-benzyl | 2-pyridyl |
| 1035 | Et | 3-MeO-benzyl | benzyl |
| 1036 | Et | 3-MeO-benzyl | 2-Cl-benzyl |
| 1037 | Et | 3-MeO-benzyl | 3-Cl-benzyl |
| 1038 | Et | 3-MeO-benzyl. | 4-Cl-benzyl |
| 1039 | Et | 3-MeO-benzyl | 2-Me-benzyl |
| 1040 | Et | 3-MeO-benzyl | 3-Me-benzyl |
| 1041 | Et | 3-MeO-benzyl | 4-Me-benzyl |
| 1042 | Et | 3-MeO-benzyl | 2-MeO-benzyl |
| 1043 | Et | 3-MeO-benzyl | 3-MeO-benzyl |
| 1044 | Et | 3-MeO-benzyl | 4-MeO-benzyl |
| 1045 | Et | 3-MeO-benzyl | 2-Cl-4-MeO-benzyl |
| 1046 | Et | 3-MeO-benzyl | 3,4-(Cl)₂-benzyl |
| 1047 | Et | 3-MeO-benzyl | 2-Me-4-MeO-benzyl |
| 1048 | Et | 3-MeO-benzyl | α-Me-4-MeO-benzyl |

TABLE 42-continued

| No | R¹ | R² | R³ |
|---|---|---|---|
| 1049 | Et | 3-MeO-benzyl | 4-MeO-PhSO$_2$ |
| 1050 | Et | 3-MeO-benzyl | 4-pyridylCH$_2$ |

TABLE 43

| No | R¹ | R² | R³ |
|---|---|---|---|
| 1051 | Et | 4-MeO-benzyl | Me |
| 1052 | Et | 4-MeO-benzyl | Et |
| 1053 | Et | 4-MeO-benzyl | n-Pr |
| 1054 | Et | 4-MeO-benzyl | i-Pr |
| 1055 | Et | 4-MeO-benzyl | allyl |
| 1056 | Et | 4-MeO-benzyl | cinnamyl |
| 1057 | Et | 4-MeO-benzyl | 2-propynyl |
| 1058 | Et | 4-MeO-benzyl | 2-butynyl |
| 1059 | Et | 4-MeO-benzyl | 2-pyridyl |
| 1060 | Et | 4-MeO-benzyl | benzyl |
| 1061 | Et | 4-MeO-benzyl | 2-Cl-benzyl |
| 1062 | Et | 4-MeO-benzyl | 3-Cl-benzyl |
| 1063 | Et | 4-MeO-benzyl | 4-Cl-benzyl |
| 1064 | Et | 4-MeO-benzyl | 2-Me-benzyl |
| 1065 | Et | 4-MeO-benzyl | 3-Me-benzyl |
| 1066 | Et | 4-MeO-benzyl | 4-Me-benzyl |
| 1067 | Et | 4-MeO-benzyl | 2-MeO-benzyl |
| 1068 | Et | 4-MeO-benzyl | 3-MeO-benzyl |
| 1069 | Et | 4-MeO-benzyl | 4-MeO-benzyl |
| 1070 | Et | 4-MeO-benzyl | 2-Cl-4-MeO-benzyl |
| 1071 | Et | 4-MeO-benzyl | 3,4-(Cl)$_2$-benzyl |
| 1072 | Et | 4-MeO-benzyl | 2-Me-4-MeO-benzyl |
| 1073 | Et | 4-MeO-benzyl | α-Me-4-MeO-benzyl |
| 1074 | Et | 4-MeO-benzyl | 4-MeO-PhSO$_2$ |
| 1075 | Et | 4-MeO-benzyl | 4-pyridylCH$_2$ |

TABLE 44

| No | R¹ | R² | R³ |
|---|---|---|---|
| 1076 | Et | 3,4-(Cl)$_2$-benzyl | Me |
| 1077 | Et | 3,4-(Cl)$_2$-benzyl | Et |
| 1078 | Et | 3,4-(Cl)$_2$-benzyl | n-Pr |
| 1079 | Et | 3,4-(Cl)$_2$-benzyl | i-Pr |
| 1080 | Et | 3,4-(Cl)$_2$-benzyl | allyl |
| 1081 | Et | 3,4-(Cl)$_2$-benzyl | cinnamyl |
| 1082 | Et | 3,4-(Cl)$_2$-benzyl | 2-propynyl |
| 1083 | Et | 3,4-(Cl)$_2$-benzyl | 2-butynyl |
| 1084 | Et | 3,4-(Cl)$_2$-benzyl | 2-pyridyl |
| 1085 | Et | 3,4-(Cl)$_2$-benzyl | benzyl |
| 1086 | Et | 3,4-(Cl)$_2$-benzyl | 2-Cl-benzyl |
| 1087 | Et | 3,4-(Cl)$_2$-benzyl | 3-Cl-benzyl |
| 1088 | Et | 3,4-(Cl)$_2$-benzyl | 4-Cl-benzyl |
| 1089 | Et | 3,4-(Cl)$_2$-benzyl | 2-Me-benzyl |
| 1090 | Et | 3,4-(Cl)$_2$-benzyl | 3-Me-benzyl |
| 1091 | Et | 3,4-(Cl)$_2$-benzyl | 4-Me-benzyl |
| 1092 | Et | 3,4-(Cl)$_2$-benzyl | 2-MeO-benzyl |
| 1093 | Et | 3,4-(Cl)$_2$-benzyl | 3-MeO-benzyl |
| 1094 | Et | 3,4-(Cl)$_2$-benzyl | 4-MeO-benzyl |
| 1095 | Et | 3,4-(Cl)$_2$-benzyl | 2-Cl-4-MeO-benzyl |
| 1096 | Et | 3,4-(Cl)$_2$-benzyl | 3,4-(Cl)$_2$-benzyl |
| 1097 | Et | 3,4-(Cl)$_2$-benzyl | 2-Me-4-MeO-benzyl |
| 1098 | Et | 3,4-(Cl)$_2$-benzyl | α-Me-4-MeO-benzyl |
| 1099 | Et | 3,4-(Cl)$_2$-benzyl | 4-MeO-PhSO$_2$ |
| 1100 | Et | 3,4-(Cl)$_2$-benzyl | 4-pyridylCH$_2$ |

TABLE 45

| No | R¹ | R² | R³ |
|---|---|---|---|
| 1101 | Et | 2-Cl-4-MeO-benzyl | Me |
| 1102 | Et | 2-Cl-4-MeO-benzyl | Et |
| 1103 | Et | 2-Cl-4-MeO-benzyl | n-Pr |

TABLE 45-continued

| No | R¹ | R² | R³ |
|---|---|---|---|
| 1104 | Et | 2-Cl-4-MeO-benzyl | i-Pr |
| 1105 | Et | 2-Cl-4-MeO-benzyl | allyl |
| 1106 | Et | 2-Cl-4-MeO-benzyl | cinnamyl |
| 1107 | Et | 2-Cl-4-MeO-benzyl | 2-propynyl |
| 1108 | Et | 2-Cl-4-MeO-benzyl | 2-butynyl |
| 1109 | Et | 2-Cl-4-MeO-benzyl | 2-pyridyl |
| 1110 | Et | 2-Cl-4-MeO-benzyl | benzyl |
| 1111 | Et | 2-Cl-4-MeO-benzyl | 2-Cl-benzyl |
| 1112 | Et | 2-Cl-4-MeO-benzyl | 3-Cl-benzyl |
| 1113 | Et | 2-Cl-4-MeO-benzyl | 4-Cl-benzyl |
| 1114 | Et | 2-Cl-4-MeO-benzyl | 2-Me-benzyl |
| 1115 | Et | 2-Cl-4-MeO-benzyl | 3-Me-benzyl |
| 1116 | Et | 2-Cl-4-MeO-benzyl | 4-Me-benzyl |
| 1117 | Et | 2-Cl-4-MeO-benzyl | 2-MeO-benzyl |
| 1118 | Et | 2-Cl-4-MeO-benzyl | 3-MeO-benzyl |
| 1119 | Et | 2-Cl-4-MeO-benzyl | 4-MeO-benzyl |
| 1120 | Et | 2-Cl-4-MeO-benzyl | 2-Cl-4-MeO-benzyl |
| 1121 | Et | 2-Cl-4-MeO-benzyl | 3,4-(Cl)$_2$-benzyl |
| 1122 | Et | 2-Cl-4-MeO-benzyl | 2-Me-4-MeO-benzyl |
| 1123 | Et | 2-Cl-4-MeO-benzyl | α-Me-4-MeO-benzyl |
| 1124 | Et | 2-Cl-4-MeO-benzyl | 4-MeO-PhSO$_2$ |
| 1125 | Et | 2-Cl-4-MeO-benzyl | 4-pyridylCH$_2$ |

TABLE 46

| No | R¹ | R² | R³ |
|---|---|---|---|
| 1126 | Et | 2-pyridylCH$_2$ | Me |
| 1127 | Et | 2-pyridylCH$_2$ | Et |
| 1128 | Et | 2-pyridylCH$_2$ | n-Pr |
| 1129 | Et | 2-pyridylCH$_2$ | i-Pr |
| 1130 | Et | 2-pyridylCH$_2$ | allyl |
| 1131 | Et | 2-pyridylCH$_2$ | cinnamyl |
| 1132 | Et | 2-pyridylCH$_2$ | 2-propynyl |
| 1133 | Et | 2-pyridylCH$_2$ | 2-butynyl |
| 1134 | Et | 2-pyridylCH$_2$ | 2-pyridyl |
| 1135 | Et | 2-pyridylCH$_2$ | benzyl |
| 1136 | Et | 2-pyridylCH$_2$ | 2-Cl-benzyl |
| 1137 | Et | 2-pyridylCH$_2$ | 3-Cl-benzyl |
| 1138 | Et | 2-pyridylCH$_2$ | 4-Cl-benzyl |
| 1139 | Et | 2-pyridylCH$_2$ | 2-Me-benzyl |
| 1140 | Et | 2-pyridylCH$_2$ | 3-Me-benzyl |
| 1141 | Et | 2-pyridylCH$_2$ | 4-Me-benzyl |
| 1142 | Et | 2-pyridylCH$_2$ | 2-MeO-benzyl |
| 1143 | Et | 2-pyridylCH$_2$ | 3-MeO-benzyl |
| 1144 | Et | 2-pyridylCH$_2$ | 4-MeO-benzyl |
| 1145 | Et | 2-pyridylCH$_2$ | 2-Cl-4-MeO-benzyl |
| 1146 | Et | 2-pyridylCH$_2$ | 3,4-(Cl)$_2$-benzyl |
| 1147 | Et | 2-pyridylCH$_2$ | 2-Me-4-MeO-benzyl |
| 1148 | Et | 2-pyridylCH$_2$ | α-Me-4-MeO-benzyl |
| 1149 | Et | 2-pyridylCH$_2$ | 4-MeO-PhSO$_2$ |
| 1150 | Et | 2-pyridylCH$_2$ | 4-pyridylCH$_2$ |

TABLE 47

| No | R¹ | R² | R³ |
|---|---|---|---|
| 1151 | Et | 3-pyridylCH$_2$ | Me |
| 1152 | Et | 3-pyridylCH$_2$ | Et |
| 1153 | Et | 3-pyridylCH$_2$ | n-Pr |
| 1154 | Et | 3-pyridylCH$_2$ | i-Pr |
| 1155 | Et | 3-pyridylCH$_2$ | allyl |
| 1156 | Et | 3-pyridylCH$_2$ | cinnamyl |
| 1157 | Et | 3-pyridylCH$_2$ | 2-propynyl |
| 1158 | Et | 3-pyridylCH$_2$ | 2-butynyl |
| 1159 | Et | 3-pyridylCH$_2$ | 2-pyridyl |
| 1160 | Et | 3-pyridylCH$_2$ | benzyl |
| 1161 | Et | 3-pyridylCH$_2$ | 2-Cl-benzyl |
| 1162 | Et | 3-pyridylCH$_2$ | 3-Cl-benzyl |
| 1163 | Et | 3-pyridylCH$_2$ | 4-Cl-benzyl |
| 1164 | Et | 3-pyridylCH$_2$ | 2-Me-benzyl |
| 1165 | Et | 3-pyridylCH$_2$ | 3-Me-benzyl |

TABLE 47-continued

| No | R¹ | R² | R³ |
|---|---|---|---|
| 1166 | Et | 3-pyridylCH₂ | 4-Me-benzyl |
| 1167 | Et | 3-pyridylCH₂ | 2-MeO-benzyl |
| 1168 | Et | 3-pyridylCH₂ | 3-MeO-benzyl |
| 1169 | Et | 3-pyridylCH₂ | 4-MeO-benzyl |
| 1170 | Et | 3-pyridylCH₂ | 2-Cl-4-MeO-benzyl |
| 1171 | Et | 3-pyridylCH₂ | 3,4-(Cl)₂-benzyl |
| 1172 | Et | 3-pyridylCH₂ | 2-Me-4-MeO-benzyl |
| 1173 | Et | 3-pyridylCH₂ | α-Me-4-MeO-benzyl |
| 1174 | Et | 3-pyridylCH₂ | 4-MeO-PhSO₂ |
| 1175 | Et | 3-pyridylCH₂ | 4-pyridylCH₂ |

TABLE 48

| No | R¹ | R² | R³ |
|---|---|---|---|
| 1176 | Et | 4-pyridylCH₂ | Me |
| 1177 | Et | 4-pyridylCH₂ | Et |
| 1178 | Et | 4-pyridylCH₂ | n-Pr |
| 1179 | Et | 4-pyridylCH₂ | i-Pr |
| 1180 | Et | 4-pyridylCH₂ | allyl |
| 1181 | Et | 4-pyridylCH₂ | cinnamyl |
| 1182 | Et | 4-pyridylCH₂ | 2-propynyl |
| 1183 | Et | 4-pyridylCH₂ | 2-butynyl |
| 1184 | Et | 4-pyridylCH₂ | 2-pyridyl |
| 1185 | Et | 4-pyridylCH₂ | benzyl |
| 1186 | Et | 4-pyridylCH₂ | 2-Cl-benzyl |
| 1187 | Et | 4-pyridylCH₂ | 3-Cl-benzyl |
| 1188 | Et | 4-pyridylCH₂ | 4-Cl-benzyl |
| 1189 | Et | 4-pyridylCH₂ | 2-Me-benzyl |
| 1190 | Et | 4-pyridylCH₂ | 3-Me-benzyl |
| 1191 | Et | 4-pyridylCH₂ | 4-Me-benzyl |
| 1192 | Et | 4-pyridylCH₂ | 2-MeO-benzyl |
| 1193 | Et | 4-pyridylCH₂ | 3-MeO-benzyl |
| 1194 | Et | 4-pyridylCH₂ | 4-MeO-benzyl |
| 1195 | Et | 4-pyridylCH₂ | 2-Cl-4-MeO-benzyl |
| 1196 | Et | 4-pyridylCH₂ | 3,4-(Cl)₂-benzyl |
| 1197 | Et | 4-pyridylCH₂ | 2-Me-4-MeO-benzyl |
| 1198 | Et | 4-pyridylCH₂ | α-Me-4-MeO-benzyl |
| 1199 | Et | 4-pyridylCH₂ | 4-MeO-PhSO₂ |
| 1200 | Et | 4-pyridylCH₂ | 4-pyridylCH₂ |

TABLE 49

| No | R¹ | R² | R³ |
|---|---|---|---|
| 1201 | Pr | Me | Me |
| 1202 | Pr | Me | allyl |
| 1203 | Pr | Me | benzyl |
| 1204 | Pr | Me | 2-Cl-benzyl |
| 1205 | Pr | Me | 4-Cl-benzyl |
| 1206 | Pr | Me | 2-Me-benzyl |
| 1207 | Pr | Me | 4-Me-benzyl |
| 1208 | Pr | Me | 2-Cl-4-MeO-benzyl |
| 1209 | Pr | Me | 2-MeO-benzyl |
| 1210 | Pr | Me | 4-MeO-benzyl |
| 1211 | Pr | allyl | Me |
| 1212 | Pr | allyl | allyl |
| 1213 | Pr | allyl | benzyl |
| 1214 | Pr | allyl | 2-Cl-benzyl |
| 1215 | Pr | allyl | 4-Cl-benzyl |
| 1216 | Pr | allyl | 2-Me-benzyl |
| 1217 | Pr | allyl | 4-Me-benzyl |
| 1218 | Pr | allyl | 2-Cl-4-MeO-benzyl |
| 1219 | Pr | allyl | 2-MeO-benzyl |
| 1220 | Pr | allyl | 4-MeO-benzyl |
| 1221 | Pr | 2-propynyl | Me |
| 1222 | Pr | 2-propynyl | allyl |
| 1223 | Pr | 2-propynyl | benzyl |
| 1224 | Pr | 2-propynyl | 2-Cl-benzy |
| 1225 | Pr | 2-propynyl | 4-Cl-benzyl |

TABLE 50

| No | R¹ | R² | R³ |
|---|---|---|---|
| 1226 | Pr | 2-propynyl | 2-Me-benzyl |
| 1227 | Pr | 2-propynyl | 4-Me-benzyl |
| 1228 | Pr | 2-propynyl | 2-Cl-4-MeO-benzyl |
| 1229 | Pr | 2-propynyl | 2-MeO-benzyl |
| 1230 | Pr | 2-propynyl | 4-MeO-benzyl |
| 1231 | Pr | benzyl | Me |
| 1232 | Pr | benzyl | allyl |
| 1233 | Pr | benzyl | benzyl |
| 1234 | Pr | benzyl | 2-Cl-benzyl |
| 1235 | Pr | benzyl | 4-Cl-benzyl |
| 1236 | Pr | benzyl | 2-Me-benzyl |
| 1237 | Pr | benzyl | 4-Me-benzyl |
| 1238 | Pr | benzyl | 2-Cl-4-MeO-benzyl |
| 1239 | Pr | benzyl | 2-MeO-benzyl |
| 1240 | Pr | benzyl | 4-MeO-benzyl |
| 1241 | Pr | 4-Me-benzyl | Me |
| 1242 | Pr | 4-Me-benzyl | allyl |
| 1243 | Pr | 4-Me-benzyl | benzyl |
| 1244 | Pr | 4-Me-benzyl | 2-Cl-benzyl |
| 1245 | Pr | 4-Me-benzyl | 4-Cl-benzyl |
| 1246 | Pr | 4-Me-benzyl | 2-Me-benzyl |
| 1247 | Pr | 4-Me-benzyl | 4-Me-benzyl |
| 1248 | Pr | 4-Me-benzyl | 2-Cl-4-MeO-benzyl |
| 1249 | Pr | 4-Me-benzyl | 2-MeO-benzyl |
| 1250 | Pr | 4-Me-benzyl | 4-MeO-benzyl |

TABLE 51

| No | R¹ | R² | R³ |
|---|---|---|---|
| 1251 | Pr | 4-Cl-benzyl | Me |
| 1252 | Pr | 4-Cl-benzyl | allyl |
| 1253 | Pr | 4-Cl-benzyl | benzyl |
| 1254 | Pr | 4-Cl-benzyl | 2-Cl-benzyl |
| 1255 | Pr | 4-Cl-benzyl | 4-Cl-benzyl |
| 1256 | Pr | 4-Cl-benzyl | 2-Me-benzyl |
| 1257 | Pr | 4-Cl-benzyl | 4-Me-benzyl |
| 1258 | Pr | 4-Cl-benzyl | 2-Cl-4-MeO-benzyl |
| 1259 | Pr | 4-Cl-benzyl | 2-MeO-benzyl |
| 1260 | Pr | 4-Cl-benzyl | 4-MeO-benzyl |
| 1261 | Pr | 4-MeO-benzyl | Me |
| 1262 | Pr | 4-MeO-benzyl | allyl |
| 1263 | Pr | 4-MeO-benzyl | benzyl |
| 1264 | Pr | 4-MeO-benzyl | 2-Cl-benzyl |
| 1265 | Pr | 4-MeO-benzyl | 4-Cl-benzyl |
| 1266 | Pr | 4-MeO-benzyl | 2-Me-benzyl |
| 1267 | Pr | 4-MeO-benzyl | 4-Me-benzyl |
| 1268 | Pr | 4-MeO-benzyl | 2-Cl-4-MeO-benzyl |
| 1269 | Pr | 4-MeO-benzyl | 2-MeO-benzyl |
| 1270 | Pr | 4-MeO-benzyl | 4-MeO-benzyl |
| 1271 | Pr | 2-pyridylCH₂ | Me |
| 1272 | Pr | 2-pyridylCH₂ | allyl |
| 1273 | Pr | 2-pyridylCH₂ | benzyl |
| 1274 | Pr | 2-pyridylCH₂ | 2-Cl-benzyl |
| 1275 | Pr | 2-pyridylCH₂ | 4-Cl-benzyl |

TABLE 52

| No | R¹ | R² | R³ |
|---|---|---|---|
| 1276 | Pr | 2-pyridylCH₂ | 2-Me-benzyl |
| 1277 | Pr | 2-pyridylCH₂ | 4-Me-benzyl |
| 1278 | Pr | 2-pyridylCH₂ | 2-Cl-4-MeO-benzyl |
| 1279 | Pr | 2-pyridylCH₂ | 2-MeO-benzyl |
| 1280 | Pr | 2-pyridylCH₂ | 4-MeO-benzyl |
| 1281 | Pr | 3-pyridylCH₂ | Me |
| 1282 | Pr | 3-pyridylCH₂ | allyl |
| 1283 | Pr | 3-pyridylCH₂ | benzyl |
| 1284 | Pr | 3-pyridylCH₂ | 2-Cl-benzyl |
| 1285 | Pr | 3-pyridylCH₂ | 4-Cl-benzyl |
| 1286 | Pr | 3-pyridylCH₂ | 2-Me-benzyl |
| 1287 | Pr | 3-pyridylCH₂ | 4-Me-benzyl |

TABLE 52-continued

| No | R¹ | R² | R³ |
|---|---|---|---|
| 1288 | Pr | 3-pyridylCH$_2$ | 2-Cl-4-MeO-benzyl |
| 1289 | Pr | 3-pyridylCH$_2$ | 2-MeO-benzyl |
| 1290 | Pr | 3-pyridylCH$_2$ | 4-MeO-benzyl |
| 1291 | Pr | 4-pyridylCH$_2$ | Me |
| 1292 | Pr | 4-pyridylCH$_2$ | allyl |
| 1293 | Pr | 4-pyridylCH$_2$ | benzyl |
| 1294 | Pr | 4-pyridylCH$_2$ | 2-Cl-benzyl |
| 1295 | Pr | 4-pyridylCH$_2$ | 4-Cl-benzyl |
| 1296 | Pr | 4-pyridylCH$_2$ | 2-Me-benzyl |
| 1297 | Pr | 4-pyridylCH$_2$ | 4-Me-benzyl |
| 1298 | Pr | 4-pyridylCH$_2$ | 2-Cl-4-MeO-benzyl |
| 1299 | Pr | 4-pyridylCH$_2$ | 2-MeO-benzyl |
| 1300 | Pr | 4-pyridylCH$_2$ | 4-MeO-benzyl |

TABLE 53

| No | R¹ | R² | R³ |
|---|---|---|---|
| 1301 | Ph | Me | Me |
| 1302 | Ph | Me | allyl |
| 1303 | Ph | Me | benzyl |
| 1304 | Ph | Me | 2-Cl-benzyl |
| 1305 | Ph | Me | 4-Cl-benzyl |
| 1306 | Ph | Me | 2-Me-benzyl |
| 1307 | Ph | Me | 4-Me-benzyl |
| 1308 | Ph | Me | 2-Cl-4-MeO-benzyl |
| 1309 | Ph | Me | 2-MeO-benzyl |
| 1310 | Ph | Me | 4-MeO-benzyl |
| 1311 | Ph | allyl | Me |
| 1312 | Ph | allyl | allyl |
| 1313 | Ph | allyl | benzyl |
| 1314 | Ph | allyl | 2-Cl-benzyl |
| 1315 | Ph | allyl | 4-Cl-benzyl |
| 1316 | Ph | allyl | 2-Me-benzyl |
| 1317 | Ph | allyl | 4-Me-benzyl |
| 1318 | Ph | allyl | 2-Cl-4-MeO-benzyl |
| 1319 | Ph | allyl | 2-MeO-benzyl |
| 1320 | Ph | allyl | 4-MeO-benzyl |
| 1321 | Ph | 2-propynyl | Me |
| 1322 | Ph | 2-propynyl | allyl |
| 1323 | Ph | 2-propynyl | benzyl |
| 1324 | Ph | 2-propynyl | 2-Cl-benzy |
| 1325 | Ph | 2-propynyl | 4-Cl-benzyl |

TABLE 54

| No | R¹ | R² | R³ |
|---|---|---|---|
| 1326 | Ph | 2-propynyl | 2-Me-benzyl |
| 1327 | Ph | 2-propynyl | 4-Me-benzyl |
| 1328 | Ph | 2-propynyl | 2-Cl-4-MeO-benzyl |
| 1329 | Ph | 2-propynyl | 2-MeO-benzyl |
| 1330 | Ph | 2-propynyl | 4-MeO-benzyl |
| 1331 | Ph | benzyl | Me |
| 1332 | Ph | benzyl | allyl |
| 1333 | Ph | benzyl | benzyl |
| 1334 | Ph | benzyl | 2-Cl-benzyl |
| 1335 | Ph | benzyl | 4-Cl-benzyl |
| 1336 | Ph | benzyl | 2-Me-benzyl |
| 1337 | Ph | benzyl | 4-Me-benzyl |
| 1338 | Ph | benzyl | 2-Cl-4-MeO-benzyl |
| 1339 | Ph | benzyl | 2-MeO-benzyl |
| 1340 | Ph | benzyl | 4-MeO-benzyl |
| 1341 | Ph | 4-Me-benzyl | Me |
| 1342 | Ph | 4-Me-benzyl | allyl |
| 1343 | Ph | 4-Me-benzyl | benzyl |
| 1344 | Ph | 4-Me-benzyl | 2-Cl-benzyl |
| 1345 | Ph | 4-Me-benzyl | 4-Cl-benzyl |
| 1346 | Ph | 4-Me-benzyl | 2-Me-benzyl |
| 1347 | Ph | 4-Me-benzyl | 4-Me-benzyl |
| 1348 | Ph | 4-Me-benzyl | 2-Cl-4-MeO-benzyl |
| 1349 | Ph | 4-Me-benzyl | 2-MeO-benzyl |
| 1350 | Ph | 4-Me-benzyl | 4-MeO-benzyl |

TABLE 55

| No | R¹ | R² | R³ |
|---|---|---|---|
| 1351 | Ph | 4-Cl-benzyl | Me |
| 1352 | Ph | 4-Cl-benzyl | allyl |
| 1353 | Ph | 4-Cl-benzyl | benzyl |
| 1354 | Ph | 4-Cl-benzyl | 2-Cl-benzyl |
| 1355 | Ph | 4-Cl-benzyl | 4-Cl-benzyl |
| 1356 | Ph | 4-Cl-benzyl | 2-Me-benzyl |
| 1357 | Ph | 4-Cl-benzyl | 4-Me-benzyl |
| 1358 | Ph | 4-Cl-benzyl | 2-Cl-4-MeO-benzyl |
| 1359 | Ph | 4-Cl-benzyl | 2-MeO-benzyl |
| 1360 | Ph | 4-Cl-benzyl | 4-MeO-benzyl |
| 1361 | Ph | 4-MeO-benzyl | Me |
| 1362 | Ph | 4-MeO-benzyl | allyl |
| 1363 | Ph | 4-MeO-benzyl | benzyl |
| 1364 | Ph | 4-MeO-benzyl | 2-Cl-benzyl |
| 1365 | Ph | 4-MeO-benzyl | 4-Cl-benzyl |
| 1366 | Ph | 4-MeO-benzyl | 2-Me-benzyl |
| 1367 | Ph | 4-MeO-benzyl | 4-Me-benzyl |
| 1368 | Ph | 4-MeO-benzyl | 2-Cl-4-MeO-benzyl |
| 1369 | Ph | 4-MeO-benzyl | 2-MeO-benzyl |
| 1370 | Ph | 4-MeO-benzyl | 4-MeO-benzyl |
| 1371 | Ph | 2-pyridylCH$_2$ | Me |
| 1372 | Ph | 2-pyridylCH$_2$ | allyl |
| 1373 | Ph | 2-pyridylCH$_2$ | benzyl |
| 1374 | Ph | 2-pyridylCH$_2$ | 2-Cl-benzyl |
| 1375 | Ph | 2-pyridylCH$_2$ | 4-Cl-benzyl |

TABLE 56

| No | R¹ | R² | R³ |
|---|---|---|---|
| 1376 | Ph | 2-pyridylCH$_2$ | 2-Me-benzyl |
| 1377 | Ph | 2-pyridylCH$_2$ | 4-Me-benzyl |
| 1378 | Ph | 2-pyridylCH$_2$ | 2-Cl-4-MeO-benzyl |
| 1379 | Ph | 2-pyridylCH$_2$ | 2-MeO-benzyl |
| 1380 | Ph | 2-pyridylCH$_2$ | 4-MeO-benzyl |
| 1381 | Ph | 3-pyridylCH$_2$ | Me |
| 1382 | Ph | 3-pyridylCH$_2$ | allyl |
| 1383 | Ph | 3-pyridylCH$_2$ | benzyl |
| 1384 | Ph | 3-pyridylCH$_2$ | 2-Cl-benzyl |
| 1385 | Ph | 3-pyridylCH$_2$ | 4-Cl-benzyl |
| 1386 | Ph | 3-pyridylCH$_2$ | 2-Me-benzyl |
| 1387 | Ph | 3-pyridylCH$_2$ | 4-Me-benzyl |
| 1388 | Ph | 3-pyridylCH$_2$ | 2-Cl-4-MeO-benzyl |
| 1389 | Ph | 3-pyridylCH$_2$ | 2-MeO-benzyl |
| 1390 | Ph | 3-pyridylCH$_2$ | 4-MeO-benzyl |
| 1391 | Ph | 4-pyridylCH$_2$ | Me |
| 1392 | Ph | 4-pyridylCH$_2$ | allyl |
| 1393 | Ph | 4-pyridylCH$_2$ | benzyl |
| 1394 | Ph | 4-pyridylCH$_2$ | 2-Cl-benzyl |
| 1395 | Ph | 4-pyridylCH$_2$ | 4-Cl-benzyl |
| 1396 | Ph | 4-pyridylCH$_2$ | 2-Me-benzyl |
| 1397 | Ph | 4-pyridylCH$_2$ | 4-Me-benzyl |
| 1398 | Ph | 4-pyridylCH$_2$ | 2-Cl-4-MeO-benzyl |
| 1399 | Ph | 4-pyridylCH$_2$ | 2-MeO-benzyl |
| 1400 | Ph | 4-pyridylCH$_2$ | 4-MeO-benzyl |

TABLE 57

| No | R¹ | R² | R³ |
|---|---|---|---|
| 1401 | Pr' | benzyl | benzyl |
| 1402 | Pr' | benzyl | 4-Cl-benzyl |
| 1403 | Pr' | benzyl | 4-Me-benzyl |
| 1404 | Pr' | benzyl | 4-MeO-benzyl |

TABLE 57-continued

| No | R¹ | R² | R³ |
|---|---|---|---|
| 1405 | Pr' | 4-Cl-benzyl | benzyl |
| 1406 | Pr' | 4-Cl-benzyl | 4-Cl-benzyl |
| 1407 | Pr' | 4-Cl-benzyl | 4-Me-benzyl |
| 1408 | Pr' | 4-Cl-benzyl | 4-MeO-benzyl |
| 1409 | Pr' | 4-Me-benzyl | benzyl |
| 1410 | Pr' | 4-Me-benzyl | 4-Cl-benzyl |
| 1411 | Pr' | 4-Me-benzyl | 4-Me-benzyl |
| 1412 | Pr' | 4-Me-benzyl | 4-MeO-benzyl |
| 1413 | Pr' | 4-MeO-benzyl | benzyl |
| 1414 | Pr' | 4-MeO-benzyl | 4-Cl-benzyl |
| 1415 | Pr' | 4-MeO-benzyl | 4-Me-benzyl |
| 1416 | Pr' | 4-MeO-benzyl | 4-MeO-benzyl |
| 1417 | Pr' | 4-pyridylCH$_2$ | benzyl |
| 1418 | Pr' | 4-pyridylCH$_2$ | 4-Cl-benzyl |
| 1419 | Pr' | 4-pyridylCH$_2$ | 4-Me-benzyl |
| 1420 | Pr' | 4-pyridylCH$_2$ | 4-MeO-benzyl |
| 1421 | Me | benzyl | Ph |
| 1422 | Me | 4-Cl-benzyl | Ph |
| 1423 | Me | 4-Me-benzyl | Ph |
| 1424 | Me | 4-MeO-benzyl | Ph |
| 1425 | Me | 4-pyridylCH$_2$ | Ph |

TABLE 58

| No | R¹ | R² | R³ |
|---|---|---|---|
| 1426 | Me | benzyl | 3-Cl-Ph |
| 1427 | Me | 4-Cl-benzyl | 3-Cl-Ph |
| 1428 | Me | 4-Me-benzyl | 3-Cl-Ph |
| 1429 | Me | 4-MeO-benzyl | 3-Cl-Ph |
| 1430 | Me | 4-pyridylCH$_2$ | 3-Cl-Ph |
| 1431 | Me | benzyl | 4-Cl-Ph |
| 1432 | Me | 4-Cl-benzyl | 4-Cl-Ph |
| 1433 | Me | 4-Me-benzyl | 4-Cl-Ph |
| 1434 | Me | 4-MeO-benzyl | 4-Cl-Ph |
| 1435 | Me | 4-pyridylCH$_2$ | 4-Cl-Ph |
| 1436 | Me | benzyl | 3-Me-Ph |
| 1437 | Me | 4-Cl-benzyl | 3-Me-Ph |
| 1438 | Me | 4-Me-benzyl | 3-Me-Ph |
| 1439 | Me | 4-MeO-benzyl | 3-Me-Ph |
| 1440 | Me | 4-pyridylCH$_2$ | 3-Me-Ph |
| 1441 | Me | benzyl | 4-Me-Ph |
| 1442 | Me | 4-Cl-benzyl | 4-Me-Ph |
| 1443 | Me | 4-Me-benzyl | 4-Me-Ph |
| 1444 | Me | 4-MeO-benzyl | 4-Me-Ph |
| 1445 | Me | 4-pyridylCH$_2$ | 4-Me-Ph |
| 1446 | Me | benzyl | 3-MeO-Ph |
| 1447 | Me | 4-Cl-benzyl | 3-MeO-Ph |
| 1448 | Me | 4-Me-benzyl | 3-MeO-Ph |
| 1449 | Me | 4-MeO-benzyl | 3-MeO-Ph |
| 1450 | Me | 4-pyridylCH$_2$ | 3-MeO-Ph |

TABLE 59

| No | R¹ | R² | R³ |
|---|---|---|---|
| 1451 | Me | benzyl | 4-MeO-Ph |
| 1452 | Me | 4-Cl-benzyl | 4-MeO-Ph |
| 1453 | Me | 4-Me-benzyl | 4-MeO-Ph |
| 1454 | Me | 4-MeO-benzyl | 4-MeO-Ph |
| 1455 | Me | 4-pyridylCH$_2$ | 4-MeO-Ph |
| 1456 | Et | benzyl | Ph |
| 1457 | Et | 4-Cl-benzyl | Ph |
| 1458 | Et | 4-Me-benzyl | Ph |
| 1459 | Et | 4-MeO-benzyl | Ph |
| 1460 | Et | 4-pyridylCH$_2$ | Ph |
| 1461 | Et | benzyl | 3-Cl-Ph |
| 1462 | Et | 4-Cl-benzyl | 3-Cl-Ph |
| 1463 | Et | 4-Me-benzyl | 3-Cl-Ph |
| 1464 | Et | 4-MeO-benzyl | 3-Cl-Ph |
| 1465 | Et | 4-pyridylCH$_2$ | 3-Cl-Ph |
| 1466 | Et | benzyl | 4-Cl-Ph |
| 1467 | Et | 4-Cl-benzyl | 4-Cl-Ph |
| 1468 | Et | 4-Me-benzyl | 4-Cl-Ph |
| 1469 | Et | 4-MeO-benzyl | 4-Cl-Ph |
| 1470 | Et | 4-pyridylCH$_2$ | 4-Cl-Ph |
| 1471 | Et | benzyl | 3-Me-Ph |
| 1472 | Et | 4-Cl-benzyl | 3-Me-Ph |
| 1473 | Et | 4-Me-benzyl | 3-Me-Ph |
| 1474 | Et | 4-MeO-benzyl | 3-Me-Ph |
| 1475 | Et | 4-pyridylCH$_2$ | 3-Me-Ph |

TABLE 60

| No | R¹ | R² | R³ |
|---|---|---|---|
| 1476 | Et | benzyl | 4-Me-Ph |
| 1477 | Et | 4-Cl-benzyl | 4-Me-Ph |
| 1478 | Et | 4-Me-benzyl | 4-Me-Ph |
| 1479 | Et | 4-MeO-benzyl | 4-Me-Ph |
| 1480 | Et | 4-pyridylCH$_2$ | 4-Me-Ph |
| 1481 | Et | benzyl | 3-MeO-Ph |
| 1482 | Et | 4-Cl-benzyl | 3-MeO-Ph |
| 1483 | Et | 4-Me-benzyl | 3-MeO-Ph |
| 1484 | Et | 4-MeO-benzyl | 3-MeO-Ph |
| 1485 | Et | 4-pyridylCH$_2$ | 3-MeO-Ph |
| 1486 | Et | benzyl | 4-MeO-Ph |
| 1487 | Et | 4-Cl-benzyl | 4-MeO-Ph |
| 1488 | Et | 4-Me-benzyl | 4-MeO-Ph |
| 1489 | Et | 4-MeO-benzyl | 4-MeO-Ph |
| 1490 | Et | 4-pyridylCH$_2$ | 4-MeO-Ph |
| 1491 | Me | 4-H$_2$N-benzyl | benzyl |
| 1492 | Me | 4-H$_2$N-benzyl | 4-Cl-benzyl |
| 1493 | Me | 4-H$_2$N-benzyl | 4-HO-benzyl |
| 1494 | Me | 4-H$_2$N-benzyl | 4-MeO-benzyl |
| 1495 | Me | 4-H$_2$N-benzyl | α-Me-4-MeO-benzyl |
| 1496 | Me | 4-H$_2$N-benzyl | 4-EtO-benzyl |
| 1497 | Me | 4-H$_2$N-benzyl | 4-PrO-benzyl |
| 1498 | Me | 4-H$_2$N-benzyl | 4-AcO-benzyl |
| 1499 | Me | 4-H$_2$N-benzyl | 4-MOMO-benzyl |
| 1500 | Me | 4-H$_2$N-benzyl | 4-MeO-Ph(CH$_2$)$_2$ |

TABLE 61

| No | R¹ | R² | R³ |
|---|---|---|---|
| 1501 | Me | 4-AcNH-benzyl | benzyl |
| 1502 | Me | 4-AcNH-benzyl | 4-Cl-benzyl |
| 1503 | Me | 4-AcNH-benzyl | 4-HO-benzyl |
| 1504 | Me | 4-AcNH-benzyl | 4-MeO-benzyl |
| 1505 | Me | 4-AcNH-benzyl | α-Me-4-MeO-benzyl |
| 1506 | Me | 4-AcNH-benzyl | 4-EtO-benzyl |
| 1507 | Me | 4-AcNH-benzyl | 4-PrO-benzyl |
| 1508 | Me | 4-AcNH-benzyl | 4-AcO-benzyl |
| 1509 | Me | 4-AcNH-benzyl | 4-MOMO-benzyl |
| 1510 | Me | 4-AcNH-benzyl | 4-MeO-Ph(CH$_2$)$_2$ |
| 1511 | Me | 4-CF$_3$-benzyl | benzyl |
| 1512 | Me | 4-CF$_3$-benzyl | 4-Cl-benzyl |
| 1513 | Me | 4-CF$_3$-benzyl | 4-HO-benzyl |
| 1514 | Me | 4-CF$_3$-benzyl | 4-MeO-benzyl |
| 1515 | Me | 4-CF$_3$-benzyl | α-Me-4-MeO-benzyl |
| 1516 | Me | 4-CF$_3$-benzyl | 4-EtO-benzyl |
| 1517 | Me | 4-CF$_3$-benzyl | 4-PrO-benzyl |
| 1518 | Me | 4-CF$_3$-benzyl | 4-AcO-benzyl |
| 1519 | Me | 4-CF$_3$-benzyl | 4-MOMO-benzyl |
| 1520 | Me | 4-CF$_3$-benzyl | 4-MeO-Ph(CH$_2$)$_2$ |
| 1521 | Me | 2,5-(Me)$_2$-benzyl | benzyl |
| 1522 | Me | 2,5-(Me)$_2$-benzyl | 4-Cl-benzyl |
| 1523 | Me | 2,5-(Me)$_2$-benzyl | 4-HO-benzyl |
| 1524 | Me | 2,5-(Me)$_2$-benzyl | 4-MeO-benzyl |
| 1525 | Me | 2,5-(Me)$_2$-benzyl | α-Me-4-MeO-benzyl |

TABLE 62

| No | R¹ | R² | R³ |
|---|---|---|---|
| 1526 | Me | 2,5-(Me)₂-benzyl | 4-EtO-benzyl |
| 1527 | Me | 2,5-(Me)₂-benzyl | 4-PrO-benzyl |
| 1528 | Me | 2,5-(Me)₂-benzyl | 4-AcO-benzyl |
| 1529 | Me | 2,5-(Me)₂-benzyl | 4-MOMO-benzyl |
| 1530 | Me | 2,5-(Me)₂-benzyl | 4-MeO-Ph(CH₂)₂ |
| 1531 | Me | 1-naphthylmethyl | benzyl |
| 1532 | Me | 1-naphthylmethyl | 4-Cl-benzyl |
| 1533 | Me | 1-naphthylmethyl | 4-HO-benzyl |
| 1534 | Me | 1-naphthylmethyl | 4-MeO-benzyl |
| 1535 | Me | 1-naphthylmethyl | α-Me-4-MeO-benzyl |
| 1536 | Me | 1-naphthylmethyl | 4-EtO-benzyl |
| 1537 | Me | 1-naphthylmethyl | 4-PrO-benzyl |
| 1538 | Me | 1-naphthylmethyl | 4-AcO-benzyl |
| 1539 | Me | 1-naphthylmethyl | 4-MOMO-benzyl |
| 1540 | Me | 1-naphthylmethyl | 4-MeO-Ph(CH₂)₂ |
| 1541 | Me | 2-naphthylmethyl | benzyl |
| 1542 | Me | 2-naphthylmethyl | 4-Cl-benzyl |
| 1543 | Me | 2-naphthylmethyl | 4-HO-benzyl |
| 1544 | Me | 2-naphthylmethyl | 4-MeO-benzyl |
| 1545 | Me | 2-naphthylmethyl | α-Me-4-MeO-benzyl |
| 1546 | Me | 2-naphthylmethyl | 4-EtO-benzyl |
| 1547 | Me | 2-naphthylmethyl | 4-PrO-benzyl |
| 1548 | Me | 2-naphthylmethyl | 4-AcO-benzyl |
| 1549 | Me | 2-naphthylmethyl | 4-MOMO-benzyl |
| 1550 | Me | 2-naphthylmethyl | 4-MeO-Ph(CH₂)₂ |

TABLE 63

| No | R¹ | R² | R³ |
|---|---|---|---|
| 1551 | Me | 2-thenyl | benzyl |
| 1552 | Me | 2-thenyl | 4-Cl-benzyl |
| 1553 | Me | 2-thenyl | 4-HO-benzyl |
| 1554 | Me | 2-thenyl | 4-MeO-benzyl |
| 1555 | Me | 2-thenyl | α-Me-4-MeO-benzyl |
| 1556 | Me | 2-thenyl | 4-EtO-benzyl |
| 1557 | Me | 2-thenyl | 4-PrO-benzyl |
| 1558 | Me | 2-thenyl | 4-AcO-benzyl |
| 1559 | Me | 2-thenyl | 4-MOMO-benzyl |
| 1560 | Me | 2-thenyl | 4-MeO-Ph(CH₂)₂ |
| 1561 | Me | 3-thenyl | benzyl |
| 1562 | Me | 3-thenyl | 4-Cl-benzyl |
| 1563 | Me | 3-thenyl | 4-HO-benzyl |
| 1564 | Me | 3-thenyl | 4-MeO-benzyl |
| 1565 | Me | 3-thenyl | α-Me-4-MeO-benzyl |
| 1566 | Me | 3-thenyl | 4-EtO-benzyl |
| 1567 | Me | 3-thenyl | 4-PrO-benzyl |
| 1568 | Me | 3-thenyl | 4-AcO-benzyl |
| 1569 | Me | 3-thenyl | 4-MOMO-benzyl |
| 1570 | Me | 3-thenyl | 4-MeO-Ph(CH₂)₂ |
| 1571 | Me | benzyl | 4-HO-benzyl |
| 1572 | Me | benzyl | 4-EtO-benzyl |
| 1573 | Me | benzyl | 4-PrO-benzyl |
| 1574 | Me | benzyl | 4-AcO-benzyl |
| 1575 | Me | benzyl | 4-MOMO-benzyl |

TABLE 64

| No | R¹ | R² | R³ |
|---|---|---|---|
| 1576 | Me | benzyl | 4-MeO-Ph(CH₂)₂ |
| 1577 | Me | benzyl | 4-AllylO-benzyl |
| 1578 | Me | benzyl | 4-PhO-benzyl |
| 1579 | Me | 2-propynyl | 4-HO-benzyl |
| 1580 | Me | 2-propynyl | 4-EtO-benzyl |
| 1581 | Me | 2-propynyl | 4-PrO-benzyl |
| 1582 | Me | 2-propynyl | 4-AcO-benzyl |
| 1583 | Me | 2-propynyl | 4-MOMO-benzyl |
| 1584 | Me | 2-propynyl | 4-MeO-Ph(CH₂)₂ |
| 1585 | Me | 2-Cl-benzyl | 4-HO-benzyl |
| 1586 | Me | 2-Cl-benzyl | 4-EtO-benzyl |
| 1587 | Me | 2-Cl-benzyl | 4-PrO-benzyl |

TABLE 64-continued

| No | R¹ | R² | R³ |
|---|---|---|---|
| 1588 | Me | 2-Cl-benzyl | 4-AcO-benzyl |
| 1589 | Me | 2-Cl-benzyl | 4-MOMO-benzyl |
| 1590 | Me | 2-Cl-benzyl | 4-MeO-Ph(CH₂)₂ |
| 1591 | Me | 4-Cl-benzyl | 4-HO-benzyl |
| 1592 | Me | 4-Cl-benzyl | 4-EtO-benzyl |
| 1593 | Me | 4-Cl-benzyl | 4-PrO-benzyl |
| 1594 | Me | 4-Cl-benzyl | 4-AcO-benzyl |
| 1595 | Me | 4-Cl-benzyl | 4-MOMO-benzyl |
| 1597 | Me | 2-MeO-benzyl | 4-HO-benzyl |
| 1598 | Me | 2-MeO-benzyl | 4-EtO-benzyl |
| 1599 | Me | 2-MeO-benzyl | 4-PrO-benzyl |
| 1600 | Me | 2-MeO-benzyl | 4-AcO-benzyl |

TABLE 65

| No | R¹ | R² | R³ |
|---|---|---|---|
| 1601 | Me | 2-MeO-benzyl | 4-MOMO-benzyl |
| 1602 | Me | 2-MeO-benzyl | 4-MeO-Ph(CH₂)₂ |
| 1603 | Me | 4-MeO-benzyl | 4-HO-benzyl |
| 1604 | Me | 4-MeO-benzyl | 4-EtO-benzyl |
| 1605 | Me | 4-MeO-benzyl | 4-Pr-benzyl |
| 1606 | Me | 4-MeO-benzyl | 4-AcO-benzyl |
| 1607 | Me | 4-MeO-benzyl | 4-MOMO-benzyl |
| 1608 | Me | 4-MeO-benzyl | 4-MeO-Ph(CH₂)₂ |
| 1609 | Me | 2-pyridylCH₂ | 4-HO-benzyl |
| 1610 | Me | 2-pyridylCH₂ | 4-EtO-benzyl |
| 1611 | Me | 2-pyridylCH₂ | 4-PrO-benzyl |
| 1612 | Me | 2-pyridylCH₂ | 4-AcO-benzyl |
| 1613 | Me | 2-pyridylCH₂ | 4-MOMO-benzyl |
| 1614 | Me | 2-pyridylCH₂ | 4-MeO-Ph(CH₂)₂ |
| 1615 | Me | 4-pyridylCH₂ | 4-HO-benzyl |
| 1616 | Me | 4-pyridylCH₂ | 4-EtO-benzyl |
| 1617 | Me | 4-pyridylCH₂ | 4-PrO-benzyl |
| 1618 | Me | 4-pyridylCH₂ | 4-AcO-benzyl |
| 1619 | Me | 4-pyridylCH₂ | 4-MOMO-benzyl |
| 1620 | Me | 4-pyridylCH₂ | 4-MeO-Ph(CH₂)₂ |
| 1621 | Et | 4-H₂N-benzyl | benzyl |
| 1622 | Et | 4-H₂N-benzyl | 4-Cl-benzyl |
| 1623 | Et | 4-H₂N-benzyl | 4-HO-benzyl |
| 1624 | Et | 4-H₂N-benzyl | 4-MeO-benzyl |
| 1625 | Et | 4-H₂N-benzyl | α-Me-4-MeO-benzyl |

TABLE 66

| No | R¹ | R² | R³ |
|---|---|---|---|
| 1626 | Et | 4-H₂N-benzyl | 4-EtO-benzyl |
| 1627 | Et | 4-H₂N-benzyl | 4-PrO-benzyl |
| 1628 | Et | 4-H₂N-benzyl | 4-AcO-benzyl |
| 1629 | Et | 4-H₂N-benzyl | 4-MOMO-benzyl |
| 1630 | Et | 4-H₂N-benzyl | 4-MeO-Ph(CH₂)₂ |
| 1631 | Et | 4-AcNH-benzyl | benzyl |
| 1632 | Et | 4-ACNH-benzyl | 4-Cl-benzyl |
| 1633 | Et | 4-AcNH-benzyl | 4-HO-benzyl |
| 1634 | Et | 4-AcNH-benzyl | 4-MeO-benzyl |
| 1635 | Et | 4-AcNH-benzyl | α-Me-4-MeO-benzyl |
| 1636 | Et | 4-AcNH-benzyl | 4-EtO-benzyl |
| 1637 | Et | 4-AcNH-benzyl | 4-PrO-benzyl |
| 1638 | Et | 4-AcNH-benzyl | 4-AcO-benzyl |
| 1639 | Et | 4-AcNH-benzyl | 4-MOMO-benzyl |
| 1640 | Et | 4-AcNH-benzyl | 4-MeO-Ph(CH₂)₂ |
| 1641 | Et | 4-CF₃-benzyl | benzyl |
| 1642 | Et | 4-CF₃-benzyl | 4-Cl-benzyl |
| 1643 | Et | 4-CF₃-benzyl | 4-HO-benzyl |
| 1644 | Et | 4-CF₃-benzyl | 4-MeO-benzyl |
| 1645 | Et | 4-CF₃-benzyl | α-Me-4-MeO-benzyl |
| 1646 | Et | 4-CF₃-benzyl | 4-EtO-benzyl |
| 1647 | Et | 4-CF₃-benzyl | 4-PrO-benzyl |
| 1648 | Et | 4-CF₃-benzyl | 4-AcO-benzyl |

TABLE 66-continued

| No | R¹ | R² | R³ |
|---|---|---|---|
| 1649 | Et | 4-CF$_3$-benzyl | 4-MOMO-benzyl |
| 1650 | Et | 4-CF$_3$-benzyl | 4-MeO-Ph(CH$_2$)$_2$ |

TABLE 67

| No | R¹ | R² | R³ |
|---|---|---|---|
| 1651 | Et | 2,5-(Me)$_2$-benzyl | benzyl |
| 1652 | Et | 2,5-(Me)$_2$-benzyl | 4-Cl-benzyl |
| 1653 | Et | 2,5-(Me)$_2$-benzyl | 4-HO-benzyl |
| 1654 | Et | 2,5-(Me)$_2$-benzyl | 4-MeO-benzyl |
| 1655 | Et | 2,5-(Me)$_2$-benzyl | α-Me-4-MeO-benzyl |
| 1656 | Et | 2,5-(Me)$_2$-benzyl | 4-EtO-benzyl |
| 1657 | Et | 2,5-(Me)$_2$-benzyl | 4-PrO-benzyl |
| 1658 | Et | 2,5-(Me)$_2$-benzyl | 4-AcO-benzyl |
| 1659 | Et | 2,5-(Me)$_2$-benzyl | 4-MOMO-benzyl |
| 1660 | Et | 2,5-(Me)$_2$-benzyl | 4-MeO-Ph(CH$_2$)$_2$ |
| 1661 | Et | 1-naphthylmethyl | benzyl |
| 1662 | Et | 1-naphthylmethyl | 4-Cl-benzyl |
| 1663 | Et | 1-naphthylmethyl | 4-HO-benzyl |
| 1664 | Et | 1-naphthylmethyl | 4-MeO-benzyl |
| 1665 | Et | 1-naphthylmethyl | α-Me-4-MeO-benzyl |
| 1666 | Et | 1-naphthylmethyl | 4-EtO-benzyl |
| 1667 | Et | 1-naphthylmethyl | 4-PrO-benzyl |
| 1668 | Et | 1-naphthylmethyl | 4-AcO-benzyl |
| 1669 | Et | 1-naphthylmethyl | 4-MOMO-benzyl |
| 1670 | Et | 1-naphthylmethyl | 4-MeO-Ph(CH$_2$)$_2$ |
| 1671 | Et | 2-naphthylmethyl | benzyl |
| 1672 | Et | 2-naphthylmethyl | 4-Cl-benzyl |
| 1673 | Et | 2-naphthylmethyl | 4-HO-benzyl |
| 1674 | Et | 2-naphthylmethyl | 4-MeO-benzyl |
| 1675 | Et | 2-naphthylmethyl | α-Me-4-MeO-benzyl |

TABLE 68

| No | R¹ | R² | R³ |
|---|---|---|---|
| 1676 | Et | 2-naphthylmethyl | 4-EtO-benzyl |
| 1677 | Et | 2-naphthylmethyl | 4-PrO-benzyl |
| 1678 | Et | 2-naphthylmethyl | 4-AcO-benzyl |
| 1679 | Et | 2-naphthylmethyl | 4-MOMO-benzyl |
| 1680 | Et | 2-naphthylmethyl | 4-MeO-Ph(CH$_2$)$_2$ |
| 1681 | Et | 2-thenyl | benzyl |
| 1682 | Et | 2-thenyl | 4-Cl-benzyl |
| 1683 | Et | 2-thenyl | 4-HO-benzyl |
| 1684 | Et | 2-thenyl | 4-MeO-benzyl |
| 1685 | Et | 2-thenyl | α-Me-4-MeO-benzyl |
| 1686 | Et | 2-thenyl | 4-EtO-benzyl |
| 1687 | Et | 2-thenyl | 4-PrO-benzyl |
| 1688 | Et | 2-thenyl | 4-AcO-benzyl |
| 1689 | Et | 2-thenyl | 4-MOMO-benzyl |
| 1690 | Et | 2-thenyl | 4-MeO-Ph(CH$_2$)$_2$ |
| 1691 | Et | 3-thenyl | benzyl |
| 1692 | Et | 3-thenyl | 4-Cl-benzyl |
| 1693 | Et | 3-thenyl | 4-HO-benzyl |
| 1694 | Et | 3-thenyl | 4-MeO-benzyl |
| 1695 | Et | 3-thenyl | α-Me-4-MeO-benzyl |
| 1696 | Et | 3-thenyl | 4-EtO-benzyl |
| 1697 | Et | 3-thenyl | 4-PrO-benzyl |
| 1698 | Et | 3-thenyl | 4-AcO-benzyl |
| 1699 | Et | 3-thenyl | 4-MOMO-benzyl |
| 1700 | Et | 3-thenyl | 4-MeO-Ph(CH$_2$)$_2$ |

TABLE 69

| No | R¹ | R² | R³ |
|---|---|---|---|
| 1701 | Et | benzyl | 4-HO-benzyl |
| 1702 | Et | benzyl | 4-EtO-benzyl |
| 1703 | Et | benzyl | 4-PrO-benzyl |
| 1704 | Et | benzyl | 4-AcO-benzyl |
| 1705 | Et | benzyl | 4-MOMO-benzyl |
| 1706 | Et | benzyl | 4-MeO-Ph(CH$_2$)$_2$ |
| 1707 | Et | benzyl | 4-AllylO-benzyl |
| 1708 | Et | benzyl | 4-PhO-benzyl |
| 1709 | Et | 2-propynyl | 4-HO-benzyl |
| 1710 | Et | 2-propynyl | 4-EtO-benzyl |
| 1711 | Et | 2-propynyl | 4-PrO-benzyl |
| 1712 | Et | 2-propynyl | 4-AcO-benzyl |
| 1713 | Et | 2-propynyl | 4-MOMO-benzyl |
| 1714 | Et | 2-propynyl | 4-MeO-Ph(CH$_2$)$_2$ |
| 1715 | Et | 2-Cl-benzyl | 4-HO-benzyl |
| 1716 | Et | 2-Cl-benzyl | 4-EtO-benzyl |
| 1717 | Et | 2-Cl-benzyl | 4-PrO-benzyl |
| 1718 | Et | 2-Cl-benzyl | 4-AcO-benzyl |
| 1719 | Et | 2-Cl-benzyl | 4-MOMO-benzyl |
| 1720 | Et | 2-Cl-benzyl | 4-MeO-Ph(CH$_2$)$_2$ |
| 1721 | Et | 4-Cl-benzyl | 4-HO-benzyl |
| 1722 | Et | 4-Cl-benzyl | 4-EtO-benzyl |
| 1723 | Et | 4-Cl-benzyl | 4-PrO-benzyl |
| 1724 | Et | 4-Cl-benzyl | 4-AcO-benzyl |
| 1725 | Et | 4-Cl-benzyl | 4-MOMO-benzyl |

TABLE 70

| No | R¹ | R² | R³ |
|---|---|---|---|
| 1726 | Et | 4-Cl-benzyl | 4-MeO-Ph(CH$_2$)$_2$ |
| 1727 | Et | 2-MeO-benzyl | 4-HO-benzyl |
| 1728 | Et | 2-MeO-benzyl | 4-EtO-benzyl |
| 1729 | Et | 2-MeO-benzyl | 4-PrO-benzyl |
| 1730 | Et | 2-MeO-benzyl | 4-AcO-benzyl |
| 1731 | Et | 2-MeO-benzyl | 4-MOMO-benzyl |
| 1732 | Et | 2-MeO-benzyl | 4-MeO-Ph(CH$_2$)$_2$ |
| 1733 | Et | 4-MeO-benzyl | 4-HO-benzyl |
| 1734 | Et | 4-MeO-benzyl | 4-EtO-benzyl |
| 1735 | Et | 4-MeO-benzyl | 4-PrO-benzyl |
| 1736 | Et | 4-MeO-benzyl | 4-AcO-benzyl |
| 1737 | Et | 4-MeO-benzyl | 4-MOMO-benzyl |
| 1738 | Et | 4-MeO-benzyl | 4-MeO-Ph(CH$_2$)$_2$ |
| 1739 | Et | 2-pyridylCH$_2$ | 4-HO-benzyl |
| 1740 | Et | 2-pyridylCH$_2$ | 4-EtO-benzyl |
| 1741 | Et | 2-pyridylCH$_2$ | 4-PrO-benzyl |
| 1742 | Et | 2-pyridylCH$_2$ | 4-AcO-benzyl |
| 1743 | Et | 2-pyridylCH$_2$ | 4-MOMO-benzyl |
| 1744 | Et | 2-pyridylCH$_2$ | 4-MeO-Ph(CH$_2$)$_2$ |
| 1745 | Et | 4-pyridylCH$_2$ | 4-HO-benzyl |
| 1746 | Et | 4-pyridylCH$_2$ | 4-EtO-benzyl |
| 1747 | Et | 4-pyridylCH$_2$ | 4-PrO-benzyl |
| 1748 | Et | 4-pyridylCH$_2$ | 4-AcO-benzyl |
| 1749 | Et | 4-pyridylCH$_2$ | 4-MOMO-benzyl |
| 1750 | Et | 4-pyridylCH$_2$ | 4-MeO-Ph(CH$_2$)$_2$ |

TABLE 71

| No | Physical Data |
|---|---|
| A-176 | mp 89–97° C. |
| A-1301 | mp 83–92° C. |
| A-1310 | Isomer A: mp 84–86° C. |
| | Isomer B: mp 173–174° C. |
| B-476 | mp 112–114° C. |
| B-480 | mp 78–89° C. |
| B-1301 | ¹H-NMR(CDCl$_3$) δ ppm: 2.97(3H, d, J=4.9), 3.91(3H, s), 3.94 (3H, s), 5.90(1H, br), 7.40(5H, m) |
| B-1310 | mp 136–137° C. |
| B-1331 | ¹H-NMR(CDCl$_3$) δ ppm: 2.89(3H, d, J=4.9), 3.91(3H, s), 5.25 (1H, s), 6.58(1H, br), 7.25–7.40(8H, m), 7.51–7.55(2H, m) |
| C-1 | ¹H-NMR(CDCl$_3$) δ ppm: 2.04(3H, s), 2.85(3H, s), 3.03(3H, s), 3.93(3H, s), 3.97(3H, s) |
| C-10 | ¹H-NMR(CDCl$_3$) δ ppm: 2.02(3H, s), 2.74(3H, s), 3.00(3H, s), 3.92(3H, s), 5.19(2H, s), 7.33(5H, m) |

TABLE 71-continued

| No | Physical Data |
|---|---|
| C-11 | $^1$H-NMR(CDCl$_3$) δ ppm: 2.01(3H, s), 2.80(3H, s), 3.03(3H, s), 3.93(3H, s), 5.30(1H, d, J=13.4), 5.33(1H, d, J=13.4), 7.20–7.43(4H, m) |
| C-12 | $^1$H-NMR(CDCl$_3$) δ ppm: 2.04(3H, s), 2.77(3H, s), 3.03(3H, s), 3.92(3H, s), 5.12(2H, s), 5.16(2H, s), 7.20–7.32(4H, m) |
| C-13 | mp 83-85° C. |
| C-19 | $^1$H-NMR(CDCl$_3$) δ ppm: 2.02(3H, s), 2.71(3H, s), 2.99(3H, s), 3.80(3H, s), 3.91(3H, s), 5.11(2H, s), 6.86(2H, d, J=8.5), 7.27(2H, d, J=8.5) |
| C-20 | $^1$H-NMR(CDCl$_3$) δ ppm: 1.99(3H, s), 2.75(3H, s), 2.99(3H, s), 3.92(3H, s), 5.30(2H, s), 6.86–7.47(9H, m) |
| C-21 | $^1$H-NMR(CDCl$_3$) δ ppm: 2.00(3H, s), 2.79(3H, s), 3.03(3H, s), 3.93(3H, s), 5.12(2H, s), 7.18(1H, dd, J=8.5, 1.8), 7.43(2H, m) |
| C-86 | $^1$H-NMR(CDCl$_3$) δ ppm: 2.04(3H, s), 2.78(3H, s), 3.01(3H, s), 4.62(2H, d, J=5.5), 5.15–5.38(4H, m), 5.87–6.02(1H, m), 7.20–7.47(4H, m) |

TABLE 72

| No | Physical Data |
|---|---|
| C-87 | $^1$H-NMR(CDCl$_3$) δ ppm: 2.04(3H, s), 2.76(3H, s), 3.01(3H, s), 4.61(2H, d, J=5.5), 5.16(2H, s), 5.16–5.29(2H, m), 5.87–6.02(1H, m), 7.20–7.32(4H, m) |
| C-94 | $^1$H-NMR(CDCl$_3$) δ ppm: 2.05(3H, s), 2.70(3H, s), 2.98(3H, s), 3.80(3H, s), 4.61(2H, d, J=5.5), 5.12(2H, s), 5.16–5.28(2H, m), 5.87–6.01(1 H, m), 6.86(2H, d, J=8.5), 7.28(2H, d, J=8.5) |
| C-95 | $^1$H-NMR(CDCl$_3$) δ ppm: 2.02(3H, s), 2.73(3H, s), 2.98(3H, s), 4.61(2H, d, J=5.5), 5.16–5.29(2H, m), 5.30(2H, s), 5.87–6.02(1H, m), 6.87–7.47(9H, m) |
| C-96 | $^1$H-NMR(CDCl$_3$) δ ppm: 2.03(3H, s), 2.77(3H, s), 3.01(3H, s), 4.62(2H, d, J=5.5), 5.12(2H, s), 5.12–5.29(2H, m), 5.87–6.02(1H, m), 7.18(1H, dd, J=8.5, 1.8), 7.26–7.43(2H, m) |
| C-101 | $^1$H-NMR(CDCl$_3$) δ ppm 2.09(3H, s), 2.79(3H, s), 2.98(3H, s), 3.97(3H, s), 4.74–4.84(2H, m), 6.27–6.37(1H, m), 6.57–6.63(1H, m), 7.21–7.46(5H, m) |
| C-144 | mp 96–99° C. |
| C-146 | mp 82–83.5° C. |
| C-176 | $^1$H-NMR(CDCl$_3$) δ ppm: 2.06(3H, s), 2.63(3H, s), 2.98(3H, s), 3.95(3H, s), 5.12(1H, d, J=12.2), 5.15(1H, d, J=12.2), 7.32(5H, m) |
| C-180 | $^1$H-NMR(CDCl$_3$) δ ppm: 2.06(3H, s), 2.64(3H, s), 2.99(3H, s), 4.64(2H, d, J=5.9), 5.13–5.32(4H, m), 5.88–6.03(1H, m), 7.37(5H, m) |
| C-185 | mp 102–104° C. |
| C-194 | $^1$H-NMR(CDCl$_3$) δ ppm: 2.04(3H, s), 2.50(3H, s), 2.95(3H, s), 3.80(3H, s), 5.09 and 5.15(each 1H, ABq, J=12.2), 5.10(2H, s), 6.84(2H, d, J=8.7), 7.26(2H, d, J=8.8), 7.31(5H, m) |
| C-219 | mp 93–93.5° C. |
| C-251 | mp 82.5–83.5° C. |
| C-276 | mp 49.5–51° C. |
| C-301 | mp 92–93° C. |
| C-326 | mp 54.5–56° C. |
| C-376 | mp 68–69° C. |

TABLE 73

| No | Physical Data |
|---|---|
| C-451 | mp 93–94° C. |
| C-476 | mp 77–79° C. |
| C-480 | $^1$H-NMR(CDCl$_3$) δ ppm: 2.06(3H, s), 2.70(3H, s), 3.01(3H, s), 4.65(2H, m), 5.07(2H, s), 5.19–5.32(2H, m), 5.88–6.03(1H, m), 7.16(1H, dd, J=8.5, 1.8), 7.40–7.44(2H, m) |
| C-619 | $^1$H-NMR(CDCl$_3$) δ ppm: 1.05(3H, t, J=7.3), 2.50–2.63(2H, m), 2.68(3H, s), 2.98(3H, s), 3.80(3H, s), 3.89(3H, s), 5.11(2H, s), 6.86(2H, d, J=9.2), 7.28(2H, d, J=9.2) |
| C-780 | $^1$H-NMR(CDCl$_3$) δ ppm: 1.08(3H, t, J=7.3), 2.53–2.66(2H, m), 2.60(3H, s), 2.97(3H, s), 4.64(2H, d, J=6.1), 5.12(1H, d, J=11.6), 5.14(1H, d, J=11.6), 5.18–5.31(2H, m), 5.88–6.02(1H, m), 7.33(5H, m) |
| C-1310 | mp 111–113° C. |

TABLE 73-continued

| No | Physical Data |
|---|---|
| C-1331 | mp 78–96° C. |
| F-176 | $^1$H-NMR(CDCl$_3$) δ ppm: 2.08(3H, s), 3.23(3H, s), 3.44(3H, s), 3.97(3H, s), 5.16(2H, s), 7.26–7.34(5H, m) |
| F-180 | $^1$H-NMR(CDCl$_3$) δ ppm: 2.07(3H, s), 3.23(3H, s), 3.45(3H, s), 4.66(2H, d, J=5.5), 5.16(2H, s), 5.16–5.33(2H, m), 5.92–6.02(1H, m), 7.26–7.32(5H, m) |
| G-194 | $^1$H-NMR(CDCl$_3$) δ ppm: 1.59–1.82(4H, m), 2.03(3H, m), 2.84(2H, m), 3.49(2H, m), 3.79(3H, s), 5.10–5.13(4H, m), 6.84(2H, d, J=8.8), 7.25(2H, d, J=8.8), 7.30(5H, m) |
| H-176 | mp 121–123° C. |
| H-194 | $^1$H-NMR(CDCl$_3$) δ ppm: 1.10–1.28(2H, m), 1.47(4H, m), 2.05(3H, s), 2.80–2.96(2H, m), 3.45(1H, m), 3.64(1H, m), 3.80(3H, s), 5.09(2H, s), 5.10 and 5.16(each 1H, ABq, J=12.2), 6.84(2H, d, J=8.5), 7.25(2H, d, J=8.5), 7.31(5H, m) |
| L-794 | $^1$H-NMR(CDCl$_3$) δ ppm: 0.46–1.01(2H, m), 1.08 and 1.12(total 3H, t, J=7.6), 1.36–1.90(2H, m), 1.92 and 1.95(total 3H, s), 2.51–2.81(4H, m), 3.07(1H, m), 3.75(1H, m), 3.80(3H, s), 4.46(1H, m), 4.79 and 4.92(total 1H, br d), 5.05–5.25(4H, m), 6.83–6.89(2H, m), 7.27–7.36(7H, m) |

TABLE 74

| No | Physical Data |
|---|---|
| M-1194 | $^1$H-NMR(CDCl$_3$) δ ppm: 023–1.10(2H, m), 1.11 and 1.12(total 3H, t, J=7.6), 1.41–1.83(2H, m), 1.92 and 2.03(total 3H, s), 2.57–2.74(4H, m), 2.95 and 3.19(total 1H, m), 3.76(1H, m), 3.80 and 3.81(total 3H, s), 4.40(1H, m), 5.04–5.18(4H, m), 6.83–6.90(2H, m), 7.17–7.32(4H, m), 7.56–7.58(2H, m) |
| N-794 | mp 136–137° C. |
| O-794 | $^1$H-NMR(CDCl$_3$) δ ppm: 0.51 and 0.96(total 1H, m), 1.08 and 1.11(total 3H, t, J=7.6), 1.37–1.56(1H, m), 1.81(1H, m), 2.50–2.78(4H, m), 3.03(1H, m), 3.66 and 3.67(total 3H, s), 3.79 and 3.80(total 3H, s), 4.10–4.22(2H, m), 5.05–5.21(4H, m), 6.85(2H, br d, J=8.8), 7.24–7.34(7H, m) |
| P-794 | $^1$H-NMR(CDCl$_3$) δ ppm: 0.47–1.20(2H, m), 1.09 and 1.12(total 3H, t, J=7.6), 1.42–1.58(1H, m), 1.83(1H, m), 2.51–2.78(4H, m), 2.90 and 2.92(total 3H, s), 3.03–3.36(2H, m), 3.62–3.79(1H, m), 3.80 and 3.81(total 3H, s), 4.40(1H, m), 5.05–5.22(4H, m), 6.85 and 6.86(total 2H, d, J =8.5), 7.23–7.36(7H, m) |
| R-194 | $^1$H-NMR(CDCl$_3$) δ ppm: 1.25–1.81(4H, m), 2.05 and 2.06(total 3H, s), 2.64–2.89(1H, m), 3.30 and 3.31(total 3H, s), 3.79 and 3.80(total 3H, s), 3.10–3.95(4H, m), 5.05–5.18(4H, m), 6.85(2H, br d, J =8.5), 7.24–7.33(7H, m) |
| T-794 | $^1$H-NMR(CDCl$_3$) δ ppm: 1.08(3H, t, J=7.3), 1.75–2.76(4H, m), 2.62(2H, q, J=7.3), 2.91–3.01(2H, m), 3.44–3.55(1H, m), 3.79(3H, s), 3.80–3.96(1H, m), 5.05(1H, d, J=12.2), 5.10(2H, s), 5.16(1H, d, J=12.2), 6.85(2H, dd, J=1.2, 8.6), 7.12(1H, br), 7.28(7H, m) |
| U-794 | $^1$H-NMR(CDCl$_3$) δ ppm: 1.08(3H, t, J=7.3), 1.78–2.68(4H, m), 2.61(2H, q, J=7.3), 2.89–3.01(2H, m), 3.43–3.53(1H, m), 3.79(3H, s), 3.82 and 3.83(total 3H, s), 3.80–3.95(1 H, m), 5.05(1H, d, J=12.2), 5.09(2H, s), 5.15(1H, d, J=12.2), 6.84(2H, d, J=8.9), 7.27(7H, m) |
| V-794 | mp 92–93° C. |
| W-10 | $^1$H-NMR(CDCl$_3$) δ ppm: 2.02(3H, s), 3.10–3.14(2H, m), 3.43–3.58(2H, m), 3.62–3.75(4H, m), 3.93(3H, s), 5.20(2H, s), 7.34(5H, m) |

TABLE 75

| No | Physical Data |
|---|---|
| W-144 | $^1$H-NMR(CDCl$_3$) δ ppm: 2.07(3H, s), 2.44(1H, t, J=2.5), 3.10(2H, m), 3.46(1H, m), 3.57–3.78(5H, m), 3.81(3H, s), 4.72(2H, d, J 2.5), 5.13(2H, s), 6.86(2H, d, J=8.7), 7.27(2H, d, J= 8.7) |
| W-176 | mp 111–113° C. |
| W-194 | $^1$H-NMR(CDCl$_3$) δ ppm: 2.06(3H, s), 2.84(1H, ddd, J=3.2, 6.4, 13.4), 2.93(1H, ddd, J=3.2, 6.6, 13.4), 3.17(1H, ddd, J=3.2, 6.6, 11.5), 3.29(1H, ddd, 3.2, 6.4, 11.5), 3.57–3.62(4H, m), 3.80(3H, s), 5.10(2H, s), 5.11 and 5.17(each 1H, ABq, J=12.2), 6.85 |

TABLE 75-continued

| No | Physical Data |
|---|---|
| | (2H, d, J=8.5), 7.25(2H, d, J=8.5), 7.31(5H, m) |
| W-199 | $^1$H-NMR(CDCl$_3$) δ ppm: 2.01(3H, s), 2.91(1H, m), 3.13(1H, m), 3.29(1H, m), 3.52–3.72(5H, m), 3.88(3H, s), 5.13 and 5.22 (each 1H, ABq, J=12.2), 6.99(2H, d, J=9.0), 7.27–7.35(5H, m), 7.89(2H, d, J=9.0)) |
| W-319 | $^1$H-NMR(CDCl$_3$) δ ppm: 2.06(3H, s), 2.85–3.03(2H, m), 3.21–3.38(2H, m), 3.58–3.63(4H, m), 3.80(3H, s), 5.06 and 5.13 (each 1H, ABq, J=12.5), 5.11(2H, s), 6.86(2H, d, J=8.8), 7.22–7.33(6H, m) |
| W-469 | $^1$H-NMR(CDCl$_3$) δ ppm: 2.03(3H, s), 2.86–3.01(2H, m), 3.23–3.35(2H, m), 3.59–3.65(4H, m), 3.78(6H, s), 5.03 and 5.11 (each 1H, ABq, J=12.0), 5.09(2H, s), 6.85(2H, d, J=8.8), 6.86 (2H, d, J=8.8), 7.25(2H, d, J=8.8), 7.26(2H, d, J=8.8) |
| W-569 | $^1$H-NMR(CDCl$_3$) δ ppm: 2.13(3H, s), 2.86–3.04(2H, m), 3.19–3.37(2H, m), 3.52–3.63(4H, m), 3.80(3H, s), 5.12(2H, s), 5.12 and 5.29(each 1H, ABq, J=12.0), 6.86(2H, d, J=8.8), 7.18–7.31(2H, m), 7.26(2H, d, J=8.8), 7.67(1H, dt, J=1.7, 7.6), 8.57(2H, br d, J=4.2) |
| W-594 | $^1$H-NMR(CDCl$_3$) δ ppm: 2.06(3H, s), 2.91–2.99(2H, m), 3.10–3.17(2H, m), 3.58–3.67(4H, m), 3.80(3H, s), 5.11(2H, s), 5.13 and 5.18(each 1H, ABq, J=12.5), 6.86(2H, d, J=8.5), 7.25 (2H, d, J=8.5), 7.26(1H, m), 7.63(1H, br d, J=7.8), 8.55–8.58 (2H, m) |
| W-785 | $^1$H-NMR(CDCl$_3$) δ ppm: 1.06(3H, t, J=7.2), 2.60(2H, q, J=7.2), 2.75–2.96(2H, m), 3.12–3.31(2H, m), 3.54–3.64(4H, m), 5.10 (1H, d, J=12.2), 5.18(1H, d, J=12.2), 7.32(10H, m) |

TABLE 76

| No | Physical Data |
|---|---|
| W-788 | $^1$H-NMR(CDCl$_3$) δ ppm: 1.05(3H, t, J=7.3), 2.58(2H, q, J=7.3), 2.77–2.98(2H, m), 3.13–3.35(2H, m), 3.51–3.65(4H, m), 5.09 (1H, d, J=12.2), 5.13(2H, s), 5.19(1H, d, J=12.2), 7.24–7.38 (9H, m) |
| W-794 | $^1$H-NMR(CDCl$_3$) δ ppm: 1.07(3H, t, J=7.6), 2.60(2H, q, J=7.6), 2.76(1H, ddd, J=3.2, 6.3, 13.5), 2.89(1H, ddd, J=3.2, 6.3, 13.5), 3.15(1H, m, J=3.2, 6.3, 11.5), (1H, ddd, J=3.2, 6.3, 11.5), 3.54–3.62(4H, m), 3.79(3H, s), 5.09 and 5.17(each 1H, ABq, J=12.2), 5.10(2H, s), 6.84(2H, d, J=8.3), 7.24–7.35(7H, m) |
| W-869 | $^1$H-NMR(CDCl$_3$) δ ppm: 1.09(3H, t, J=7.3), 2.63(2H, q, J=7.3), 2.79–2.95(2H, m), 3.20–3.30(2H, m), 3.54–3.70(4H, m), 3.80 (3H, s), 5.11(2H, s), 5.25(2H, s), 6.86(2H, d, J=8.6), 7.22–7.38 (6H, m) |
| W-919 | $^1$H-NMR(CDCl$_3$) δ ppm: 1.06(3H, t, J=7.3), 2.59(2H, q, J=7.3), 2.84–2.93(2H, m), 3.20–3.34(2H, m), 3.53–3.67(4H, m), 3.80 (3H, s), 5.05(1H, d, J=12.2), 5.11(2H, s), 5.13(1H, d, J=12.2), 6.85(2H, d, J=8.6), 7.21–7.33(6H, m) |
| W-944 | $^1$H-NMR(CDCl$_3$) δ ppm: 1.06(3H, t, J=7.3), 2.34(3H, s), 2.59 (2H, q, J=7.3), 2.75–2.93(2H, m), 3.19–3.31(2H, m), 3.54–3.71(4H, m), 3.79(3H, s), 5.10(2H, s), 5.11(1H, d, J=12.2), 5.19(IH, d, J=12.2), 6.85(2H, d, J=8.6), 7.14–7.28(6H, m) |
| W-994 | $^1$H-NMR(CDCl$_3$) δ ppm: 1.05(3H, t, J=7.3), 2.33(3H, s), 2.58 (2H, q, J=7.3), 2.76–2.95(2H, m), 3.15–3.33(2H, m), 3.52–3.77(4H, m), 3.79(3H, s), 5.04(1H, d, J=12.2), 5.10(2H, s), 5.13(1H, d, J=12.2), 6.85(2H, d, J=8.6), 7.13(2H, d, J=7.9), 7.20(2H, d, J=7.9), 7.26(2H, d, J=8.6) |
| W-1019 | $^1$H-NMR(CDCl$_3$) δ ppm: 1.07(3H, t, J=7.3), 2.60(2H, q, J=7.3), 2.81–2.98(2H, m), 3.22–3.34(2H, m), 3.52–3.65(4H, m), 3.80 (3H, s), 3.81(3H, s), 5.11(2H, s), 5.17(1H, d, J=12.2), 5.23(1H, d, J=12.2), 6.82–6.95(4H, m), 7.23–7.30(4H, m) |
| W-1069 | $^1$H-NMR(CDCl$_3$) δ ppm: 1.04(3H, t, J=7.3), 2.57(2H, q, J=7.3), 2.83–2.91(2H, m), 3.24–3.31(2H, m), 3.56–3.68(4H, m), 3.80 (3H, s), 5.02(1H, d, J=12.2), 5.10(2H, s), 5.10(1H, d, J=12.2), 6.83–6.88(4H, m), 7.22–7.28(4H, m) |

TABLE 77

| No | Physical Data |
|---|---|
| W-1094 | $^1$H-NMR(CDCl$_3$) δ ppm: 1.07(3H, t, J=7.3), 2.60(2H, q, J=7.3), 2.86–2.94(2H, m), 3.24–3.33(2H, m), 3.52–3.69(4H, m), 3.79 |

TABLE 77-continued

| No | Physical Data |
|---|---|
| | (3H, s), 5.03(1H, d, J=12.8), 5.07(2H, s), 5.10(1H, d, J=12.8), 6.86(2H, d, J=8.6), 7.14(2H, d, J=8.6), 7.26(2H, d, J=8.6), 7.41 (2H, d, J=8.6) |
| W-1144 | $^1$H-NMR(CDCl$_3$) δ ppm: 1.12(3H, t, J=7.6), 2.66(2H, q, J=7.6), 2.91(2H, m), 3.28(2H, m), 3.57(4H, m), 3.80(3H, s), 5.12(2H, s), 5.26 and 5.28(each 1H, ABq, J=13.7), 6.86(2H, d, J=8.8), 7.18–7.30(4H, m), 7.67(1H, dt, J=1.7, 7.6), 8.56(1H, d, J=4.2) |
| W-1169 | $^1$H-NMR(CDCl$_3$) δ ppm: 1.06(3H, t, J=7.6), 2.59(2H, q, J=7.6), 2.83(2H, m), 3.24(2H, m), 3.51–3.70(4H, m), 3.80(3H, s), 5.11(2H, s), 5.12 and 5.17(each ABq, J=12.2), 6.85(2H, d, J=8.8), 7.24–7.30(3H, m), 7.63(1H, br d, J=7.8), 8.54–8.57 (1H, m) |
| W-1194 | mp 69.5–70.5° C. |
| W-1240 | $^1$H-NMR(CDCl$_3$) δ ppm: 0.92(3H, t, J=7.6), 1.53(2H, m), 2.57 (2H, t, J=8.1), 2.78(1H, m), 2.86(1H, m), 3.15(1H, m), 3.26 (1H, m), 3.57(4H, m), 3.80(3H, s), 5.08 and 5.16(each 1H, ABq, J=12.4), 5.09(2H, s), 6.84(2H, d, J=8.8), 7.24–7.34(7H, m) |
| W-1300 | mp 73–74° C. |
| W-1404 | Isomer A: $^1$H-NMR(CDCl$_3$) δ ppm: 1.20(6H, d, J=6.8), 2.70–2.90(3H, br), 3.00(1H, sept, J=6.8), 3.22(2H, m), 3.33(2H, m), 3.61(1H, br), 3.80(3H, s), 5.02(2H, br s), 5.07(2H, s), 6.85 (2H, d, J=8.6), 7.24(2H, d, J=8.6), 7.29–7.37(5H, m)<br>Isomer B: $^1$H-NMR(CDCl$_3$) δ ppm: 1.22(6H, d, J=7.1), 2.69–2.90(2H, m), 3.13–3.27(2H, m), 3.40(1H, sept, J=7.1), 3.50–3.68(4H, m), 3.80(3H, s), 5.06 and 5.15(each 1H, ABq, J=12.2), 5.09(2H, s), 6.85(2H, d, J=8.8), 7.26(2H, d, J=8.8), 7.28–7.36(5H, m) |
| W-1494 | $^1$H-NMR(CDCl$_3$) δ ppm: 2.02(3H, s), 2.92–2.97(2H, m), 3.31–3.35(2H, m), 3.62–3.68(6H, m), 3.80(3H, s), 4.97(1H, d, J=11.6), 5.05(1H, d, J=11.6), 5.10(2H, s), 6.63(2H, d, J=8.6), 6.85(2H, d, J=8.6), 7.12(2H, d, J=8.6), 7.26(2H, d, J=8.6) |

TABLE 78

| No | Physical Data |
|---|---|
| W-1504 | $^1$H-NMR(CDCl$_3$) δ ppm: 2.04(3H, s), 2.16(3H, s), 2.78–2.95 (2H, m), 3.21–3.34(2H, m), 3.57–3.66(4H, m), 3.80(3H, s), 5.05(1H, d, J=12.2), 5.13(1H, d, J=12.2), 5.10(2H, s), 6.85(2H, d, J=8.6), 7.19(1H, s), 7.23–7.28(4H, m) 7.46(2H, d, J=7.9) |
| W-1534 | $^1$H-NMR(CDCl$_3$) δ ppm: 2.03(3H, s), 2.68-2.90(2H, m), 3.07–3.25(2H, m), 3.56-3.63(4H, m), 3.79(3H, s), 5.09(2H, s), 5.50 (1H, d, J=12.2), 5.70(1H, d, J=12.2), 6.84(2H, d, J=8.5), 7.23(2H, d, J=8.5), 7.40–7.56(4H, m), 7.77–7.88(2H, m), 8.09(1H, m) |
| W-1554 | $^1$H-NMR(CDCl$_3$) δ ppm: 2.04(3H, s), 2.98–3.02(2H, m), 3.31–3.40(2H, m), 3.57–3.78(4H, m), 3.80(3H, s), 5.12(2H, s), 5.17 (2H, s), 6.77(1H, d, J=3.7), 6.84–6.98(3H, m), 7.24–7.29(3H, m) |
| W-1564 | $^1$H-NMR(CDCl$_3$) δ ppm: 2.05(3H, s), 2.90–3.05(2H, m), 3.25–3.42(2H, m), 3.55–3.75(4H, m), 3.80(3H, s), 5.11(2H, s), 5.14 (2H, s), 6.86(2H, d, J=8.8), 7.05(1H, dd, J=1.2 J=4.9), 7.22–7.30(4H, m) |
| W-1571 | $^1$H-NMR(CDCl$_3$) δ ppm: 2.06(3H, s), 2.83–3.92(2H, m), 3.15–3.36(2H, m), 3.55-3.62(4H, m), 5.07(2H, s), 5.10 and 5.17 (each 1H, ABq, J=12.5), 6.74(2H, d, J=8.5), 7.12(2H, d, J=8.5), 7.29–7.33(5H, m) |
| W-1575 | $^1$H-NMR(CDCl$_3$) δ ppm: 2.06(3H, s), 2.80–2.99(2H, m), 3.13–3.31(2H, m), 3.47(3H, s), 3.56–3.63(4H, m), 5.11(2H, s), 5.16 (2H, s), 5.11 and 5.17(each 1H, ABq, J=12.2), 6.98(2H, d, J=8.5), 7.25(2H, d, J=8.5), 7.26–7.33(5H, m) |
| W-1576 | $^1$H-NMR(CDCl$_3$) δ ppm: 2.07(3H, s), 2.85–2.96(4H, m), 3.13–3.30(2H, m), 3.52–3.70(4H, m), 3.77(3H, s), 4.30–4.36(2H, m), 5.11 and 5.20(each 1H, ABq, J=12.2), 6.82(2H, d, J=8.5), 7.11(2H, d, J=8.5), 7.26–7.33(5H, m) |
| W-1644 | $^1$H-NMR(CDCl$_3$) δ ppm: 1.08(3H, t, J=7.3), 2.62(2H, q, J=7.3), 2.76–2.97(2H, m), 3.12–3.34(2H, m), 3.51–3.66(4H, m), 3.80 (3H, s), 5.11(2H, s), 5.14(1H, d, J=12.8), 5.23(1H, d, J=12.8), 6.86(2H, d, J=8.6), 7.26(2H, d, J=8.6), 7.42(2H, d, J=7.9), 7.60 (2H, d, J=7.9) |

TABLE 79

| No | Physical Data |
|---|---|
| W-1654 | $^1$H-NMR(CDCl$_3$) δ ppm: 1.05(3H, t, J=7.3), 2.29(3H, s), 2.30 (3H, s), 2.58(2H, q, J=7.3), 2.76–2.94(2H, m), 3.20–3.29(2H, m), 3.32–3.70(4H, m), 3.79(3H, s), 5.06(1H, d, J=12.2), 5.10 (2H, s), 5.16(1H, d, J=12.2), 6.85(2H, d, J=8.6), 7.26(2H, d, J=8.6), 7.00–7.06(3H, m) |
| W-1694 | $^1$H-NMR(CDCl$_3$) δ ppm: 1.06(3H, t, J=7.3), 2.59(2H, q, J=7.3), 2.86–2.94(2H, m), 3.27–3.33(2H, m), 3.60–3.68(4H, m), 3.80 (3H, s), 5.05–5.13(4H, m), 6.85(2H, d, J=8.6), 7.04(1H, d, J=4.9), 7.20–7.29(4H, m) |
| W-1702 | $^1$H-NMR(CDCl$_3$) δ ppm: 1.07(3H, t, J=7.3), 1.41(3H, t, J=7.3), 2.60(2H, q, J=7.3), 2.70–2.95(2H, m), 3.10–3.32(2H, m), 3.56–3.70(4H, m), 4.02(2H, q, J=7.3), 5.08(1H, d, J=12.2), 5.10 (2H, s), 5.18(1H, d, J=12.2), 6.84(2H, d, J=9.1), 7.22–7.33(7H, m) |
| W-1703 | $^1$H-NMR(CDCl$_3$) δ ppm: 0.90–1.13(6H, m), 1.60–1.85(2H, m), 2.58–2.63(2H, m), 2.70–3.35(4H, m), 3.40–3.70(4H, m), 3.85–4.12(2H, m), 5.05–5.25(4H, m), 6.80–6.93(2H, m), 7.21–7.40(7H, m) |
| W-1704 | $^1$H-NMR(CDCl$_3$) δ ppm: 1.06(3H, t, J=7.3), 2.29(3H, s), 2.59 (2H, q, J=7.3), 2.74–2.95(2H, m), 3.11–3.33(2H, m), 3.54–3.64(4H, m), 5.09(1H, d, J=12.2), 5.16(2H, s), 5.19(1H, d, J=12.2), 7.05(2H, d, J=8.6), 7.28–7.36(7H, m) |
| Y-794 | $^1$H-NMR(CDCl$_3$) δ ppm: 1.07(3H, t, J=7.6), 2.15(2H, m), 2.54 (2H, m), 2.60(2H, q, J=7.6), 3.13(2H, m), 3.75(1H, m), 3.80 (3H, s), 3.96(1H, m), 5.08 and 5.17(each 1H, ABq, J=12.2), 5.10(2H, s), 6.85(2H, d, J=8.8), 7.24–7.34(7H, m) mp 105–110° C. |
| b-594 | $^1$H-NMR(CDCl$_3$) δ ppm: 1.83–1.95(1H, m), 2.12(3H, s), 2.16 (3H, s), 2.10–2.25(2H, m), 2.27–2.40(1H, m), 2.95–3.02(2H, m), 3.50–3.83(2H, m), 3.80(3H s) 5.11(2H, s), 5.16(2H, d, J=3.7), 6.86(2H, d, J=8.6), 7.20(2H, d, J=6.1), 7.26(2H, d, J=8.6), 8.57(2H, d, J=6.1) |

TABLE 80

| No | Physical Data |
|---|---|
| b-794 | $^1$H-NMR(CDCl$_3$) δ ppm: 1.07(3H, t, J=7.6), 1.94–2.37(4H, m), 2.18(3H, s), 2.60(2H, q, J=7.6), 2.96(2H, m), 3.63(2H, m), 3.80(3H, s), 5.10(2H, s), 5.11 and 5.16(each 1H, ABq, J=12.5), 6.85(2H, d, J=8.6), 7.24–7.34(7H, m) |
| b-1194 | $^1$H-NMR(CDCl$_3$) δ ppm: 1.12(3H, t, J=7.6), 1.87(1H, m), 2.15 (3H, s), 2.05–2.36(3H, m), 2.65(2H, q, J=7.6), 2.95(2H, m), 3.50–3.70(2H, m), 3.80(3H, s), 5.11(2H, s), 5.12 and 5.17 (each 1H, ABq, J=12.2) 6.85(2H, d, J=8.8), 7.19(2H, d, J=5.9), 7.25(2H, d, J=8.8), 8.56(2H, d, J=5.9) |
| e-794 | $^1$H-NMR(CDCl$_3$) δ ppm: 1.07(3H, t, J=7.3), 1.28(3H, t, J=7.3), 2.61(2H, q, J=7.3), 2.67–3.81(8H, m), 3.79(3H, s), 4.15(2H, q, J=7.3), 5.04(1H, d, J=12.2), 5.09(2H, s), 5.17(1H, d, J=12.2), 6.85(2H, d, J=8.6), 7.22–7.30(7H, m) |
| f-794 | $^1$H-NMR(CDCl$_3$) δ ppm: 1.07(3H, t, J=7.3), 2.03–2.70(4H, m), 2.60(2H, q, J=7.3), 2.90–3.10(2H, m), 3.06(2H, s), 3.50–3.80 (2H, m), 3.71(3H, s), 3.80(3H, s), 5.10(2H, s), 5.10(1H, d, J=12.8), 5.18(1H, d, J=12.8), 6.85(2H, d, J=9.2), 7.24–7.33 (7H, m) |
| g-794 | mp 107–112° C. |
| h-794 | $^1$H-NMR(CDCl$_3$) δ ppm: 1.10(3H, t, J=7.3), 2.55(3H, s), 2.56–3.90(8H, m), 2.63(2H, q, J=7.3), 3.79(3H, s), 5.08(1H, d, J=12.2), 5.11(2H, s), 5.18(1H, d, J=12.2), 6.85(2H, d, J=8.6), 7.23–7.33(7H, m) |
| i-794 | mp 89.5–91° C. |
| j-794 | $^1$H-NMR(CDCl$_3$) δ ppm: 1.07(3H, t, J=7.6), 2.08(2H, m), 2.61 (2H, q, J=7.6), 3.45(2H, br s), 3.68(2H, m), 3.79(3H, s), 5.12 (2H, s), 5.14(2H, s), 6.85(2H, d, J=8.5), 7.27(2H, d, J=8.5), 7.29–7.32(5H, m) |
| k-794 | $^1$H-NMR(CDCl$_3$) δ ppm: 1.06 and 1.07(total 3H, t, J=7.6), 1.49–1.89(2H, m), 2.19 and 2.25(total 3H, s), 2.23–2.31(2H, m), 2.45–2.53(4H, m), 2.84–3.08(2H, m), 3.55–3.74(2H, m), 3.79(3H, s), 5.08–5.20(4H, m), 6.85(2H, d, J=8.6), 7.25–7.30(7H, m) |

TABLE 81

| No | Physical Data |
|---|---|
| l-1 | $^1$H-NMR(CDCl$_3$) δ ppm: 2.13(3H, s), 2.90(3H, s), 3.07(3H, s), 3.29(3H, s), 3.99(3H, s), 6.90–7.02(3H, m), 7.23–7.29(2H, m). |
| n-776 | mp 89–92° C. |
| n-785 | $^1$H-NMR(CDCl$_3$) δ ppm: 1.07(3H, t, J=7.6), 2.63(2H, q, J=7.6), 2.94(2H, t, J=4.9), 3.29(2H, t, J=4.9), 3.59(4H, brs), 4.45(2H, d, J=4.9), 5.10(2H, s), 6.24(1H, t, J=4.9), 7.22–7.40(10H, m) |
| n-794 | $^1$H-NMR(CDCl$_3$) δ ppm: 1.08(3H, t, J=7.6), 2.63(2H, q, J=7.6), 2.94(2H, t, J=4.9), 3.29(2H, t, J=4.9), 3.59(4H, brs), 3.79(3H, s), 4.38(2H, d, J=4.9), 5.10(2H, s), 6.15(1H, t, J=4.9), 6.84(2H, d, J=8.5), 7.19(2H, d, J=8.5), 7.32(5H, m) |
| n-1456 | $^1$H-NMR(CDCl$_3$) δ ppm: 1.18(3H, t, J=7.6), 2.77(2H, q, J=7.6), 3.01(2H, t, J=4.9), 3.35(2H, t, J=4.9), 3.60–3.75(4H, m), 5.15 (2H, s), 6.93(1H, t, J=7.3), 7.08(2H, d, J=7.9), 7.25–7.40(7H, m), 8.28(1H, s) |
| n-1461 | $^1$H-NMR(CDCl$_3$) δ ppm: 1.17(3H, t, J=7.6), 2.74(2H, q, J=7.6), 2.99(2H, t, J=4.9), 3.34(2H, t, J=4.9), 3.60–3.72(4H, m), 5.15 (2H, s), 6.87–6.92(2H, m), 7.12–7.20(2H, m), 7.27–7.44 (5H, m), 8.34(1H, s) |
| n-1466 | $^1$H-NMR(CDCl$_3$) δ ppm: 1.16(3H, t, J=7.6), 2.74(2H, q, J=7.6), 3.00(2H, t, J=4.9), 3.35(2H, t, J=4.9), 3.67(4H, brs), 5.15(2H, s), 7.10(2H, d, J=8.5), 7.22(2H, d, J=8.5), 7.35(5H, m), 8.30 (1H, s) |
| n-1476 | $^1$H-NMR(CDCl$_3$) δ ppm: 1.17(3H, t, J=7.6), 2.29(3H, s), 2.76 (2H, q, J=7.6), 3.01(2H, t, J=4.9), 3.35(2H, t, J=4.9), 3.60–3.72 (4H, m), 5.14(2H, s), 6.98(2H, d, J=8.5), 7.07(2H, d, J=8.5), 7.27–7.42(5H, m), 8.21(1H, s) |
| n-1486 | $^1$H-NMR(CDCl$_3$) δ ppm: 1.17(3H, t, J=7.6), 2.75(2H, q, J=7.6), 3.02(2H, t, J=4.9), 3.35(2H, t, J=4.9), 3.64–3.75(4H, m), 3.78 (3H, s), 5.14(2H, s), 6.85(2H, d, J=9.2), 7.02(2H, d, J=9.2), 7.25–7.42(5H, m), 8.21(1H, s) |

TABLE 82

| No | Physical Data |
|---|---|
| o-794 | $^1$H-NMR(CDCl$_3$) δ ppm: 1.07(3H, t, J=7.6), 2.65(2H, q, J=7.6), 2.84(3H, s), 2.92–2.98(2H, m), 3.23–3.69(6H, m), 3.79(3H, s), 4.32(1H, d, J=14.3), 4.36(1H, d, J=14.3), 5.05(1H, d, J=12.5), 5.15(1H, d, J=12.5), 6.84(2H, d, J=8.5), 7.18(2H, d, J=8.5), 7.33(5H, m) |
| o-799 | mp 97–98° C. |
| o-1486 | $^1$H-NMR(CDCl$_3$) δ ppm: 1.15(3H, t, J=7.3), 2.74(2H, q, J=7.3), 2.97–3.20(2H, m), 3.24–3.36(1H, m), 3.38–3.52(2H, m), 3.45 (3H, s), 3.57–3.64(2H, m), 3.67–3.80(1H, m), 3.79(3H, s), 5.08(1H, d, J=12.2), 5.19(1H, d, J=12.2), 6.86(2H, d, J=9.2), 7.17(2H, d, J=9.2), 7.27–7.42(5H, m) |
| p-794 | $^1$H-NMR(CDCl$_3$) δ ppm: 1.11(3H, t, J=7.3), 1.90–2.05(1H, m), 2.49(3H, s), 2.50–3.02(6H, m), 3.30–3.46(2H, m), 3.68–3.82 (1H, m), 3.77(3H, s), 4.90(1H, d, J=17.4), 5.08(1H, d, J=12.5), 5.22(1H, d, J=12.5), 5.57(1H, d, J=17.4), 6.80–6.93(4H, m), 7.25–7.40(5H, m) |
| q-776 | mp 105–106° C. |
| q-794 | $^1$H-NMR(CDCl$_3$) δ ppm: 0.80(3H, t, J=7.3), 2.23–2.42(3H, m), 2.52–2.65(1H, m), 2.95–3.15(3H, m), 3.42(2H, t, J=4.9), 3.62–3.75(1H, m), 3.78(3H, s), 5.02–5.50(4H, m), 6.86(2H, d, J=8.5), 7.06(2H, d, J=8.5), 7.25–7.45(9H, m), 7.57(2H, dd, J=1.8, 7.9) |
| t-794 | $^1$H-NMR(CDCl$_3$) δ ppm: 1.08(3H, t, J=7.3), 2.11(2H, t, J=4.9), 2.20(3H, s), 2.32(2H, t, J=4.9), 2.63(2H, q, J=7.3), 3.07(2H, t, J=4.9), 3.64(2H, t, J=4.9), 3.79(3H, s), 4.38(2H, d, J=4.9), 5.10 (2H, s), 6.11(1H, t, J=4.9), 6.84(2H, d, J=8.5), 7.27–7.40(5H, m) |
| v-794 | $^1$H-NMR(CDCl$_3$) δ ppm: 1.09(3H, t, J=7.6), 2.63(2H, q, J=7.6), 2.95–3.30(4H, m), 3.66(2H, m), 3.80(3H, s), 4.16(2H, m), 5.06 and 5.16(each 1H, ABq, J=12.2), 5.12(2H, s), 6.84(2H, d, J=8.8), 7.25–7.33(7H, m) |
| x-10 | $^1$H-NMR(CDCl$_3$) δ ppm: 1.99(3H, s), 3.86(3H, s), 3.94(3H, s), 5.21(2H, s), 7.33(5H, m) |

TABLE 83

| No | Physical Data |
|---|---|
| x-185 | $^1$H-NMR(CDCl$_3$) δ ppm: 2.01(3H, s), 3.83(3H, s), 5.15(2H, s), 5.21(2H, s), 7.33(10H, m) |
| x-480 | mp 53–54° C. |
| y-476 | $^1$H-NMR(CDCl$_3$) δ ppm: 1.28(3H, t, J=7.3), 2.05(3H, s), 3.98 (3H, s), 4.31(2H, q, J=7.3), 5.08(2H, s), 7.15(1H, dd, J=8.8, 2.0), 7.40–7.42(4H, m) |
| z-10 | mp 88–89° C. |
| z-185 | mp 79–80° C. |
| z-476 | mp 134–136° C. |
| z-480 | mp 111–112° C. |

Agrochemical Formulations

Formulation 1

A mixture of 2 parts by weight of Compound C-180 and 98 parts by weight of talc was pulverized to obtain a powder formulation.

Formulation 2

40 Parts by weight of Compound C-180, 10 parts by weight of sodium lignosulfonate and 50 parts by weight of water were mixed to obtain a suspension formulation.

Pharmaceutical Formulations

Formulation for Injection 5 g of Compound b-251 was dissolved in 10 L of distilled water for injection to form a solution for injection, which was then dispensed into 100 ampoules.

The following Test Examples illustrate the fungicidal effects of the compound according to the present invention.

[Controlling effects on various plant diseases by foliage application (pot experiment)]

Experimental Method

A test compound was dissolved in a small amount of N,N-dimethylformamide, and the solution was diluted to a given concentration with distilled water containing a spreader, whereby preparing a liquid sample. The liquid sample was sprayed to each test plant, and after 24 hours each pathogens was inoculated by the method described below.

A % control was calculated according to the following equation.

$$\% \text{ Control} = 100 \times \frac{\text{(Severity and number of lesions in untreated plot} - \text{Severity and number of lesions in treated plot)}}{\text{(Severity and number of lesions in untreated plot)}}$$

Test Example 1

Controlling effect on rice blight (*Pyricularia oryzae*)

A two-week rice seedling (cv.: AICHIASAHI) was transplanted in a plastic cup which was 9 cm in diameter and cultivated for 2 weeks, and then the test compound in the form of a solution or a suspension was sprayed to the foliage of the rice seedling. A conidia suspension of a rice blight microorganism (*Pyricularia oryzae*) cultured in an oatmeal medium was inoculated by spraying, and after the inoculation the test plant was kept in a moist chamber (28° C., 100% RH) for 24 hours, and subsequently cultivated in a green house for 5 days. Six days after the inoculation, the number of the lesions on the leaves of the inoculated plant was measured to calculate the % control.

The results are shown below.

| Compound No. | Controlling effect on rice blight (*Pyricularia oryzae*) by foliage application at 500 ppm (% control) |
|---|---|
| C-11 | 90 |
| C-86 | 90 |
| C-95 | 90 |
| C-96 | 90 |
| Reference agent: | |
| Fthalide | 97 |

Test Example 2

Controlling effect on cucumber mildew microorganism (*Sphaerotheca fuliginea*)

A seed of a cucumber (cv.: TSUKUBASHIROIBO) was sown in a plastic cup which was 9 cm in diameter, and cultivated for 2 to 3 weeks. The liquid test sample in the form of a solution or suspension was sprayed on the surface of the first leaf. The pathogen was inoculated to the leaf by spraying a conidia suspension of a cucumber mildew microorganism (*Sphaerotheca fuliginea*) which had been cultured on a cucumber leaf. After the inoculation, the plant was kept in a greenhouse at 20° C. for 10 days. Then, the infected area on the leaf was observed, and the % control was calculated.

The results are shown below.

| Compound No. | Controlling effect on cucumber mildew microorganism (*Sphaerotheca fuliginea*) by foliage application at 500 ppm (% control) |
|---|---|
| B-476 | 100 |
| C-180 | 100 |
| C-780 | 97 |
| F-180 | 100 |
| Reference agent: | |
| Fenarimol | 100 |

Test Example 3

Controlling Effect on Wheat Powdery Mildew Microorganism (*Erysiphe graminis* f.sp.tritici)

A seed of a wheat (cv.: NORIN No.61) was sown in a plastic cup which was 9 cm in diameter and cultivated for 2 to 3 weeks. The test compound in the form of a solution or suspension was sprayed to a seedling, and conidia of a wheat powdery mildew microorganism (*Erysiphe graminis* fsp.tritici) cultured on a wheat leaf was dropped on the test plant to inoculate the plant with the pathogen. After the inoculation, the plant was kept in a green house at 20° C. for 10 days. The infected area on the leaf was observed, and the % control was calculated.

The results are shown below.

| Compound No. | Controlling effect on wheat powdery mildew microorganism (*Erysiphe graminis* f.sp.tritici) by foliage application at 500 ppm (% control) |
|---|---|
| C-11 | 90 |
| C-86 | 90 |
| C-96 | 90 |
| C-176 | 90 |

-continued

| Compound No. | Controlling effect on wheat powdery mildew microorganism (*Erysiphe graminis* f.sp.tritici) by foliage application at 500 ppm (% control) |
|---|---|
| C-180 | 90 |
| C-251 | 90 |
| C-276 | 90 |
| C-780 | 90 |
| F-180 | 90 |
| Reference agent: | |
| Fenarimol | 97 |

The tachykinin receptor antagonistic effect of a compound according to the present invention was investigated by the method described below.

[Effect of compound on capsaicin-induced increase in blood vessel permeability]

Method

5 Minutes after giving Evans Blue (30 mg/kg, i.v.) to a guinea pig anesthetized with pentobarbital (30 mg/kg, i.p.), a test compound dissolved in dimethylsulfide was injected intravenously. After further 5 minutes, capsaicin (0.15 mg/kg, i.v.) was given to induce the plasma transudation. 5 Minutes after administration of capsaicin, the guinea pig was sacrificed to isolate the trachea and the urinary bladder. After extraction with formamide for 24 hours, the dye content in each tissue was quantified on the basis of the absorbance at 620 nm, and the amount of the dye transudated into the tissue was calculated from the calibration curve.

By the method described above, the amount of the compound required to obtain 50% suppression ($ED_{50}$) was determined and represented in units (mg/kg).

| | $ED_{50}$ (mg/kg) | |
|---|---|---|
| Compound No. | Guinea pig trachea | Guinea pig urinary bladder |
| M-11 | 0.024 | |
| M-86 | 0.085 | |
| W-96 | 0.040 | |
| W-176 | 0.145 | 0.075 |
| b-180 | 0.054 | 0.087 |
| b-251 | 0.017 | 0.017 |

Industrial Applicability

A compound according to the present invention is useful as a fungicide, especially as an agricultural fungicide. It also has a tachykinin receptor antagonistic effect, and thus is useful as a pharmaceutical.

What is claimed is:
1. A compound represented by Formula (I):

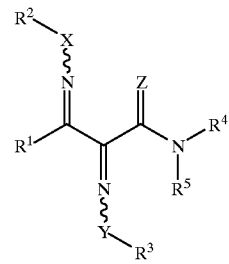

wherein $R^1$ is an optionally substituted aryl, an optionally substituted alkyl or an optionally substituted cycloalkyl; $R^2$ is an optionally substituted alkyl, an optionally substituted cycloalkyl, an optionally substituted alkenyl, an optionally substituted alkynyl, an optionally substituted alkylsulfonyl, an optionally substituted aryl, an optionally substituted arylsulfonyl or an optionally substituted heterocyclic group; $R^3$ is an optionally substituted alkyl, an optionally substituted cycloalkyl, an optionally substituted alkenyl, an optionally substituted alkynyl, an optionally substituted alkylsulfonyl, an optionally substituted aryl, an optionally substituted arylsulfonyl or an optionally substituted heterocyclic group; $R^4$ and $R^5$ are the same or different from each other and each is a hydrogen atom, an optionally substituted alkyl, an optionally substituted cycloalkyl or an optionally substituted alkoxy, or $R^4$ and $R^5$ may be taken together with their adjacent nitrogen atom to form an optionally substituted monocyclic ring or polycyclic ring; X and Y are the same or different from each other and each is an oxygen atom or an $NR^6$ wherein $R^6$ is a hydrogen atom, an optionally substituted alkyl, an optionally substituted aryl, an optionally substituted alkanoyl or an optionally substituted aroyl; Z is an oxygen atom or a sulfur atom; a wave-shaped line (~) represents the configuration of an E form or a Z form or a mixture thereof;
provided that when $R^2$ is an optionally substituted benzyl then the substituent is not a group represented by formula:

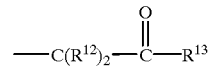

wherein $(R^{12})_2$ is $H_2$, $=O$, $=CH-OH$, $=CHOCH_3$, $=N-OH$ or $=N-OCH_3$; and $R^{13}$ represents an alkoxy or a monoalkylamino;
and a salt or a hydrate thereof.
2. A compound or a salt or a hydrate thereof according to claim 1 wherein $R^1$ is an aryl or an alkyl; $R^2$ is an optionally substituted alkyl, alkenyl, alkynyl, aryl or heterocyclic group; $R^3$ is an optionally substituted alkyl, alkenyl, alkynyl, an optionally substituted aryl, an optionally substituted arylsulfonyl or heterocyclic group; $R^4$ and $R^5$ are the same or different from each other and each is a hydrogen atom, an alkyl or an alkoxy, or $R^4$ and $R^5$ may be taken together with their adjacent nitrogen atom to form an optionally substituted monocyclic ring; X and Y are the same or different from each other and each is an oxygen atom or a $NR^6$ wherein $R^6$ is a hydrogen atom, alkyl, aryl, alkanoyl or aroyl.
3. A compound or a salt or a hydrate thereof according to claim 1 wherein $R^1$ is methyl, ethyl, propyl, isopropyl or an optionally substituted phenyl.

4. A compound or a salt or a hydrate thereof according to claim 1 wherein $R^2$ is methyl, methoxymethyl, ethyl, allyl, cinnamyl, 2-propynyl, 2-butynyl, 2-pyridyl, an optionally substituted phenyl, an optionally substituted benzyl, an optionally substituted 2-pyridylmethyl, an optionally substituted 3-pyridylmethyl, an optionally substituted 4-pyridylmethyl, an optionally substituted 2-thenyl or an optionally substituted 3-thenyl.

5. A compound or a salt or a hydrate thereof according to claim 1 wherein $R^3$ is methyl, ethyl, propyl, isopropyl, allyl, cinnamyl, 2-propynyl, 2-butynyl, 2-pyridyl, an optionally substituted benzyl, an optionally substituted 2-phenylethyl, an optionally substituted 2-pyridylmethyl, an optionally substituted 3-pyridylmethyl, an optionally substituted 4-pyridylmethyl or an optionally substituted benzenesulfonyl.

6. A compound or a salt or a hydrate thereof according to claim 1 wherein —$NR^4R^5$ is —$NH_2$, —NHMe, —$NMe_2$, —$NEt_2$, —N(Me)Et, —N(OMe)Me, an optionally substituted 1-pyrrolidinyl, an optionally substituted piperidino, an optionally substituted morpholino, an optionally substituted 4-thiomorpholinyl, an optionally substituted 1-piperazinyl, an optionally substituted 2-oxazolanyl or an optionally substituted diazepan-1-yl.

7. A compound or a salt or a hydrate thereof according to claim 1 wherein X is an oxygen atom, —NH—, —N(Me)— or —N(Ph)—.

8. A compound or a salt or a hydrate thereof according to claim 1 wherein Y is an oxygen atom, —NH—, —N(Me)—, —N(Et)—, —NP(h)—, —N(Ac)— or —N(Bz)—.

9. A pharmaceutical composition containing as an active ingredient a compound according to claim 1.

10. An agrochemical composition, comprising a compound of claim 1 and an agrochemically-acceptable carrier or diluent.

11. A fungicide composition, comprising a compound of claim 1 and a fungicidally-acceptable carrier or diluent.

12. A tachykinin receptor antagonist composition, comprising a compound of claim 1 and a pharmaceutically-acceptable carrier or diluent.

13. A substance P receptor antagonist composition, comprising a compound of claim 1 and a pharmaceutically-acceptable carrier or diluent.

14. A compound represented by Formula (II):

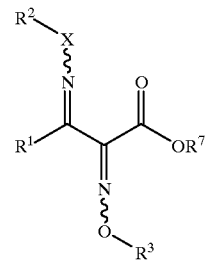

II wherein $R^7$ is a hydrogen atom or alkyl, $R^1$ is an optionally substituted aryl, an optionally substituted alkyl or an optionally substituted cycloalkyl; $R^2$ is an optionally substituted alkyl, an optionally substituted cycloalkyl, an optionally substituted alkenyl, an optionally substituted alkynyl, an optionally substituted alkylsulfonyl, an optionally substituted aryl, an optionally substituted arylsulfonyl or an optionally substituted heterocyclic group; $R^3$ is an optionally substituted alkyl, an optionally substituted cycloalkyl, an optionally substituted alkenyl, an optionally substituted alkynyl, an optionally substituted alkylsulfonyl, an optionally substituted aryl, an optionally substituted arylsulfonyl or an optionally substituted heterocyclic group; X is an oxygen or an $NR^6$ wherein $R^6$ is a hydrogen atom, alkyl, aryl, alkanoyl or aroyl; provided that when $R^2$ is optionally substituted benzyl then the substituent is not a group represented by Formula:

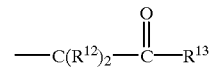

wherein $(R^{12})_2$ is $H_2$, =O, =CH—OH, =CHOCH$_3$, =N—OH or =N—OCH$_3$; $R^{13}$ is alkoxy or monoalkylamino; and at least one of $R^1$, $R^3$ and $R^7$ is not methyl.

* * * * *